US011510966B2

(12) United States Patent
Kolls et al.

(10) Patent No.: US 11,510,966 B2
(45) Date of Patent: Nov. 29, 2022

(54) USE OF IL-22 IN TREATING NECROTIZING ENTEROCOLITIS

(71) Applicants: Evive Biotechnology (Shanghai) Ltd, Shanghai (CN); UNIVERSITY OF PITTSBURGH—OF THE COMMONWEALTH SYSTEM OF HIGHER EDUCATION, Pittsburgh, PA (US)

(72) Inventors: Jay Kennedy Kolls, Mandeville, LA (US); Misty Lynn Good, St. Louis, MO (US); Xiaoqiang Yan, Shanghai (CN)

(73) Assignees: Evive Biotechnology (Shanghai) Ltd, Shanghai (CN); University Of Pittsburgh—Of The Commonwealth System Of Higher Education, Pittsburgh, PA (US)

( * ) Notice: Subject to any disclaimer, the term of this patent is extended or adjusted under 35 U.S.C. 154(b) by 517 days.

(21) Appl. No.: 16/093,583

(22) PCT Filed: Apr. 14, 2017

(86) PCT No.: PCT/US2017/027806
§ 371 (c)(1),
(2) Date: Oct. 12, 2018

(87) PCT Pub. No.: WO2017/181143
PCT Pub. Date: Oct. 19, 2017

(65) Prior Publication Data
US 2021/0100877 A1   Apr. 8, 2021

Related U.S. Application Data

(60) Provisional application No. 62/323,584, filed on Apr. 15, 2016.

(51) Int. Cl.
*A61K 38/20* (2006.01)
*A61P 1/00* (2006.01)
*A61K 9/00* (2006.01)

(52) U.S. Cl.
CPC ............ *A61K 38/20* (2013.01); *A61K 9/0019* (2013.01); *A61P 1/00* (2018.01)

(58) Field of Classification Search
CPC .......... A61K 38/20; A61K 9/0019; A61P 1/00
See application file for complete search history.

(56) References Cited

U.S. PATENT DOCUMENTS

| 4,179,337 | A | 12/1979 | Davis |
|---|---|---|---|
| 4,301,144 | A | 11/1981 | Iwashita |
| 4,399,216 | A | 8/1983 | Axel |
| 4,496,689 | A | 1/1985 | Mitra |
| 4,640,835 | A | 2/1987 | Shimizu |
| 4,657,760 | A | 4/1987 | Kung |
| 4,670,417 | A | 6/1987 | Iwasaki |
| 4,683,195 | A | 7/1987 | Mullis et al. |
| 4,683,202 | A | 7/1987 | Mullis |
| 4,791,192 | A | 12/1988 | Nakagawa |
| 4,849,227 | A | 7/1989 | Cho |
| 4,943,529 | A | 7/1990 | Van Den Berg |
| 4,965,188 | A | 10/1990 | Mullis |
| 5,010,182 | A | 4/1991 | Brake |
| 5,206,344 | A | 4/1993 | Katre |
| 5,225,212 | A | 7/1993 | Martin |
| 5,428,130 | A | 6/1995 | Capon |
| 5,500,362 | A | 3/1996 | Robinson |
| 5,624,821 | A | 4/1997 | Winter |
| 5,648,260 | A | 7/1997 | Winter |
| 5,654,010 | A | 8/1997 | Johnson |
| 5,821,337 | A | 10/1998 | Carter |
| 6,194,551 | B1 | 2/2001 | Idusogie |
| 6,274,710 | B1 | 8/2001 | Dumoutier |
| 6,306,908 | B1 | 10/2001 | Carlson et al. |
| 6,331,613 | B1 | 12/2001 | Dumoutier |
| 6,359,117 | B1 | 3/2002 | Dumoutier |
| 6,551,799 | B2 | 4/2003 | Gurney |
| 6,737,056 | B1 | 5/2004 | Presta |
| 6,797,493 | B2 | 9/2004 | Sun |
| 7,226,591 | B2 | 6/2007 | Gurney |
| 7,307,161 | B1 | 12/2007 | Jacobs |
| 7,332,581 | B2 | 2/2008 | Presta |
| 7,371,826 | B2 | 5/2008 | Presta |
| 7,459,533 | B2 | 12/2008 | Jacobs |
| 7,585,646 | B2 | 9/2009 | Jacobs |
| 7,651,694 | B2 | 1/2010 | Lee |

(Continued)

FOREIGN PATENT DOCUMENTS

| CA | 2695734 A1 | 2/2009 |
|---|---|---|
| CA | 2705007 A1 | 5/2009 |

(Continued)

OTHER PUBLICATIONS

Walsh et al. "Necrotizing enterocolitis: treatment based on staging criteria", Pediatr Clin North Am. Feb. 1986;33(1):179-201. (Year: 1986).*
Clinical Trial NCT00355602: Antibiotics for the Treatment of Ulcerative Colitis, [online] U.S. National Library of Medicine < URL https://clinicaltrials.gov/ct2/show/NCT00355602 > version Feb. 11, 2009, retrieved from the internet on Sep. 27, 2021 (Year: 2009).*
Clark et al. "Intestinal barrier failure during experimental necrotizing enterocolitis: protective effect of EGF treatment", Am J Physiol Gastrointest Liver Physiol. Nov. 2006;291(5):G938-49. (Year: 2006).*
Emani et al. "Role of the host defense system and intestinal microbial flora in the pathogenesis of necrotizing enterocolitis." Surg Infect (Larchmt). Oct. 2009;10(5):407-17. (Year: 2009).*
McElroy et al. "Paneth cells and necrotizing enterocolitis: a novel hypothesis for disease pathogenesis", Neonatology. 2013;103(1):10-20 (Year: 2013).*

(Continued)

*Primary Examiner* — Amy E Juedes
*Assistant Examiner* — Peter Johansen
(74) *Attorney, Agent, or Firm* — Morrison & Foerster LLP

(57) ABSTRACT

The present invention relates to methods of preventing and/or treating necrotizing enterocolitis or other intestinal inflammations using an IL-22, a dimer or a multimer thereof.

21 Claims, 6 Drawing Sheets

Specification includes a Sequence Listing.

(56) References Cited

U.S. PATENT DOCUMENTS

| | | |
|---|---|---|
| 7,666,402 B2 | 2/2010 | Huang |
| 7,696,158 B2 | 4/2010 | Huang |
| 7,718,604 B2 | 5/2010 | Huang |
| 7,972,833 B2 | 7/2011 | Dumoutier |
| 7,981,448 B2 | 7/2011 | Otterbein et al. |
| 8,048,984 B2 | 11/2011 | Jacobs |
| 8,178,082 B2 | 5/2012 | Gurney |
| 8,178,675 B2 | 5/2012 | Romantsev |
| 8,945,528 B2 | 2/2015 | Yan |
| 8,956,605 B2 | 2/2015 | Huang |
| 8,980,949 B2 | 3/2015 | Bar-yosef et al. |
| 9,352,024 B2 | 5/2016 | Wu |
| 9,629,898 B2 | 4/2017 | Yan |
| 10,087,227 B2 | 10/2018 | Scheer |
| 10,160,793 B2 | 12/2018 | Scheer |
| 10,543,169 B2 | 1/2020 | Yan |
| 10,786,551 B2 | 9/2020 | Huang et al. |
| 2001/0023070 A1 | 9/2001 | Ebner et al. |
| 2002/0102723 A1 | 8/2002 | Gurney |
| 2003/0100076 A1 | 5/2003 | Gurney |
| 2003/0186387 A1 | 10/2003 | Ebner |
| 2003/0235561 A1 | 12/2003 | Vandenburgh et al. |
| 2004/0258623 A1 | 12/2004 | Xu et al. |
| 2005/0014934 A1 | 1/2005 | Hinton |
| 2005/0148029 A1 | 7/2005 | Buechler et al. |
| 2007/0172457 A1 | 7/2007 | Ebner |
| 2007/0207943 A1 | 9/2007 | Ebner |
| 2008/0031882 A1 | 2/2008 | Liang et al. |
| 2008/0069798 A1 | 3/2008 | Huang et al. |
| 2008/0069799 A1 | 3/2008 | Huang et al. |
| 2008/0138314 A1 | 6/2008 | Huang et al. |
| 2008/0241246 A1 | 10/2008 | Sakthivel et al. |
| 2008/0293629 A1 | 11/2008 | Rosen et al. |
| 2009/0202475 A1 | 8/2009 | Abbas |
| 2009/0221008 A1 | 9/2009 | Yu et al. |
| 2010/0015086 A1 | 1/2010 | Huang et al. |
| 2010/0255508 A1 | 10/2010 | Gelzleichter et al. |
| 2011/0091417 A1 | 4/2011 | Gurney |
| 2011/0262385 A1 | 10/2011 | Huang |
| 2011/0268696 A1 | 11/2011 | Huang et al. |
| 2011/0280828 A1 | 11/2011 | Abbas |
| 2013/0171100 A1 | 7/2013 | Yan et al. |
| 2014/0314711 A1 | 10/2014 | Scheer |
| 2014/0377222 A1 | 12/2014 | Huang |
| 2015/0147293 A1 | 5/2015 | Wu |
| 2015/0202267 A1 | 7/2015 | Yan |
| 2016/0263020 A1 | 9/2016 | Yan |
| 2016/0271221 A1 | 9/2016 | Yan |
| 2016/0287670 A1* | 10/2016 | Van Den Brink ...... A61P 37/06 |
| 2017/0088596 A1 | 3/2017 | Scheer et al. |
| 2017/0320926 A1 | 11/2017 | Scheer et al. |
| 2018/0015130 A1 | 1/2018 | Berry et al. |
| 2018/0028614 A1 | 2/2018 | Huang |
| 2020/0155448 A1 | 5/2020 | Yan et al. |
| 2021/0138038 A1 | 5/2021 | Van Den Brink et al. |

FOREIGN PATENT DOCUMENTS

| | | |
|---|---|---|
| CN | 1264596 A | 8/2000 |
| CN | 1381512 A | 11/2002 |
| CN | 1652802 A | 8/2005 |
| CN | 101168049 A | 4/2008 |
| CN | 101218254 A | 7/2008 |
| CN | 101225110 A | 7/2008 |
| CN | 102380091 A | 3/2012 |
| CN | 103118699 A | 11/2014 |
| CN | 104623637 A | 5/2015 |
| CN | 105143252 A | 12/2015 |
| EP | 0036776 A2 | 9/1981 |
| EP | 0073657 A1 | 3/1983 |
| EP | 0117058 A2 | 8/1984 |
| EP | 0117060 A2 | 8/1984 |
| EP | 0139383 A1 | 5/1985 |
| EP | 0183070 A2 | 6/1986 |
| EP | 0244234 A2 | 11/1987 |
| EP | 0362179 A2 | 4/1990 |
| EP | 0394538 A1 | 10/1990 |
| EP | 0402226 A1 | 12/1990 |
| EP | 1748789 B1 | 12/2010 |
| EP | 3065763 A1 | 9/2016 |
| JP | 2008508862 A | 3/2008 |
| JP | 2011507863 A | 3/2011 |
| JP | 2013536254 A | 9/2013 |
| WO | 198705330 A1 | 9/1987 |
| WO | 198905859 A1 | 6/1989 |
| WO | 199100357 A1 | 1/1991 |
| WO | 199408606 A1 | 4/1994 |
| WO | 199429351 A2 | 12/1994 |
| WO | 199513312 A1 | 5/1995 |
| WO | 199522419 A1 | 8/1995 |
| WO | 199607399 A1 | 3/1996 |
| WO | 199634103 A1 | 10/1996 |
| WO | 199640072 A2 | 12/1996 |
| WO | 199703692 A1 | 2/1997 |
| WO | 199932139 A1 | 7/1999 |
| WO | 199951642 A1 | 10/1999 |
| WO | 199954440 A1 | 10/1999 |
| WO | 199961617 A1 | 12/1999 |
| WO | 2002029098 A1 | 4/2002 |
| WO | 2003013589 A1 | 2/2003 |
| WO | 2003089569 A2 | 10/2003 |
| WO | 2004056312 A2 | 7/2004 |
| WO | 2005044292 A2 | 5/2005 |
| WO | 2005100402 A1 | 10/2005 |
| WO | 2006000448 A2 | 1/2006 |
| WO | 2006029879 A2 | 3/2006 |
| WO | 2006073508 A1 | 7/2006 |
| WO | 2006088833 A2 | 8/2006 |
| WO | 2007047796 A2 | 4/2007 |
| WO | 2007115230 A2 | 10/2007 |
| WO | 2009020844 A1 | 2/2009 |
| WO | 2009041734 A1 | 4/2009 |
| WO | 2009062102 A2 | 5/2009 |
| WO | 2009079024 A1 | 6/2009 |
| WO | 2010081112 A1 | 7/2010 |
| WO | 2011087986 A1 | 7/2011 |
| WO | 2012028089 A1 | 3/2012 |
| WO | 2013097748 A1 | 7/2013 |
| WO | 2014145016 A2 | 9/2014 |
| WO | 2015067198 A1 | 5/2015 |
| WO | 2015067199 A1 | 5/2015 |
| WO | 2015070077 A1 | 5/2015 |
| WO | 2015197861 A1 | 12/2015 |
| WO | 2016086205 A2 | 6/2016 |
| WO | 2017181143 A1 | 10/2017 |
| WO | 2019148020 A1 | 8/2019 |
| WO | 2019148026 A1 | 8/2019 |
| WO | 2019165140 A1 | 8/2019 |
| WO | 2021160163 A1 | 8/2021 |
| WO | 2021164744 A1 | 8/2021 |

OTHER PUBLICATIONS

Walker et al. "Intestinal intraepithelial lymphocyte-enterocyte crosstalk regulates production of bactericidal angiogenin 4 by Paneth cells upon microbial challenge", PLoS One. Dec. 17, 2013;8(12):e84553. (Year: 2013).*

Adachi, M. et al. (2005). "Clinical Syndromes of Alcoholic Liver Disease," Digestive Diseases 23(3-4):255-263.

Adams, L.A. et al. (2006). "Treatment of Non-Alcoholic Fatty Liver Disease," Postgrad Med J 82:315-322.

Afrazi, A. et al. (May 1, 2012, Epub Mar. 28, 2012) "Intracellular Heat Shock Protein-70 Negatively Regulates TLR4 Signaling In The Newborn Intestinal Epithelium," J Immunol. 188(9):4543-4557.

Anand, R.J. et al. (Feb. 2007) "The Role Of The Intestinal Barrier In The Pathogenesis Of Necrotizing Enterocolitis," Shock 27(2):124-133.

Ananthakrishnan, A.N. et al. (Jan. 2018, e-pub Oct. 11, 2017) "Environmental triggers in IBD: a review of progress and evidence," Nat Rev Gastroenterol Hepatol. 15(1):39-49.

(56) References Cited

OTHER PUBLICATIONS

Arab, J.P. et al. (e-pub Nov. 27, 2019). "An Open Label, Dose Escalation Study To Assess The Safety And Efficacy Of IL-22 Agonist F-652 In Patients With Alcoholic Hepatitis," Hepatology 72(2):441-453, 30 pages.

Asiedu, C. et al. (2007). "Cloning and Characterization of Recombinant Rhesus Macaque IL-10/Fc(ala-ala) Fusion Protein: A Potential Adjunct for Tolerance Induction Strategies," Cytokine 40:183-192.

Asplund, S. et al. (1998). "Chronic Mucosal Changes of the Colon in Graft-versus-Host Disease," Mod Pathol 11(6):513-515.

Aujla, S.J. et al. (Mar. 2008, e-pub. Feb. 10, 2008). "IL-22 Mediates Mucosal Host Defense Against Gram-Negative Bacterial Pneumonia," Nat Med 14(3):275-281.

Australian Notice of Acceptance dated Feb. 18, 2020, for Patent Application No. 2014346051 filed on May 4, 2016, three pages.

Australian Office Action dated May 3, 2019 for AU Application No. 2014346051 filed on May 4, 2016, 4 pages.

Ballance, D.J. et al. (Apr. 15, 1983). "Transformation of Aspergillus Nidulans by the Orotidine- 5'-Phosphate Decarboxylase Gene of Neurospora Crassa," Biochem. Biophys. Res. Commun. 112(1):284-289.

Balthazar, E.J. et al. (Feb. 1990). "Acute Pancreatitis: Value of CT in Establishing Prognosis," Radiology 174(2):331-336.

Balthazar, E.J. et al. (Sep. 1985). "Acute Pancreatitis: Prognostic Value of CT," Radiology 156(3):767-772.

Bamba, T. et al. (Aug. 2003). "Bacterial Translocation From Basic To Clinical Study," Nihon Shokakibyo Gakkai Zasshi The Japanese Journal of Gastro-Enterology 100(8):957, 9 pages.

Banks, P.A. et al. (Oct. 2006). "Practice Guidelines in Acute Pancreatitis," The American Journal of Gastroenterology 101(10): 2379-2400.

Barker, N. et al. (Oct. 25, 2007, e-pub. Oct. 14, 2007). "Identification of Stem Cells in Small Intestine and Colon by Marker Gene Lgr5," Nature 449:1003-1007.

Barker, N. et al. (Oct. 5, 2012). "Identifying the Stem Cell of the Intestinal Crypt: Strategies and Pitfalls," Cell Stem Cell 11:452-460.

Basha, S. et al. (Sep. 2014). "Immune Responses in Neonates," Expert Rev Clin Immunol. 10(9):1171-1184.

Beach, D. et al. (Mar. 12, 1981). "High-frequency Transformation of the Fission Yeast *Schizosaccharomyces pombe*," Nature 290:140-142.

Bell, M.J. et al. (Jan. 1978) "Neonatal Necrotizing Enterocolitis. Therapeutic Decisions Based Upon Clinical Staging," Ann Surg. 187(1):1-7.

Bingold, T.M. et al. (Oct. 2010). "Interleukin-22 Detected In Patients With Abdominal Sepsis," Shock 34(4):337-340.

Blazar, B. R., et al. (May 11, 2012). "Advances in Graft-Versus-Host Disease Biology and Therapy," Nat Rev Immunol 12(6):443-458.

Bone, R.C. et al. (Jun. 1, 1992). "Definitions for Sepsis and Organ Failure and Guidelines for the Use of Innovative Therapies in Sepsis," Chest 101:1644-1655.

Browning, J.D. et al. (Jul. 2004). "Molecular Mediators of Hepatic Steatosis and Liver Injury," The Journal of Clinica Investigation 114(2):147-152.

Brüggemann, M. et al. (Nov. 1, 1987). "Comparison of the Effector Functions of Human Immunoglobulins Using a Matched Set of Chimeric Antibodies," J. Exp. Med. 166:1351-1361.

Caballero, F. et al. (2009). "Enhanced Free Cholestrol, SREBP-2 and StAR Expression in Human NASH," Journal of Hepatology 50:789-796.

Petrovic, A. et al. (Feb. 15, 2004; Epub Oct. 16, 2003) "LPAM (alpha 4 beta 7 integrin) is an important homing integrin on alloreactive T cells in the development of intestinal graft-versus-host disease." Blood. 103:1542-1547.

Canadian Office Action dated Jun. 28, 2017, for Canadian Application No. 2,809,900, filed on Feb. 28, 2013, 4 pages.

Carmon, K.S. et al. (Jun. 2012; e-pub. Apr. 2, 2012). "LGR5 Interacts and Cointernalizes with Wnt Receptors to Modulate Wnt/β-Catenin Signaling," Mol Cell Biol 32(11):2054-2064.

Carryer, H.M. (Jul. 1950). "The Effect of Cortisone of Bronchial Asthma and Hay Fever Occurring in Subjects Sensitive to Ragweed Pollen," Journal of Allergy 21(4):282-287.

Carter, P. et al. (Feb. 1992). "High Level *Escherichia coli* Expression and Production of a Bivalent Humanized Antibody Fragment," Bio/Technology 10:163-167.

Case, M. E. et al. (Oct. 1979)."Efficient Transformation of Neurospora Crassa by Utilizing Hybrid Plasmid DNA," Proc. Natl. Acad. Sci. U. S. A. 76(10):5259-5263.

Cella, M. et al. (Feb. 2009, e-pub. Nov. 2, 2008). "A Human Natural Killer Cell Subset Provides an Innate Source of IL-22 for Mucosal Immunity," Nature 457:722-725.

Chan, H.L-Y. et al. (Jun. 2007). "How Should We Manage Patients With Non-Alcoholic Fatty Liver Disease In 2007?" Journal of Gastroenterology and Hepatology 22(6):801-808.

Chang, A.C.Y. et al. (Oct. 19, 1978). "Phenotypic Expression in *E. coli* of a DNA Sequence Coding for Mouse Dihydrofolate Reductase," Nature 275(5681):617-624.

Cheadle, C. et al. (Jan. 1992). "Cloning and Expression of the Variable Regions of Mouse Myeloma Protein MOPC315 in *E. coli*: Recovery of Active FV Fragments," Mol Immunol 29(1):21-30. (Abstract Only).

Chen, M.L. et al. (May 2016). "Cytokine Networks and T-Cell Subsets in Inflammatory Bowel Diseases," Inflamm Bowel Dis 22(5):1157-1167.

Chinese Office Action dated Feb. 11, 2019, for CN Application No. 2014800611889 filed on May 6, 2016, 14 pages. (Machine English Translation of the OA is provided).

Choi, S. M. et al. (Mar. 2013). "Innate Stat3-Mediated Induction of the Antimicrobial Protein Reg3γ is Required for Host Defense Against MRSA Pneumonia," J Exp Med 210:551-561.

Clayburgh, D.R. et al. (Mar. 2004; e-published on Jan. 19, 2004). "A Porous Defense: the Leaky Epithelial Barrier in Intestinal Disease," Lab Invest 84(3):282-291.

Clinical Research (2006). vol. 83, No. 2, p. 238-242. (English translation of relevant parts only).

Clynes, R. et al. (Jan. 1998). "Fc Receptors are Required in Passive and Active Immunity to Melanoma," Proc. Natl. Acad. Sci. U.S.A. 95:652-656.

Cobleigh, M.A. et al. (Jan. 2013). "Protective and Pathological Properties of IL-22 in Liver Disease: Implications for Viral Hepatitis," Am. J. Pathology 182(1):21-28.

Cosnes, J. et al. (2011). "Epidemiology and Natural History of Inflammatory Bowel Diseases," Gastroenterology 140:1785-1794.

Couturier, M. et al. (Jul. 2013, e-pub Feb. 12, 2013) "IL-22 Deficiency In Donor T Cells Attenuates Murine Acute Graft-Versus-Host Disease Mortality While Sparing The Graft-Versus-Leukemia Effect," Leukemia. 27 (7):1527-1537.

Cox, G.N. et al. (2004). "Enhanced Circulating Half-Life and Hematopoietic Properties of a Human Granulocyte Colony-Stimulating Factor/Immunoglobulin Fusion Protein," Exp. Hematol. 32:441-449.

Cragg, M.S. et al. (Apr. 1, 2004). "Antibody Specificity Controls In Vivo Effector Mechanisms Of Anti-CD20 Reagents," Blood 103(7):2738-2743.

Cragg, M.S. et al. (Feb. 1, 2003). "Complement-Mediated Lysis By Anti-CD20 Mab Correlates With Segregation Into Lipid Rafts," Blood 101(3):1045-1052.

Craig, D.G.N. et al. (Feb. 2010). "Review Article: The Current Management Of Acute Liver Failure," Alimentary Pharmacology and Therapeutics 31(3):345-358.

Dall'Acqua, W. et al. (1998). "Contribution of Domain Interface Residues to the Stability of Antibody CH3 Domain Homodimers", Biochemistry37:9266-9273.

Dambacher, J. et al. (Mar. 2008). "The Role of Interieukin-22 in Hepatitis C Virus Infection," Cytokine 41 (3):209-216.

Das, R. et al. (Mar. 5, 2009). "Interleukin-23 Secretion by Donor Antigen-Presenting Cells is Critical for Organ-Specific Pathology in Graft-Versus-Host Disease," Blood 113(10):2352-2362.

(56) References Cited

OTHER PUBLICATIONS

De Lau, W. et al. (Aug. 18, 2011). "Lgr5 Homologues Associate with Wnt Receptors and Mediate R-spondin Signalling," Nature 476:293-297.
De Oliveira Neto, M. et al. (Mar. 1, 2008; e-pub. Nov. 16, 2007). "Interleukin-22 Forms Dimers That are Recognized by Two Interleukin-22R1 Receptor Chains," Biophys. J. 94(5):1754-1765.
Deboer, H.A. et al. (Jan. 1983). "The Tac Promoter: a Functional Hybrid Derived From the trp and lac Promoters," Proc. Natl. Acad. Sci. U.S.A. 80(1):21-25.
Delaney, A.P. et al. (2011). "The Role Of Albumin As A Resuscitation Fluid For Patients With Sepsis: A Systematic Review And Meta-Analysis," Grit Care Med 39(2):386-391.
Denning, T.L. et al. (Feb. 2017, e-pub Dec. 9, 2016) "Pathogenesis Of NEC: Role Of The Innate And Adaptive Immune Response," Semin Perinatol. 41(1):15-28.
Diefenbach, A. (Aug. 24, 2012). "Interleukin-22 , the Guardian of the Intestinal Stem Cell Niche?" Immmunity 37:196-198.
Dimartino, J.F. et al. (Sep. 1999). "Mill Rearrangements in Haematological Malignancies: Lessons from Clinical and Biological Studies," Br J Haematol. 106(3):614-626.
Dubois, M.-J. et al. (Oct. 2006). "Albumin Administiation Improves Organ Function In Critically Ill Hypoalbuminemic Patients: A Prospective, Randomized, Controlled, Pilot Study," Grit Care Med 34(10)2536-2540. (Abstract Only).
Dudakov, J.A. et al. (2015, e-pub Feb. 11, 2015). "Interleukin-22: Immunobiology And Pathology," Annu Rev Immunol. 33:747-785.
Dudakov, J.A. et al. (Apr. 6, 2012, e-pub Mar. 1, 2012). "Interleukin-22 Drives Endogenous Thymic Regeneration In Mice," Science 336(6077):91-95.
Dumoutier, L. et al. (Aug. 29, 2000). "Human Interleukin-10-Related T Cell-Derived Inducible Factor: Molecular Cloning and Functional Characterization as an Hepatocyte-Stimulating Factor," PNAS 97(18):10144-10149.
Dumoutier, L. et al. (Feb. 15, 2000). "Cloning and Characterization of IL-10-Related T Cell-Derived Inducible Factor (IL-TIF), a Novel Cytokine Structurally Related to IL-10 and Inducible by IL-91," The Journal of Immunology 164 (4):1814-1819.
Duncan, A.R. et al. (Apr. 21, 1988). "The Binding Site for C1q on IgG," Nature 322:738-740.
Duricova, D. et al. (2014). "Age-Related Differences In Presentation And Course Of Inflammatory Bowel Disease: An Update On The Population-Based Literature," Journal of Chrohn's and Colitis 8:1351-1361.
EBI Accession No. AWL86673. (May 26, 2018). "Streptomyces Globisporus Elongation Factor Tu," Located at URL: https://www.ebi.ac.uk/ena/data/view/AWL86673&display=text, last visited on May 31, 2018.DATABASE Geneseq [Online] May 28, 2009 (May 28, 2009), "Human IgG double chain constant region protein Seq ID:97.", retrieved from EBI accession No. GSP:AWL86673 Database accession No. AWL86673.
Eriguchi, Y. et al. (Jul. 5, 2012, e-pub. Apr. 24, 2012). "Graft-Versus-Host Disease Disrupts Intestinal Microbial Ecology by Inhibiting Paneth Cell Production of α-Defensins," Blood 120(1):223-231.
European Communication Pursuant to Article 94(3) EPC dated Jun. 15, 2018 for EP Application No. 14860161.0, filed on Jun. 7, 2016, 5 pages.
European Communication Pursuant to Article 94(3) EPC dated Nov. 28, 2016 for EP Application No. 11821115.0, filed on Aug. 30, 2011, 4 pages.
European Communication pursuant to Rules 161(2) and 162 EPC dated Aug. 22, 2016 for EP Application No. 14860301.2, filed on Nov. 6, 2014, 2 pages.
European Communication Under Rule 71(3) EPC dated Jul. 19, 2017 for EP Application No. 11821115.0, filed on Aug. 30, 2011, 5 pages.
European Extended Search Report dated Nov. 28, 2019, for Patent Application No. 17783333.2, filed Apr. 14, 2017, seven pages.

Yee, W.H. et al. (Feb. 2012, e-pub. Jan. 23, 2012). "Incidence and Timing of Presentation of Necrotizing Enterocolitis in Preterm Infants," Pediatrics 129(2):e298-304. (Abstract Only).
European Notice of Opposition to the European Patent No. EP3065777, filed Feb. 14, 2020, by opponent Strawman Limited, 63 pages.
European Office Action dated Nov. 5, 2018 for EP Application No. 14860301.2 filed, on Jun. 7, 2016, 3 pages.
European Supplementary Search Report dated Jul. 7, 2017 for EP Application No. 14860998.5, filed on Nov. 7, 2014, eight pages.
European Supplementary Search Report dated Jul. 12, 2017 for EP Application No. 14860301.2 filed, on Jun. 7, 2016, 7 pages.
European Supplementary Search Report dated Jun. 30, 2017 for EP Application No. 14860161.0, filed on Jun. 7, 2016, 7 pages.
Extended European Search Report dated Mar. 13, 2018, for EP Patent Application No. 17210060.4, filed on Dec. 22, 2017, 8 pages.
Extended European Search Report dated Oct. 10, 2014, for EP Patent Application No. 11821115.0, filed on Aug. 30, 2011, 5 pages.
Eyerich, S. et al. (Sep. 2010; e-pub. Aug. 4, 2010). "IL-17 and IL-22: Siblings, Not Twins," Trends Immunol. 31(9):354-361.
Feng, D. et al. (2012). "Interleukin-22 Ameliorates Cerulein-Induced Pancreatitis in Mice by Inhibiting the Autophagic Pathway," International Journal of Biological Sciences 8(2):249-257.
Ferrara, J. L., et al. (May 2, 2009). "Graft-Versus-Host Disease," Lancet 373:1550-1561.
Fleer, R. et al. (Oct. 1, 1991). "Stable Multicopy Vectors for High-Level Secretion of Recombinant Human Serum Albumin by *Kluyveromyces* Yeasts," Bio/Technology 9(10):968-975.
Gan, M. et al. (2006). "The Progress of Multiple Organ Dysfunction Syndrome," Medical Recapitulate 14:14. (Abstract Only).
Gao, B. (Apr. 2005). "Cytokines, STATs and Liver Disease," Cell. Mol. Immunol. 2(2):92-100.
Gao, H. et al. (Jun. 2006). "Long-Term Administration of Estradiol Decreases Expression of Hepatic Lipogenic Genes and Improves Insulin Sensitivity in ob/ob Mice: A Possible Mechanism Is through Direct Regulation of Signal Transducer and Activator of Transcription 3," Molecular Endocrinology 20(6):1287-1299.
Gavrieli, Y. et al. (Nov. 1992) "Identification Of Programmed Cell Death In Situ Via Specific Labeling Of Nuclear DNA Fragmentation," J Cell Biol. 119:493-501.
Gazzano-Santoro, H. et al. (Mar. 28, 1997). "A Non-Radioactive Complement-Dependent Cytotoxicity Assay for Anti-CD20 Monoclonal Antibody," J. Immunol. Methods 202:163-171.
Generon BioMed Holding Ltd. (Nov. 13, 2018). Generon's F-652 Shows Positive Results in "An Open Label, Cohort Dose Escalation Study to Assess the Safety and Efficacy in Patients with Alcoholic Hepatitis", located at https://www.businesswire.com/news/home/20181113005520/en/Generon%E2%80%99s-F-652-Shows-Positive-Results-%E2%80%9CAn-Open, last visited on Mar. 20, 2020, 2 pages.
Gephart, S.M. et al. (Apr. 2012) "Necrotizing Enterocolitis Risk: State Of The Science," Adv Neonatal Care 12 (2):77-87.
Gerbitz, A. et al. (Jun. 1, 2004, e-pub. Feb. 12, 2004). "Probiotic Effects on Experimental Graft-Versus-Host Disease: Let Them Eat Yogurt," Blood 103(11):4365-4367.
Gething, M.J. et al. (Oct. 22, 1981). "Cell-Surface Expression of Influenza Haemagglutinin from a Cloned DNA Copy of the RNA Gene," Nature, 293:620-625.
Gill, H.K. et al. (Jan. 21, 2006). "Non-Alcoholic Fatty Liver Disease and the Metabolic Syndrome: Effects of Weight Loss and a Review of Popular Diets. Are Low Carbohydrate Diets the Answer?" World Journal of Gastroenterology 12(3):345-353.
Glinka, A. et al. (Sep. 30, 2011, e-pub. Sep. 9, 2011). "LGR4 and LGR5 are R-spondin Receptors Mediating Wnt/β-Catenin and Wnt/PCP Signalling," EMBO Rep. 12(10):1055-1061.
Goeddel, D.V. et al. (Oct. 18, 1979). "Direct Expression in *Escherichia coli* of a DNA Sequence Coding For Human Growth Hormone," Nature 281:544-548.
Goeddel, D.V. et al. (Sep. 25, 1980). "Synthesis of Human Fibroblast Interferon by *E. coli*," Nucleic Acids Res. 8(18):4057-4074.
Good, M. et al. (Jun. 1, 2014, e-pub Apr. 17, 2014)."Lactobacillus Rhamnosus HN001 Decreases The Severity Of Necrotizing Enterocolitis

(56) References Cited

OTHER PUBLICATIONS

In Neonatal Mice And Preterm Piglets: Evidence In Mice For A Role Of TLR9," Am J Physiol Gastrointest Liver Physiol. 306(11):G1021-G1032.
Good, M. et al. (May 1, 2015). "The Role of IL-22 Signaling in the Pathogenesis of Necrotizing Enterocolitis (HUM1P.314)," The Journal of Immunology 194(Supplement 1): Abstract No. 52.39.
Graham, F.L. et al. (1977). "Characteristics of a Human Cell Line Transformed by DNA from Human Adenovirus Type 5," J. Gen Virol. 36:59-72.
Graham, F.L. et al. (Apr. 1973). "A New Technique for the Assay of Infectivity of Human Adenovirus 5 DNA," Virology 52(2):456-467.
Grattagliano, I. et al. (May 2007). "Managing Nonalcoholic Fatty Liver Disease: Recommendations for Family Physicians," Canadian Family Physician 53(5):857-863.
Greenwald, R.B. et al. (Oct. 20, 1994). "Highly Water Soluble Taxol Derivatives: 2'-Polyethyleneglycol Esters as Potential Prodrugs," Bioorg. Med.Chem. Lett. 4(20):2465-2470.
Guss, B. et al. (Jul. 1986). "Structure of the IgG-Binding Regions of Streptococcal Protein G," EMBO J. 5(7):1567-1575.
Guyer, R.L. et al. (Aug. 1976). "Immunoglobulin Binding By Mouse Intestinal Epithelial Cell Receptors," J. Immunol. 117(2):587-593.
Hanash, A. et al. (Feb. 2012). "Host-Derived IL-22 Protects Intestinal Stem Cells from GvHD," Biology of Blood and Marrow Transplantation 18(2): Abstract No. 426, S361-S362.
Hanash, A.M. (Aug. 26, 2012). "IL-22 In Epithelial Regeneration After Allogeneic Transplant," NIH Report Portfolio Online Reporting Tools, 5 pages. (Abstract Only).
Hanash, A.M. et al. (2012). "Effect of IL-22 on Intestinal Stem Cells, GVHD-related Tissue Damage, and GVL," Journal of Clinical Oncology: 6539, 1 page. (Abstract only).
Hanash, A.M. et al. (Aug. 24, 2012). "Interleukin-22 Protects Intestinal Stem Cells from Immune-mediated Tissue Damage and Regulates Sensitivity to Graft Versus Host Disease," Immunity 37(2):339-350.
Hanash, A.M. et al. (Nov. 18, 2011). "Host-Derived IL-22 Limits Graft Versus Host Disease and Protects the Intestinal Stem Cell Niche," Blood. 118(21):309, 7 pages. (Abstract Only).
Hellstrom, I. et al. (Mar. 1985). "Strong Antitumor Activities of IgG3 Antibodies to a Human Melanoma-associated Ganglioside," Proc. Natl. Acad. Sci. USA 82:1499-1502.
Hellstrom, I. et al. (Sep. 1986). "Antitumor Effects of L6, an IgG2a Antibody That Reacts With Most Human Carcinomas," Proc. Natl. Acad. Sci. USA 83:7059-7063.
Henikoff, S. et al. (Nov. 15, 1992). "Amino Acid Substitution Matrices From Protein Blocks," Proc. Nat'l Acad. Sci. USA 89:10915-10919.
Herrine, S.K. et al. (Jan. 2018). "Fatty Liver Hepatic Steatosis," Merck Manual, one page only.
Hess, B. et al. (1969). "Cooperation of Glycolytic Enzymes," Adv Enzyme Regul. 7:149-167.
Hill, G.R. et al. (May 1, 2000). "The Primacy of the Gastrointestinal Tract as a Target Organ of Acute Graft-Versus-Host Disease: Rationale for the use of Cytokine Shields in Allogeneic Bone Marrow Transplantation," Blood 95(9):2754-2759.
Hines, I.N. et al. (Aug. 2004). "Recent Advances in Alcoholic Liver Disease III. Role of the Innate Immune Response in Alcoholic Hepatitis," American Journal of Physiology—Gastrointestinal and Liver Physiology 287(2):G310-G314.
Hitzeman, R.A. et al. (Dec. 25, 1980). "Isolation and Characterization of the Yeast 3-Phosphoglycerokinase Gene (PKG) by an Immunological Screening Technique," J. Biol. Chem. 255(24):12073-12080.
Holland, J.P. (Nov. 14, 1978). "Isolation and Identification of Yeast Messenger Ribonucleic Acids Coding For Enolase, Glyceraldehyde-3-Phosphate Dehydrogenase, and Phosphoglycerate Kinase," Biochemistry 17(23):4900-4907.
Hong, F. et al. (Oct. 2004). "Interleukin 6 Alleviates Hepatic Steatosis and Ischemia/Reperfusion Injury in Mice with Fatty Liver Disease," Hepatology 40(4):933-941.
Hsiao, C.L. et al. (Aug. 1979). "High-Frequency Transformation of Yeast by Plasmids Containing the Cloned Yeast ARG4 Gene," Proc. Natl. Acad. Sci. (USA) 76(8):3829-3833.
Hua, G. et al. (Nov. 2012, e-pub. Jul. 27, 2012). "Crypt Base Columnar Stem Cells in Small Intestines of Mice are Radioresistant," Gastroenterology 143:1266-1276.
Huber, S. et al. (Nov. 8, 2012, Epub Oct. 17, 2012) "IL-22BP is regulated by the inflammasome and modulates tumorigenesis in the intestine." Nature, 491(7423):259-263.
Hwang, T.-L. (May 2009). "Potential Use of Albumin Administration in Severe Sepsis," J Chin Med Assoc 72(5):225-226.
Idusogie, E.E. et al. (2000). "Mapping of the C1q Binding Site on Rituxan, a Chimeric Antibody With a Human IgG1 Fc," J. Immunol. 164:4178-4184.
Inoue, H. et al. (Feb. 2004; e-published on Jan. 11, 2004). "Role of STAT-3 in Regulation of Hepatic Gluconeogenic Genes and Carbohydrate Metabolism In Vivo," Nat Med. 10(2):168-174. (English Abstract only).
International Diabetes Federation. (2006). "The IDF Consensus Worldwide definition of the metabolic Syndrome," 24 pages.
International Preliminary Examination Report Completed on Sep. 3, 2009 for PCT Application No. PCT/US2008/071859 filed on Aug. 1, 2008, 4 pages.
International Preliminary Report on Patentability dated Jul. 10, 2007, for International Application No. PCT/US05/28186, filed Aug. 8, 2005, four pages.
International Preliminary Report on Patentability dated Jul. 10, 2014, for International Application No. PCT/CN2012/087694, filed Dec. 27, 2012, 21 pages (with attached English translation of the Written Opinion of the International Searching Authority).
International Preliminary Report on Patentability dated Jul. 21, 2011, for International Application No. PCT/US2010/20673, filed Jan. 11, 2010, six pages.
International Preliminary Report on Patentability dated Mar. 14, 2013, for International Application No. PCT/CN2011/079124, filed Aug. 30, 2011, fourteen pages (with attached English translation).
International Preliminary Report on Patentability dated May 10, 2016 for International Application No. PCT/CN2014/090520, filed on Nov. 6, 2014, six pages.
International Preliminary Report on Patentability dated May 10, 2016 for International Application No. PCT/US2014/064655, filed on Nov. 7, 2014, eleven pages.
International Preliminary Report on Patentability dated May 19, 2016, for International Application No. PCT/CN2014/090519, filed Nov. 6, 2014, seven pages.
International Preliminary Report on Patentability dated Oct. 25, 2018 for PCT Application No. PCT/US2017/027806 filed on Apr. 14, 2017, 7 pages.
International Search Report and Written Opinion dated Jun. 23, 2017 for PCT Application No. PCT/US2017/027806, filed on Apr. 14, 2017, 12 pages.
International Search Report and Written Opinion dated Mar. 27, 2015 for PCT Application No. PCT/US2014/64655, filed on Nov. 7, 2014, 16 pages.
International Search Report dated Mar. 9, 2010, for International Application No. PCT/US10/20673, filed Jan. 11, 2010, three pages.
International Search Report dated May 3, 2006, for International Application No. PCT/US05/28186, filed Aug. 8, 2005, one page.
International Search Report dated Nov. 26, 2008, for International Application No. PCT/US08/71859, filed Aug. 1, 2008, one page.
International Search Report dated Apr. 18, 2013, for PCT Patent Application No. PCT/CN2012/087694, filed on Dec. 27, 2012, 4 pages.
International Search Report dated Dec. 8, 2011 for PCT Patent Application No. PCT/CN2011/079124, filed on Aug. 30, 2011, 4 pages.
International Search Report dated Feb. 10, 2015 for International Application No. PCT/CN2014/090520 filed on Nov. 6, 2014, 5 pages.

(56) References Cited

OTHER PUBLICATIONS

International Search Report dated Jan. 30, 2015 for PCT Application No. PCT/CN2014/090519 filed Nov. 6, 2014, 6 pages.
Japanese Notice of Reasons for Rejection dated Jul. 24, 2018 for JP Application No. 2016-550931 filed on May 5, 2016, 6 pages.
Japanese Office Action dated Mar. 12, 2019 for JP Application No. 2016-550931 filed on May 5, 2016, 7 pages.
Jenq, R.R. et al. (Mar. 2010; e-published on Feb. 19, 2010). "Allogeneic Haematopoietic Stem Cell Transplantation: Individualized Stem Cell and Immune Therapy of Cancer," Nat Rev Cancer 10(3)213-220; pp. 1-10 (advance publication).
Jenq, R.R. et al. (May 2012, e-pub. Apr. 30, 2012). "Regulation of Intestinal Inflammation by Microbiota Following Allogeneic Bone Marrow Transplantation," The Journal of Experimental Medicine 209(5):903-911.
Jiang, R. et al. (Dec. 2013). "IL-22 Is Related To Development Of Human Colon Cancer By Activation Of STAT3," BMC Cancer 13(1):59.
Jiang, R. et al. (Sep. 2, 2011). "Interleukin-22 Promotes Human Hepatocellular Carcinoma by Activation of STAT3," Hepatology 54(3):900-909.
Johnson, O.L. et al. (Jul. 1996). "A Month-Long Effect from a Single Injection of Microencapsulated Human Growth Hormone," Nature Medicine 2(7):795-799.
Jones, B.C. et al. (Apr. 1, 2008; e-pub. Mar. 21, 2008). "Crystallization and Preliminary X-Ray Diffraction Analysis of Human IL-22 Bound to the Extracellular IL-22R1 Chain," Acta Crystall. Sect. F. Structure Biol. Cryst. Commun. 64 (Pt. 4):266-269.
Jones, E.W. (Jan. 1977). "Proteinase Mutants of *Saccharomyces cerevisiae*," Genetics 85(1):23-33.
Kabiri, Z. et al. (Jun. 2014). "Stroma Provides an Intestinal Stem Cell Niche in the Absence of Epithelial Wnts," Development 141:2206-2215.
Kappel, L.W. et al. (Jan. 22, 2009, e-pub. Oct. 17, 2008). "IL-17 Contributes to CD4-Mediated Graft-Versus-Host Disease," Blood 113(4):945-952.
Kelly, J.M. et al. (Feb. 1985). "Transformation of Aspergillus niger by the amdS Gene of *Aspergillus nidulans*," EMBO J. 4(2):475-479.
Keown, W.A. et al. (1990). "Methods for Introducing DNA into Mammalian Cells," Methods in Enzymology 185:527-537.
Killen, J.A. et al. (Nov. 1, 1984). "Specific Killing Of Lymphocytes That Cause Experimental Autoimmune Myasthenia Gravis By Ricin Toxin-Acetylcholine Receptor Conjugates," J. Immunol. 133(5):2549-2553.
Kingsman, A.J. et al. (Oct. 1979). "Replication in *Saccharomyces cerevisiae* of Plasmid pBR313 Carrying DNA from the Yeast trpl Region," Gene 7(2):141-152.
Klöppel, G. et al. (1991). "Chronic Pancreatitis: Evolution of the Disease," Hepato-gastroenterology 38(5):408-412.
Knaus, W.A. et al. (Dec. 1985) "Prognosis in Acute Organ-System Failure," Ann. Surg. 202(6):685-693.
Kolls, J. K. et al. (Nov. 2008). "Cytokine-Mediated Regulation of Antimicrobial Proteins," Nat Rev Immunol 8(11):829-835.
Kotenko, S.V. et al. (Sep. 8, 1995). "Interaction Between the Components of the Interferon γ Receptor Complex," J. Biol. Chem. 270(36):20915-20921.
Kreymborg, K. et al. (Dec. 2007). "IL-22 is Expressed by Th17 Cells in an IL-23-Dependent Fashion, but Not Required for the Development of Autoimmune Encephalomyelitis," J Immunol 179:8098-8104.
Krijanovski, O.I. et al. (Jul. 15, 1999). "Keratinocyte Growth Factor Separates Graft-Versus-Leukemia Effects From Graft-Versus-Host Disease," Blood 94(2): 825-831.
Krivtsov, A.V. et al. (Aug. 2006, e-pub. Jul. 16, 2006). "Transformation from Committed Progenitor to Leukaemia Stem Cell Initiated by MLL-AF9," Nature. 442(7104):818-822.
Kuroiwa, T. et al. (Jun. 2001). "Hepatocyte Growth Factor Ameliorates Acute Graft-Versus-Host Disease and Promotes Hematopoietic Function," J. Clin. Invest 107:1365-1373.

Lee, W.-C. at al. (Jan. 2010). "Palmatine Attenuates D-Galactosamine/Lipopolysaccharide-Induced Fulminant Hepatic Failure In Mice," Food Chem Toxicol 48(1):222-228.
Lei, K. et al. (May 19, 1995). "Structure-Function Analysis of Human Glucose-6-Phosphatese, the Enzyme Deficient in Glycogen Storage Disease Type 1a*," The Journal of Biological Chemistry 270(20):11882-11886.
Levine, J.E. et al. (Aug. 22, 2013, e-pub. Jun. 12, 2013). "Low Paneth Cell Numbers at Onset of Gastrointestinal Graft-Versus-Host Disease Identify Patients at High Risk for Nonrelapse Mortality," Blood 122(8):1505-1509.
Lewis, D.H. (1990). "Controlled Release of Bioactive Agents From Lactide/Glycolide Polymer," in Chapter 1 of Biodegradable Polymers as Drug Delivery Systems, Chasin, M. (ed.) et al., Marcel Dekker Inc. New York, 1990, pp. 1-41, 52 pages.
Li, H. et al. (2016). "Gastrointestinal Stem Cells in Health and Disease: From Flies to Humans," Dis Model Mech 9:487-499.
Li, Q. (Sep. 2003). "Research Development of Interleukin-22," Chinese J. of Cancer Biotherapy 10(3):226-228 (Translation of Abstract Only).
Lieber, C.S. et al. (Mar. 1966). "Study of Agents for the Prevention of the Fatty Liver Produced by Prolonged Alcohol Intake," Gastroenterology 50(3):316-322.
Lieber, C.S. et al. (Oct. 1989). "Experimental Methods Of Ethanol Administration," Hepatology 10(4):501-510.
Lindemans, C. et al. (2014). "IL-22 Administration Protects Intestinal Stem Cells from Gvhd," Biol Blood Marrow Transplant 20(2): Supp. SUPPL. 1, Abstract No. 49, 553-554.
Lindmark, R. et al. (1983). "Binding of Immunoglobulins to Protein A and Immunoglobulin Levels in Mammalian Sera," J. Immunol. Meth. 62:1-13.
Longman, R. S. et al. (Jul. 2014, e-pub. Jul. 14, 2014). "CX3CR1+ Mononuclear Phagocytes Support Colitis-Associated Innate Lymphoid Cell Production of IL-22," J Exp Med 211:1571-1583.
Louvencourt, L.D. et al. (May 1983). "Transformation of Kluyveromyces Lactis by Killer Plasmid DNA," J. Bacterial. 154(2):737-742.
Low, S.C. et al. (Jul. 2005). "Oral and pulmonary delivery of FSH-Fc fusion proteins via neonatal Fc receptor-mediated transcytosis," Human Reproduction 20(7):1805-1813.
Mansour, S.L. et al. (Nov. 24, 1988). "Disruption of the Proto-Oncogene Int-2 in Mouse Embryo-Derived Stem Cells: A General Strategy For Targeting Mutations to Non-Selectable Genes," Nature 336:348-352.
Mantei, N. et al. (Sep. 6, 1979). "Rabbit β-globin mRNA Production in Mouse L Cells Transformed with Cloned Rabbit β-Globin Chromosomal DNA," Nature 281:40-46.
Marchesini, G. et al. (Aug. 2001). "Nonalcoholic Fatty Liver Disease," Diabetes 50(8):1844-1850.
Mather, J.P. (Aug. 1980) "Establishment and Characterization of Two Distinct Mouse Testicular Epithelial Cell Lines,"Biol. Reprod. 23(1):243-252.
Matsusue, K. et al. (Mar. 2003). "Liver-Specific Disruption Of Pparβ In Lepiin-Deficient Mice Improves Fatty Liver But Aggravates Diabetic Phenotyps," J. Clin. Invest. 111(5):737-747.
Matthews, J. R. et al. (Dec. 2011). "Absolute Requirement for STAT3 Function in Small-Intestine Crypt Stem Cell Survival," Cell Death Differ 18:1934-1943.
Mavrelis, P.G. et al. (1983). "Hepatic Free Fatty Acids in Alcoholic Liver Disease and Morbid Obesity," Hepatology 3(2):226-231.
Max Bayard, M.D. et al. (Jun. 1, 2006). "Nonalcoholic Fatty Liver Disease," American Family Physician 73(11):1961-1968.
Medema, J.P. et al. (Jun. 16, 2011). "Microenvironmental Regulation of Stem Cells in Intestinal Homeostasis and Cancer," Nature 474:318-326.
Mertelsmann, A.M. et al. (2013). "IL-22 Administration Decreases Intestinal Gvhd Pathology, Increases Intestinal Stem Cell Recovery, and Enhances Immune Reconstruction Following Allogeneic Hematopietic Transplantation," Blood 122(22), Abstract 290, 3 pages.
Metcalfe, C et al. (Feb. 6, 2014, e-pub Dec. 12, 2013). "Lgr5+ Stem Cells are Indispensable for Radiation-Induced Intestinal Regeneration," Cell Stem Cell 14:149-159.

(56) References Cited

OTHER PUBLICATIONS

Mordenti, J. et al. (1989). "The Use of Interspecies Scaling in Toxicokinetics," Chapter 4 in Toxicokinetics and New Drug Development, Yacobi A. ed. et al.; Pergamon Press, New York, pp. 42-96.

Morris, H.G. (Jan. 1985). "Mechanisms of Action and Therapeutic Role of Corticosteroids in Asthma," Allergy Clin. Immunol. 75(1 Pt 1):1-13.

Morris, S. A. et al. (Aug. 14, 2014). "Dissecting Engineered Cell Types and Enhancing Cell Fate Conversion via CellNet," Cell 158:889-902.

Mortele, K.J. et al. (Nov. 2004). "A Modified CT Severity Index for Evaluating Acute Pancreatitis: Improved Correlation With Patient Outcome," American Journal of Roentgenology 183:1261-1265.

Muhl, H. et al. (Jun. 2013). "IL-22 in Tissue-Protective Therapy," Br. J. Pharmacol. 169(4): 761-771.

Munneke, J. M. et al. (Jul. 31, 2014). "Activated Innate Lymphoid Cells are Associated with a Reduced Susceptibility to Graft-Versus-Host Disease," Blood 124:812-821.

Nagalakshmi, M.L. et al. (May 2004). "Interleukin-22 Activates STAT3 and Induces IL-10 by Colon Epithelial Cells," International Immunopharmacology 4(5):679-691.

Neu, J. et al. (Jan. 20, 2011). "Necrotizing Enterocolitis," N Engl J Med. 364(3):255-264.

NIH (Jan. 14, 2016). "Use of F-652 in Patients With Alcoholic Hepatitis (TREAT 008)," ClinicalTrials.gov, No. NCT02655510, 8 pages, retrieved from https://clinicaltrials.gov/ct2/show/.

NIH (Jun. 30, 2018). "RePORTER Frequently Asked Questions (FAQ)," NIH Research Portfolio Online Reporting Tools (RePORT), 2 pages.

Nilson, B.H.K. at al. (Feb. 5, 1992). "Protein L From *Peptostreptococcus magnus* Binds to the Kappa Light Chain Variable Domain," J. Biol. Chem. 267(4):2234-2239.

Oki, K. et al. (2016, e-pub. Nov. 28, 2016). "Comprehensive Analysis Of The Fecal Microbiota Of Healthy Japanese Adults Reveals A New Bacterial Lineage Associated With A Phenotype Characterized By A High Frequency Of Bowel Movements And A Lean Body Type," BMC Microbiology 16:284, 13 pages.

Pan, H. et al. (Feb. 2004). "Hydrodynamic Gene Delivery of Interleukin-22 Protects the Mouse Liver from Concanavalin A-, Carbon Tetrachloride-, and Fas Ligand-Induced Injury Via Activation of STAT3," Cell. Mol. Immunol. 1(1):43-49.

Papathanassoglou, E.D.E. et al. (Sep. 2008). "Multiple Organ Dysfunction Syndrome Pathogenesis And Care: A Complex Systems' Theory Perspective," Nursing in Critical Care 13(5):249-259. (Abstract Only).

Parks, O.B. et al. (Jan. 13, 2016). "Interleukin-22 Signaling in the Regulation of Intestinal Health and Disease," Frontiers in Cell and Developmental Biology 3:1-13(Article 85).

Pearson, C. et al. (Jun. 2012; e-published on May 10, 2012). "Lymphoid Microenvironments and Innate Lymphoid Cells in the Gut," Trends Immunol 33(6):289-296.

Peery, A. F. et al. (Nov. 2012, e-pub. Aug. 8, 2012). "Burden of Gastrointestinal Disease in the United States—2012 Update," Gastroenterology 143:1179-1187.

Petkova, S.B. et al. (Oct. 31, 2006). "Enhanced Half-Life of Genetically Engineered Human IgG1 Antibodies in a Humanized FcRn Mouse Model: Potential Application in Humorally Mediated Autoimmune Disease," Int'l. Immunol. 18(12):1759-1769.

Pickert, G. et al. (Jul. 2009, e-pub. Jun. 29, 2009). "STAT3 Links IL-22 Signaling in Intestinal Epithelial Cells to Mucosal Wound Healing," J. Exp. Med. 206:1465-1472.

Ponce, D.M. et al. (Jun. 2013). "Graft-versus-host Disease After Double-Unit Cord Blood Transplantation Has Unique Features and an Association with Engrafting Unit-Recipient HLA-match," Biol Blood Marrow Transplant 19(6):904-911.

Qiu, Z. et al. (Jan. 2006). "Fibronectin Prevents D-Galactosamine/Lipopolysaccharide-Induced Lethal Hepatic Failure In Mice," Shock 25(1):80-87.

Quinlan, G.J. et al. (Oct. 1998). "Administration Of Albumin To Patients With Sepsis Syndrome: A Possible Beneficial Role In Plasma Thiol Repletion," Clinical Science 95:459-465.

R&D Systems, Inc. (2021). "Quantikine® ELISA Human IL-10 Immunoassay," Product Datasheets, located at: https://resources.rndsystems.com/pdfs/datasheets/d1000b.pdf, last visited on Mar. 20, 2020, 16 pages.

Raag, R. et al. (Jan. 1995). "Single-chain Fvs," The FASEB Journal 9:73-80.

Radaeva, S. et al. (May 2004). "Interleukin 22 (IL-22) Plays a Protective Role in T Cell-Mediated Murine Hepatitis: IL-22 is a Survival Factor for Hepatocytes Via STAT3 Activation," Hepatology 39(5):1332-1342.

Rahman, T. M. (Apr. 2000). "Animal Models Of Acute Hepatic Failure," International Journal Of Experimental Pathology 81(2):145-157.

Ramakrishnan, S. et al. (Jan. 1984). "Comparison of the Selective Cytotoxic Effects of Immunotoxins Containing Ricin A Chain or Pokeweed Antiviral Protein and Anti-Thy 1.1 Monoclonal Antibodies," Cancer Res. 44:201-208.

Ramaswamy, S. et al. (2017). "Antinociceptive and Immunosuppressive Effect of Opioids in an Acute Postoperative SettingL An Evidence-Based Review," BJA Education 17(3):105-110.

Ravetch, J.V. et al. (1991). "Fc Receptors," Annu. Rev. Immunol. 9:457-492.

Reagan-Shaw, S. et al. (Oct. 17, 2007). "Dose Translation From Animal To Human Studies Revisited," The FASEB Journal 22(3):659-661.

Remick, D.G. et al. (May 2007). "Pathophysiology of Sepsis", Am J Pathol 170(5):1435-1444.

Rendon, J.L. et al. (Sep. 2012). "Th17 Cells: Critical Mediators Of Host Responses To Burn Injury And Sepsis," Journal of Leukocyte Biology 92(3):529-538.

Richter, W.F. et al. (Sep. 2012). "Mechanistic Determinants of Biotherapeutics Absorption Following SC Administration," The AAPS Journal 14(3):559-570.

Riley, P. et al. (Dec. 2007; e-published on May 4, 2007). "A Growing Burden: The Pathogenesis, Investigation and Management of Non-Alcoholic Fatty Liver Disease," Journal of Clinical Pathology 60(12):1384-1391.

Ritsma, L. et al. (Mar. 20, 2014, e-pub. Feb. 16, 2014). "Intestinal Crypt Homeostasis Revealed at Single-Stem-Cell Level by In Vivo Live Imaging," Nature 507:362-365.

Rutz, S. et al. (Dec. 2014). "The IL-20 Subfamily Of Cytokines—From Host Defence To Tissue Homeostasis," Immunology 14:783-795.

Sabat, R. et al. (Jan. 2014). "Therapeutic Opportunities of the IL-22-IL-22R1 System," Nat Rev Drug Discov 13:21-38.

Sale, G.E. (Mar. 1996). "Does Graft-Versus-Host Disease Attack Epithelial Stem Cells?," Mol Med Today 2(3):114-119.

Sambrook, J. at al. (1989). Molecular Cloning—A Laboratory Manual, 2nd Edition, Maniatis, T.(ed.) et al., Cold Spring Harbor Laboratory Press, New York, NY pp. v-xxxii, 28 pages, (Table of Contents only).

Sanos, S. L. et al. (Mar. 2013, e-pub. Jan. 29, 2013) "Innate Lymphoid Cells: from Border Protection to the Initiation of Inflammatory Diseases," Immunol Cell Biol 91(3):215-224.

Sato, T. et al. (Jan. 20, 2011, e-pub. Nov. 28, 2010). "Paneth Cells Constitute the Niche for Lgr5 Stem Cells in Intestinal Crypts," Nature 469:415-418.

Sato, T. et al. (May 14, 2009; e-pub. Mar. 29, 2009). "Single Lgr5 Stem Cells Build Crypt-Villus Structures in Vitro without a Mesenchymal Niche," Nature 459:262-265.

Satoh-Takayama, N. et al. (Dec. 19, 2008). "Microbial Flora Drives Interleukin 22 Production in Intestinal NKp46+ Cells that Provide Innate Mucosal Immune Defense," Immunity 29(6):958-970.

Sawa, S. et al. (Apr. 2011, e-pub. Feb. 20, 2011). "RORβt+ Innate Lymphoid Cells Regulate Intestinal Homeostasis by Integrating Negative Signals from the Symbiotic Microbiota," Nat Immunol 12:320-326, 33 pages.

Scheraga, H.A. (Jan. 1992). "Predicting Three-Dimensional Structures Of Oligopeptides," Reviews in Computational Chemistry 3:73-142. (Abstract only).

(56) References Cited

OTHER PUBLICATIONS

Schmidt, J. et al. (Jan. 1992). "A Better Model of Acute Pancreatitis for Evaluating Therapy," Annals of Surgery 215(1):44-56.
Schnabl, K.L. et al. (Apr. 14, 2008) "Necrotizing Enterocolitis: A Multifactorial Disease With No Cure," World J Gastroenterol. 14(14):2142-2161.
Schroeder, M. A., et al. (May 2011). "Mouse Models of Graft-Versus-Host Disease: Advances and Limitations," Dis Model Mech 4(3):318-333.
Sekikawa, A. et al. (Mar. 2010, e-pub. Jan. 11, 2010). "Involvement of the IL-22/REG Lα Axis in Ulcerative Colitis," Lab Invest 90(3):496-505.
Shaw, C.H. et.al. (Sep. 1983). "A General Method for the Transfer of Cloned Genes to Plant Cells," Gene 23(3):315-330.
Shields, R.L. et al. (Mar. 2, 2001). "High Resolution Mapping of the Binding Site on Human IgG1 for FcβRI, FcβRII. FcβRIII, and FcRn and Design of IgG1 Variants With Improved Binding to the FcβR," J. Biol.Chem. 276(9):6591-6604.
Shin, J.-W et al. (2010). "Interpretation of Animal Dose and Human Equivalent Dose for Drug Development," The Journal of Korean Oriental Medicine 31(3):1-7.
Shlomchik, E.D. (May 2007). "Graft-Versus-Host Disease," Nat. Rev. Immunol. 7(5):340-352.
Simons, B.D. et al. (Nov. 2011, e-pub. Jul. 20, 2011). "Stem Cell Self-Renewal in Intestinal Crypt," Exp Cell Res. 317(19):2719-2724.
Sodhi, C.P. et al. (Sep. 2012, E-pub Jul. 13, 2012) "Intestinal Epithelial Toll-Like Receptor 4 Regulates Goblet Cell Development And Is Required For Necrotizing Enterocolitis In Mice," Gastroenterology 143(3):708-718.
Sonnenberg, G.F. et al. (Jan. 2011, e-pub. Dec. 30, 2010). "CD4(+) Lymphoid Tissue-Inducer Cells Promote Innate Immunity in the Gut," Immunity 34(1):122-134.
Sonnenberg, G.F. et al. (May 2011, e-pub. Apr. 19, 2011). "Border Patrol: Regulation of Immunity, Inflammation and Tissue Homeostasis at Barrier Surfaces by IL-22," Nat Immunol. 12(5):383-390.
Spits, H. et al. (Feb. 2013; e-published on Jan. 7, 2013). "Innate Lymphoid Cells—A Proposal for Uniform Nomenclature," Nat Rev Immunol 13:145-149, advance online publication pp. 1-5.
Sreekrishna, K. et al. (1988). "High Level Expression of Heterologous Proteins in Methylotrophic Yeast *Pichia pastoris*," J. Basic Microbial. 28(4):265-278.
Stinchcomb, D.T. et al. (Nov. 1, 1979). "Isolation and Characterisation of a Yeast Chromosomal Replicator," Nature 282:39-43.
Stubbs, M.C. et al. (Jan. 2008, e-pub. Sep. 13, 2007). "MLL-AF9 and FLT3 Cooperation in Acute Myelogenous Leukemia: Development of a Model for Rapid Therapeutic Assessment," Leukemia 22:66-77.
Sugimoto, K. et al. (Feb. 2008). "IL-22 Ameliorates Intestinal Inflammation in a Mouse Model of Ulcerative Colitis," The Journal of Clinical Investigation 118(2):534-544.
Takashima, S. et al. (Feb. 14, 2011, e-pub. Jan. 31, 2011). "The Wnt Agonist R-Spondin1 Regulates Systemic Graft-Versus-Host Disease by Protecting Intestinal Stem Cells," J Exp Med 208(2):285-294.
Takatsuka, H. et al. (2003). "Intestinal Graft-Versus-Host Disease: Mechanisms and Management," Drugs 63(1):1-15. (Abstract Only).
Talbot, I. et al. (2006). "Graft-Versus-Host Disease," Biopsy Pathology in Colorectal Disease, 2Ed: Chapter 11.6, 192-194.
Tappe, D. et al. (2016, e-pub. Dec. 24, 2015). "Cytokine Kinetics Of Zika Virus-Infected Patients From Acute To Reconvalescent Phase," Med Microbiol Immunol. 205:269-273.
Tilburn, J. et.al. (Dec. 1983). "Transformation by Integration in Aspergillus nidulans," Gene 26(2-3):205-221.
Tschemper, G. et al. (Jul. 1980). "Sequence of a Yeast DNA Fragment Containing a Chromosomal Replicator and the TRP1 Gene," Gene 10(2):157-166.
Tsunoda, S. et al. (May 1995). "Characterization of PEG-IL-6 and its Thrombopoetic Activity in Vivo," Drug Delivery System 10(3):175-180; (with English introduction).

Tymoczko, J.L. et al. (Dec. 23, 2011). "Membranes Define the Cell and Carry out Cellular Functions," Chapter 1.4 in Biochemistry A Short Course, Second Edition, W.H. Freeman and Company, New York, pp. 13-15, 5 pages.
U.S. Appl. No. 16/724,491, filed Dec. 23, 2019, by Marcel et al. (Copy not submitted herewith pursuant to the waiver of 37 C.F.R. § 1.98 (a)(2)(iii) issued by the Office on Sep. 21, 2004.).
Ueki, K. et al. (Jul. 13, 2004). "Central Role of Suppressors 0f Cytokine Signaling Proteins in Hepatic Steatosis, Insulin Resistance, and the Metabolic Syndrome in the Mouse," PNAS 101(28):10422-10427.
Urlaub, G. et al. (Jul. 1980). "Isolation of Chinese Hamster Cell Mutants Deficient in Dihydrofolate Reductase Activity," Proc. Natl. Acad. Sci. USA 77(7):4216-4220.
Van Den Berg, J.A. et al. (Feb. 1990). "Kluyveromyces as a Host For Heterologous Gene Expression: Expression and Secretion of Prochymosin," Bio/Technology 8(2):135-139.
Van Solingen, P. et al. (May 1977). "Fusion of Yeast Spheroplasts,"Journal of Bacteriology 130(2):946-947.
Velardi, E. et al. (Sep.-Oct. 2013, e-pub Oct. 8, 2013) "Clinical Strategies To Enhance Thymic Recovery After Allogeneic Hematopoietic Stem Cell Transplantation," Immunol Lett. 155(1-2):31-35.
Vitetta, E.S. et al. (Nov. 20, 1987). "Redesigning Nature's Poisons to Create Anti-Tumor Reagents," Science 238:1098-1104.
Walker, C. R. et al. (Dec. 17, 2013). "Intestinal Intraepithelial Lymphocyte-Enterocyte Crosstalk Regulates Production of Bactericidal Angiogenin 4 by Paneth Cells upon Microbial Challenge," PloS One 8(12):e84553 pp. 1-16.
Wang, F. et al. (Aug. 2013, e-pub. May 2, 2013). "Isolation and Characterization of Intestinal Stem Cells Based on Surface Marker Combinations and Colony-Formation Assay," Gastroenterology 145:383-395.
Weber, G.F. et al. (Apr. 2007, e-pub Jan. 29, 2007). "Inhibition Of Interleukin-22 Attenuates Bacterial Load And Organ Failure During Acute Polymicrobial Sepsis," Infection and Immunity 75(4):1690-1697.
WHO. (Jul. 2015). "What is Hepatitis?" located at http://www.who.int/features/qa/76/en/, last visited on Jan. 15, 2016, three pages.
Wingard, J.R. et al. (Jun. 1, 2011). "Long-Term Survival and Late Deaths after Allogeneic Hematopoietic Cell Transplantation," J. Clin. Oncol. 29(16):2230-2239.
Witte, E. et al. (Oct. 2010, e-published on Sep. 25, 2010). "Interleukin-22: A Cytokine Produced by T, NK and NKT Cell Subsets, with Importance in the Innate Immune Defense and Tissue Protection," Cytokine Growth Factor Rev. 21(5):365-379.
Wolk, K. (Oct. 2006). "Interleukin-22: A Novel T- And NK-Cell Derived Cytokine That Regulates The Biology Of Tissue Cells," Cytokine & Growth Factor Reviews 17(5):367-380. (Abstract Only).
Wolk, K. et al. (Aug. 2004). "IL-22 Increases the Innate Immunity of Tissues," Immunity 21(2):241-254.
Wolk, K. et al. (Jun. 2002). "Cutting Edge: Immune Cells as Sources and Targets of the IL-10 Family Members?," Journal of Immunology 168(11):5397-5402.
Wolk, K. et al. (May 2006). "IL-22 Regulates the Expression of Genes Responsible for Antimicrobial Defense, Cellular Differentiation, and Mobility in Keratinocytes: A Potential Role in Psoriasis," Eur J Immunol. 36:1309-1323.
Written Opinion of the International Searching Authority dated Mar. 9, 2010, for International Application No. PCT/US10/20673, filed Jan. 11, 2010, four pages.
Written Opinion of the International Searching Authority dated May 3, 2006, for International Application No. PCT/US05/28186, filed Aug. 8, 2005, three pages.
Written Opinion of the International Searching Authority dated Apr. 18, 2013 for PCT Patent Application No. PCT/CN2012/087694, filed on Dec. 27, 2012, 11 pages.
Written Opinion of the International Searching Authority dated Dec. 8, 2011 for PCT Patent Application No. PCT/CN2011/079124, filed on Aug. 30, 2011, 7 pages.
Written Opinion of the International Searching Authority dated Feb. 10, 2015 for International Application No. PCT/CN2014/090520 filed on Nov. 6, 2014, 4 pages.

(56) References Cited

OTHER PUBLICATIONS

Written Opinion of the International Searching Authority dated Jan. 30, 2015 for PCT Application No. PCT/CN2014/090519 filed Nov. 6, 2014, 5 pages.
Written Opinion of the International Searching Authority dated Nov. 26, 2008 for PCT Application No. PCT/US2008/071859 filed on Aug. 1, 2008, 5 pages.
Wu, C. et al. (Nov. 2007; e-pub. Oct. 14, 2007). "Simultaneous Targeting of Multiple Disease Mediators by a Dual-Variable-Domain Immunoglobulin," Nat. Biotechnol. 25(11):1290-1297.
Xie, M.H. et al. (Oct. 6, 2000; e-pub. Jun. 29, 2000). "Interleukin (IL)-22, a novel human cytokine that signals through the interferon receptor-related proteins CRF2-4 and IL-22R," J. Biol. Chem. 275(40):31335-31339.
Xing, W. et al. (Nov. 2011, e-pub Aug. 16, 2011). "Hepatoprotective Effects Of IL-22 On Fulminant Hepatic Failure Induced By D-Galactosamine And Lipopolysaccharide In Mice," Cytokine 56(2):174-179. (Abstract Only).
Yamada, A. et al. (Feb. 21, 2016). "Role of Regulatory T Cell in the Pathogenesis of Inflammatory Bowel Disease," World J Gastroenterol 22(7):2195-2205.
Yamaguchi, K. et al. (Jun. 2007). "Inhibiting Triglyceride Synthesis Improves Hepatic Steatosis but Exacerbates Liver Damage and Fibrosis in Obese Mice with Nonalcoholic Steatohepatitis," Hepatology 45(6):1366-1374.
Yang, L. et al. (Aug. 2010; e-published on Apr. 21, 2010). "Amelioration of High Fat Diet Induced Liver Lipogenesis and Hepatic Steatosis by Interleukin-22," Journal of Hepatology 53(2):339-347.
Yang, R. et al. (Nov. 2012). "MR Imaging of Acute Pancreatitis: Correlation of Abdominal Wall Edema with Severity Scores," European Journal of Radiology 81(11):3041-3047.
Yasuda. (1993). Biomedicine and Therapeutics 27(10):1221-1223. (English translation of the Introduction only).
Yelton, M.M. et al. (Mar. 1, 1984). "Transformation of Aspergillus nidulans by Using a trpC Plasmid," Proc. Natl. Acad. Sci. USA 81(5):1470-1474.
Yokoyama, W.M. (Mar. 2006) "How Do Natural Killer Cells Find Self to Achieve Tolerance?" Immunity. 24(3):249-257.
You, M. et al. (Jul. 2004). "Recent Advances in Alcoholic Liver Disease—II. Minireview: Molecular Mechanisms of Alcoholic Fatty Liver," Am J. Gastrointest Liver Physiol. 287:GI-G6.
Youdim, A. et al. (Jan. 2018). "Metabolic Syndrome," Merck Manual, 4 pages.
Yui, S. et al. (Apr. 2012; e-published on Mar. 11, 2012). "Functional Engraftment of Colon Epithelium Expanded in Vitro from a Single Adult Lgr5+ Stem Cell," Nat Med 18(4):618-624.
Zamecnik, P.C. et al. (Jun. 1, 1986). "Inhibition of Replication and Expression of Human T-Cell Lymphotropic Virus Type III in Cultured Cells by Exogenous Synthetic Oligonucleotides Complementary to Viral RNA," Proc. Natl. Acad. Sci. USA 83(12):4143-4146.
Zenewicz, L.A. et al. (2011). "Recent Advances in IL-22 Biology," International Immunol. 23(3):159-163.
Zenewicz, L.A. et al. (Dec. 2008). "Innate and Adaptive Interleukin-22 Protects Mice from Inflammatory Bowel Disease," Immunity 29(6)947-957.
Zenewicz, L.A. et al. (Oct. 2007, e-pub. Oct. 4, 2007). "Interleukin-22 but Not Interleukin-17 Provides Protection to Hepatocytes during Acute Liver Inflammation," Immunity 27:647-659.
Zhang, Y. et al. (Aug. 2010). "Solid Organ Translplant-Associated Acute Graft-Versus-Host Disease," Arch Pathol Lab Med. 134:1220-1224.
Zhao, K. et al. (Sep. 2014). "Interleukin-22 Aggravates Murine Acute Graft-Versus-Host Disease by Expanding Effector T Cell and Reducing Regulatory T Cell," J Interferon Cytokine Res 34:707-715.
Zheng, X.X. (May 15, 1995). "Administration of Noncytolytic IL-10/Fc In Murine Models Of Lipopolysaccharide-Induced Septic Shock and Allogeneic Islet Transplantation," J. Immunol. 154:5590-5600.

Zheng, Y. et al. (Feb. 8, 2007, e-pub. Dec. 24, 2006). "Interleukin-22, a TH17 Cytokine, Mediates IL-23-Induced Dermal Inflammation and Acanthosis," Nature 445:648-651.
Zheng, Y. et al. (Mar. 2008, e-pub. Feb. 10, 2008). "Interleukin-22 Mediates Early Host Defense Against Attaching and Effacing Bacterial Pathogens," Nat Med 14:282-289.
Zhou, W. J. et al. (Sep. 5, 2013). "Induction of Intestinal Stem Cells by R-Spondin 1 and Slit2 Augments Chemoradioprotection," Nature 501:107-111.
Zhu, H. et al. (Nov. 12, 2004). "STAT3 Induces Anti-Hepatitis C Viral Activity in Liver Cells," Biochem. Biophys. Res. Commun. 324(2):518-528.
Zhu, Q. et al. (Nov. 2008). "Expression of rhEPO-L-Fc Fusion Protein and Analysis of its Bioactivity and Pharmacokinetics," Sheng Wu Gong Cheng Xue Bao 24(11):1874-1879 (English Abstract Only).
Arora, P. et al. (2019). "[P21] A Randomized, Multiple-Dose Study of Subcutaneous UTTR1147A (IL-22Fc) in Patients with Neuropathic, Non-Healing Diabetic Foot Ulcers (DFUs)," Journal of Diabetes Science and Technology 14(3):632.
Carlson, M.J. et al. (Feb. 5, 2009, e-pub Oct. 28, 2008). "In vitro-Differentiated TH17 Cells Mediate Lethal Acute Graft-Versus-Host Disease With Severe Cutaneous And Pulmonary Pathologic Manifestations," Blood. 113(6):1365-1374.
Declaration of Dr. Alan Hanash filed for Opposition in European Patent No. EP3065777, dated Sep. 3, 2020, 9 pages.
Ferrara, J. L. (Oct. 1993). "Cytokine Dysregulation As A Mechanism Of Graft Versus Host Disease," Curr Opin Immunol. 5(5):794-799.
Gao, B. et al. (Jul. 2019, e-pub Jun. 19, 2018). "Interleukin-22 From Bench To Bedside: A Promising Drug For Epithelial Repair," Cellular & Molecular Immunology 16(7):666-667.
Hale, L.P. et al. (Mar. 10, 2008). "Treatment Of Experimental Colitis In Mice With LMP-420, An Inhibitor Of TNF Transcription," J Inflamm (Lond). 5(4):13 pages.
Ki, S. H. et al. (Oct. 2010). "Interleukin-22 Treatment Ameliorates Alcoholic Liver Injury In A Murine Model Of Chronic-Binge Ethanol Feeding: Role Of Signal Transducer And Activator Of Transcription 3," Hepatology 52(4):1291-1300.
Kim, T.W. et al. (Jan. 14, 2006). "Involvement Of Lymphocytes In Dextran Sulfate Sodium-Induced Experimental Colitis," World J Gastroenterol. 12(2):302-305.
Ma, H.L. (Feb. 2008). "IL-22 Is Required For Th17 Cell-Mediated Pathology In A Mouse Model Of Psoriasis-Like Skin Inflammation," J Clin Invest.118(2):597-607.
Mihi, B. et al. (Jun. 15, 2021). "Interleukin-22 Signaling Attenuates Necrotizing Enterocolitis by Promoting Epithelial Cell Regeneration," Cell Reports 2(100320):1-12, 18 pages.
Mitra, A. et al. (2012). "Functional Role Of IL-22 In Psoriatic Arthritis," Arthritis Research & Therapy 14(2):1-10.
Res, P.C.M. et al. (Nov. 24, 2010). "Overrepresentation Of IL-17A And IL-22 Producing CD8 T Cells In Lesional Skin Suggests Their Involvement In The Pathogenesis Of Psoriasis," Plos One 5(11):e14108, 11 pages.
Rutz, S. et al. (Feb. 13, 2013). "IL-22, Not Simply A Th17 Cytokine," Immunol Rev. 252(1):116-132, 1 page (Abstract Only).
Scheiermann, P. et al. (Apr. 2013). "Application Of Interleukin-22 Mediates Protection In Experimental Acetaminophen-Induced Acute Liver Injury," The American Journal Of Pathology 182(4):1107-1113.
Tang, K.-Y. et al. (2019, e-pub Apr. 18, 2018). "Safety, Pharmacokinetics, And Biomarkers Of F-652, A Recombinant Human Interleukin-22 Dimer, In Healthy Subjects," Cellular & Molecular Immunology 16(5):473-482.
Varona, R. (Jul. 1, 2005, e-pub Mar. 17, 2005) "CCR6 Regulates CD4+ T-Cell-Mediated Acute Graft-Versus-Host Disease Responses," Blood. 106(1):18-26.
Wolk, K. et al. (2009, e-pub Mar. 30, 2009). "IL-22 And IL-20 Are Key Mediators Of The Epidermal Alterations In Psoriasis While IL-17 And IFN-γ Are Not," Journal Of Molecular Medicine 87(5):523-536.
Zhao, K. et al. (Dec. 2013, e-pub May 20, 2013). "The Identification And Characteristics Of IL-22-Producing T Cells In Acute Graft-

(56) References Cited

OTHER PUBLICATIONS

Versus-Host Disease Following Allogeneic Bone Marrow Transplantation," Immunobiology. 218(12):1505-1513.
Food and Drug Administration. (Jul. 2005). "Guidance For Industry: Estimating The Maximum Safe Starting Dose In Initial Clinical Trials For Therapeutics In Adult Healthy Volunteers," Center For Drug Evaluation And Research (CDER) 7(0.001):30 pages.
Food and Drug Administration. (May 5, 2016). "Drug Research and Children," 8 pages, as retrieved on Feb. 7, 2022 fromhttps://www.fda.gov/drugs/information-consumers-and-patients-drugs/drug-research-and-children.
Hackam, D. et al. (Feb. 2018). "Necrotizing Enterocolitis: Pathophysiology From A Historical Context," Semin Pediatr Surg. 27(1):11-18, 17 pages.
Heel, K. A. et al. (Feb. 1997). "Review: Peyer's Patches," Journal Of Gastroenterology And Hepatology 12(2):122-136.
Heida, F. H. et al. (Aug. 2016, e-pub. May 4, 2016). "Paneth Cells In The Developing Gut: When Do They Arise And When Are They Immune Competent?" Pediatric Research 80(2): 306-310.
Ivanov, S. et al. (Jun. 30, 2013). "Interleukin-22 Reduces Lung Inflammation During Influenza A Virus Infection and Protects Against Secondary Bacterial Infection and Protects Against Secondary Bacterial Infection," Journal of Virology 12(87)6911-6924.
Katara, A. N. et al. (Mar.-Apr. 2004). "Necrotizing Enterocolitis In Adults: A Study Of Four Cases," Indian Journal of Surgery 66(2):115-118.
Lamarthee, B. at al. (Apr. 2016). "Interleukin-22 in Graft-Versus-Host Disease after Allogeneic Stem Cell Transplantation," Front. Immunol. 7:148, 9 pages.
Levy, O. (May 2007). "Innate Immunity Of The Newborn: Basic Mechanisms And Clinical Correlates," Nature Reviews Immunology 7(5):379-390.
Lim, A.A. et al. (Jun. 19, 2020). "Comparison Of Human And Mouse Fetal Intestinal Tissues Reveals Differential Maturation Timelines," bioRxiv, 22 pages.
Mcelroy, S.J. et al. (2013). "Paneth Cells And Necrotizing Enterocolitis: A Novel Hypothesis For Disease Pathogenesis," Neonatology 103(1):10-20.
Mcgee, H. M. et al. (2013, e-pub. Dec. 6, 2012). "IL-22 Promotes Fibroblast-Mediated Wound Repair In The Skin," Journal of Investigative Dermatology 133(5):1321-1329.
Nursing and Midwifery Council (Nov. 19, 2007). "The Administration Of Medicines," Medicines Management, 7 pages.
Piaggesi, A. et al. (Oct. 17-19, 2019). "A Randomized, Multiple-Dose Study of Subcutaneous UTTR1147A (IL-22Fc) in Patients with Neuropathic, Non-Healing Diabetic Foot Ulcers (DFUs)," Abstract IDL 67, Poster presented at Diabetic Foot Global Conference (DFCon), Oct. 17-19, 2019, Los Angeles, CA, 1 page.
Roche (Dec. 2020). "Summary Of Clinical Trial Results: A Study To Look At A New Medicine Called "UTTR1147A"—How Safe Are Different Doses For Healthy People And Patients To Take—And How Is This Medicine Processed Through The Body," ClinicalTrialsGov No. NCT02749630, 10 pages.
Rothenberg, M. E. et al. (Jan. 2019). "Randomized Phase I Healthy Volunteer Study Of UTTR 1147A (IL-22Fc): A Potential Therapy For Epithelial Injury," Clinical Pharmacology & Therapeutics 105(1):177-189.
Stanford, A. H. et al. (Jul. 2020, e-pub. Jun. 26, 2019). "A Direct Comparison Of Mouse And Human Intestinal Development Using Epithelial Gene Expression Patterns," Pediatric Research 88(1):66-76.
Stoner, K. L. et al. (2015, e-pub. Jul. 12, 2014). "Intravenous Versus Subcutaneous Drug Administration. Which Do Patients Prefer? A Systematic Review," The Patient-Patient-Centered Outcomes Research 8(2):145-153, 2 pages. (Abstract Only).
Thapar, N. et al. (May 2005). "Long-Term Outcome Of Intractable Ulcerating Enterocolitis Of Infancy," Journal Of Pediatric Gastroenterology And Nutrition 40(5):582-588.
Underwood, M.A. (2012). "Paneth Cells And Necrotizing Enterocolitis," Gut Microbes. 3(6):562-565.

Wagner, F. et al. (2020). "P420 A Randomised, Observer-Blinded Phase 1b Multiple, Ascending Dose Study Of UTTR1147A, An IL-22Fc Fusion Protein, In Healthy Volunteers And Ulcerative Colitis Patients," Journal of Crohn's and Colitis 14(Supplement 1):S382-S383.
Wang, X. et al. (Oct. 9, 2014). "Interleukin-22 Alleviates Metabolic Disorders Andrestores Mucosal Immunity In Diabetes," Nature 514(7521):237-241.
Wu, D. et al. (2021). "IL-17-Dependent Fibroblastic Reticular Cell Training Boosts Tissue Protective Mucosal Immunity Through IL-10-Producing B Cells," Science Immunology 6(66):eaao3669, 14 pages.
Zwarycz, B. et al. (Dec. 17, 2021). "IL22 Inhibits Epithelial Stem Cell Expansion In An Ileal Organoid Model," Cellular And Molecular Gastroenterology And Hepatology 7(1):1-17.
Emami, C.N. et al. (Apr. 2012, e-pub. Jan. 30, 2014). "Role Of Interleukin-10 In The Pathogenesis Of Necrotizing Enterocolitis," The American Journal Of Surgery 203(4):428-435.
Fard, N.A. et al. (Jul.-Aug. 2016, e-pub. Aug. 1, 2016). "The Potential Role of T Helper Cell 22 and IL-22 in Immunopathogenesis of Multiple Sclerosis," Innov Clin Neurosci. 13(7-8):30-36.
Kong, Q. et al. (Oct. 11, 2012). "Increased Expressions Of IL-22 And Th22 Cells In The Coxsackievirus B3-Induced Mice Acute Viral Myocarditis," Virol. J. 9(232):1-10.
Levine, J.E. et al. (Jan. 1, 2015). "A Prognostic Score For Acute Graft-Versus-Host Disease Based On Biomarkers: A Multicentre Study," Lancet Haematol. 2(1):e21-e29.
Miettinen, P.J. et al. (Jul. 27, 1995). "Epithelial Immaturity And Multiorgan Failure In Mice Lacking Epidermal Growth Factor Receptor," Nature 376(6538):337-341.
Nazani, A.F. et al. (Jul.-Aug. 2016). "The Potential Role of T Helper Cell 22 and IL-22 in Immunopathogenesis of Multiple Sclerosis," Innovations in Clinical Neuroscience 13(7-8):30-36.
NIH (Apr. 2, 2015). "Study of IL-22 IgG2-Fc (F-652) for Subjects With Grade II IV Lower GI aGVHD," ClinicalTrials.gov, No. NCT02406651, 13 pages, retrieved on Jun. 27, 2022, from https://www.clinicaltrials.gov/ct2/show/results/NCT02406651?term=NCT02406651&draw=2&rank=1&view=results.
Pociask, D. et al. (Apr. 2013). "IL-22 Is Essential For Lung Epithelial Repair Following Influenza Infection," Am. J. Pathol. 182(4):1286-1296.
Suzuki, A. et al. (Oct. 2010). "EGF Signaling Activates Proliferation And Blocks Apoptosis Of Mouse And Human Intestinal Stem/Progenitor Cells In Long-Term Monolayer Cell Culture," Laboratory Investigation 90(10):1425-1436.
U.S. Appl. No. 17/799,627, filed Aug. 12, 2022, by Yang et al. (Copy not submitted herewith pursuant to the waiver of 37 C.F.R. § 1.98 (a)(2)(iii) issued by the Office on Sep. 21, 2004.).
Xiang, X. et al. (2011). "IL-22 And Non-ELR-CXC Chemokine Expression In Chronic Hepatitis B Virus-Infected Liver," Immunol. Cell Biol. 90(6):1-9.
Xin, N. et al. (2015, e-pub. Aug. 24, 2015). "Exploring The Role Of Interleukin-22 In Neurological And Autoimmune Disorders," Int Immunopharmacol. 28(2):1076-1083.
Yazji, I. et al. (May 6, 2013). "Endothelial TLR4 Activation Impairs Intestinal Microcirculatory Perfusion In Necrotizing Enterocolitis Via Enos-NO-Nitrite Signaling," Proceedings Of The National Academy of Sciences 110(23):9451-9456.
Guiddir, T. et al. (2014). "Anti-TNF-A Therapy May Cause Neonatal Neutropenia," Pediatrics. 134(4):e1189-1193.
International Preliminary Report on Patentability dated Aug. 23, 2022, dated Apr. 29, 2021 for International Application No. PCT/CN2021/076929, filed on Feb. 19, 2021, 6 pages.
International Preliminary Report on Patentability dated Aug. 23, 2022, dated May 14, 2021 for International Application No. PCT/CN2021/076519, filed on Feb. 10, 2021, 6 pages.
International Search Report and Written Opinion dated May 14, 2021 for International Application No. PCT/CN2021/076519, filed on Feb. 10, 2021, sixteen pages.
Lindemans, C. et al. (Dec. 24, 2015). "Interleukin-22 Promotes Intestinal-Stem-Cell-Mediated Epithelial Regeneration," Nature 528(7583):560-564, 28 pages.

(56) References Cited

OTHER PUBLICATIONS

U.S. Appl. No. 17/800,827, filed Aug. 18, 2022, by Daley et al. (Copy not submitted herewith pursuant to the waiver of 37 C.F.R. § 1.98 (a)(2)(iii) issued by the Office on Sep. 21, 2004.).

Zani, A. et al. (2015, e-pub. Oct. 26, 2014). "International Survey On The Management Of Necrotizing Enterocolitis," European Journal of Pediatric Surgery 25(01):27-33.

International Search Report and Written Opinion dated Apr. 29, 2021 for International Application No. PCT/CN2021/076929, filed on Feb. 19, 2021, sixteen pages.

Han, L. et al. (2019). "Intestinal Microbiota Can Predict Acute Graft-Versus-Host Disease Following Allogeneic Hematopoietic Stem Cell Transplantation," Biology Of Blood And Marrow Transplantation 25(10):1944-1955.

Ponce, D.M. et al. (2020). "A Phase 2 Study of F-652, a Novel Tissue-Targeted Recombinant Human Interleukin-22 (IL-22) Dimer, for Treatment of Newly Diagnosed Acute Gvhd of the Lower GI Tract," Biol Blood Marrow Transplant. 26(3):S51-S52.

Zheng, Y.H. et al. (Feb. 28, 2019, e-pub. Feb. 15, 2019). "IL-22/IL-22R1 Axis is Involved in Myocardial Injury of a Mouse Cecal Ligation and Puncture Model," American Journal of Translational Research 2(11):998-1008.

\* cited by examiner

USE OF IL-22 IN TREATING NECROTIZING ENTEROCOLITIS

CROSS-REFERENCE TO RELATED APPLICATIONS

This application is a National Phase filing under 35 U.S.C. § 371 of International Application No. PCT/US2017/027806 having an international filing date of Apr. 14, 2017, which claims priority benefit of U.S. Provisional Patent Application No. 62/323,584, filed on Apr. 15, 2016, the contents of which are hereby incorporated herein by reference in their entirety.

ACKNOWLEDGEMENT OF GOVERNMENT SUPPORT

This invention was made with government support under NIH contract no. K06DK101608 awarded by the National Institutes of Health. The U.S. government has certain rights in this invention.

SUBMISSION OF SEQUENCE LISTING ON ASCII TEXT FILE

The contents of the following submission on ASCII text file are incorporated herein by reference in their entirety: a computer readable form (CRF) of the Sequence Listing (file name: 720622001300SEQLIST.TXT, date recorded: Oct. 11, 2018, size: 22 KB).

FIELD OF THE INVENTION

This invention relates to the area of biological and medical technologies, in particular, this invention relates to the use of IL-22, dimers or multimers thereof in preventing and/or treating intestinal inflammations in children, such as necrotizing enterocolitis.

BACKGROUND OF THE INVENTION

Necrotizing enterocolitis (NEC) is a leading cause of death in premature infants. It is characterized by intestinal inflammation and necrosis of gut epithelium and loss of gut barrier, leading to bacterial translocation. NEC is triggered by an exaggerated inflammatory response resulting in intestinal necrosis. NEC-induced inflammation leads to gut barrier dysfunction, intestinal stem cell loss, and impaired mucosal healing. NEC may further lead to systemic inflammation, affecting distant organs such as the brain and placing affected infants at substantially increased risk for neurodevelopmental delays.

The mean prevalence of NEC is about 7% among infants with a birth weight between 500 g and 1500 g. Due to advances in obstetric and neonatal care, the population of preterm infants at risk for NEC continues to increase. The estimated rate of death associated with NEC ranges between 20% and 30%, with the highest among infants requiring surgery. Current treatment strategies for NEC include abdominal decompression, bowel rest, broad-spectrum intravenous antibiotics, intravenous hyperalimentation, and surgery, such as peritoneal drain placement, and laparotomy with resection of diseased bowel. Breast-feeding remains to be the most effective preventive strategy for NEC. However, current preventative and therapeutic methods for NEC fail to reduce the incidence of NEC and associated morbidity and mortality rates in neonates. There is a clear need for an effective method of preventing and/or treating NEC.

Interleukin-22 (IL-22), also known as IL-10 related T cell-derived inducible factor (IL-TIF), is a glycoprotein expressed in and secreted from activated T cells and natural killer cells (NK cells). Activated T cells are mainly CD4+ cells, especially CD28 pathway activated $T_h1$ cells, $T_h17$ cells and $T_h22$ cells, among others. The expression of IL-22 mRNA was originally identified in IL-9 simulated T cells and mast cells in murine, as well as Concanavilin A (Con A) stimulated spleen cells (Dumoutier, et al., J. Immunology, 164:1814-1819, 2000). The human IL-22 mRNA is mainly expressed in peripheral T cells upon stimulation by anti-CD3 or Con A.

The disclosures of all publications, patents, patent applications and published patent applications referred to herein are hereby incorporated herein by reference in their entirety.

BRIEF SUMMARY OF THE INVENTION

The present application provides methods and compositions for treating and/or preventing necrotizing enterocolitis (NEC) and other intestinal inflammations in children (such as neonates) using IL-22, dimers, or multimers thereof.

In one aspect of the present application, there is provided a method of preventing and/or treating necrotizing enterocolitis (NEC) in an individual, comprising administering to the individual an effective amount of an IL-22, a dimer, or a multimer thereof. In some embodiments, the NEC is stage I NEC. In some embodiments, the NEC is stage II NEC. In some embodiments, the NEC is stage III NEC.

In some embodiments according to any of the methods described above, the individual is a preterm infant, such as a premature infant. In some embodiments, the individual is an infant having a low birth weight (e.g., a very low birth weight infant, or an extremely low birth weight infant, such as an infant with a birth weight of about 500 g to about 1000 g).

In some embodiments according to any of the methods described above, the effective amount of the IL-22, dimer, or multimer thereof results in inhibition of TLR4 in the individual.

In some embodiments according to any of the methods described above, the effective amount of the IL-22, dimer, or multimer thereof results in inhibition of pro-inflammatory cytokines (such as IL-6) and/or inflammation-induced enzymes (such as iNOS) in the individual.

In some embodiments according to any of the methods described above, the effective amount of the Il-22, dimer, or multimer thereof promotes differentiation and/or growth of secretory cells (such as goblet cells, Paneth cells, etc.) in the intestine of the individual.

In some embodiments according to any of the methods described above, the effective amount of IL-22, dimer, or multimer thereof regulates one or more host defense genes in the individual selected from the group consisting of Defa-ps1, Defa22, Defa29, Reg3g, Reg3b, Reg3d, Reg3a, Reg4 and Reg1.

In some embodiments according to any of the methods described above, the method comprises administering to the individual an effective amount of an IL-22 dimer. In some embodiments, the IL-22 dimer comprises two monomeric subunits, wherein each monomeric subunit comprises an IL-22 domain and a dimerization domain. In some embodiments, the monomeric subunit comprises an IL-22 domain linked to a dimerization domain. In some embodiments, the monomeric subunit comprises an IL-22 domain linked to a dimerization domain via a linker. In some embodiments, the linker is about 5 to about 50 amino acids. In some embodiments, the linker comprises the sequence of SEQ ID NO: 1 or SEQ ID NO: 10. In some embodiments, the linker has the sequence of SEQ ID NO: 1 or SEQ ID NO: 10. In some embodiments, the dimerization domain comprises at least two cysteines capable of forming intermolecular disulfide bonds. In some embodiments, the dimerization domain comprises at least a portion of an fc fragment. In some embodiments, the Fc fragment is an Fc fragment of human immunoglobulin (such as IgG1, IgG2, IgG3, or IgG4). In some embodiments, the Fc fragment comprises CH2 and CH3 domains. In some embodiments, the Fc fragment comprises the sequence of SEQ ID NO:2 or SEQ ID NO:9. In some embodiments, the Fc fragment has the sequence of SEQ ID NO:2 or SEQ ID NO:9. In some embodiments, the dimerization domain is at the N-terminus of the IL-22 domain. In some embodiments, the dimerization domain is at the C-terminus of IL-22 domain. In some embodiments, the IL-22 domain of each of the monomeric subunits has the sequence of SEQ ID NO:3. In some embodiments each of the monomeric subunits comprises an amino acid sequence selected from SEQ ID NO: 4 and SEQ ID NOs: 6-8.

In some embodiments according to any of the methods described above, the IL-22 dimer is administered at the effective amount of about 1 µg/kg to about 200 µg/kg, such as about 2 µg/kg to about 200 µg/kg, about 1 µg/kg to about 100 µg/kg, about 5 µg/kg to about 80 µg/kg, or about 10 µg/kg to shorn 45 µg/kg.

In some embodiment according to any of the methods described above, the IL-22 dimer is administered no more than about once every week, such as no more than about once every month, or no more than about once every three months.

In some embodiments according to any of the methods described above, the IL-22, dimer, or multimer thereof is administered intravenously.

In one aspect of the present application, there is provided a kit for preventing and/or treating necrotizing enterocolitis, comprising an IL-22, a dimer, or a multimer thereof and an instruction for administering the IL-22, dimer, or multimer thereof.

In one aspect of the present application, there is provided use of an interleukin-22 (IL-22), dimer, or multimer thereof in the manufacture of a medicament for treatment and/or prevention of necrotizing enterocolitis. In some embodiments, the IL-22 dimer is shown as in Formula I:

M1-L-M2 (I)

wherein,
M1 is a first monomer of IL-22.
M2 is a second monomer of IL-22, and
L is a fusion moiety connecting said first monomer and said second monomer and disposed therebetween.

In some embodiments according to any of the uses described above, the IL-22 dimer retains the biological activity of IL-22 and has a serum half-life of longer than twice of that of either the first or the second monomer. In some embodiments, the serum half-life of the IL-22 dimer is longer than three, five, or ten times of that of the first and/or the second monomer.

In some embodiments according to any of the uses described above, the fusion moiety L is selected from the group consisting of:
(i). a short peptide comprising 3 to 50 amino acids; and
(ii). a polypeptide of Formula II:

-Z-Y-Z- II wherein,
Y is a carrier protein,
Z is nothing, or a short peptide(s) comprising 1 to 30 amino acids, and
"-" is a chemical bond or a covalent bond.

In some embodiments, the "-" is a peptide bond.
In some embodiments, Z is 5-50 amino acid residues in length.
In some embodiments, Z comprises the sequence of SEQ ID NO: 1 or SEQ ID NO: 10. In some embodiments, Z has the sequence of SEQ ID NO: 1 or SEQ ID NO: 10.
In some embodiments, the carrier protein contains at least two cysteines capable of forming intermolecular disulfide bonds.
In some embodiments, the carrier protein is disposed at the N-terminus of the IL-22 monomer. In some embodiments, the carrier protein is disposed at the C-terminus of the IL-22 monomer.
In some embodiment, the carrier protein is albumin or Fc fragment of human IgG. In some embodiments, the Fc fragment contains CH2 and CH3 domains. In some embodiments, the Fc fragment comprises the sequence of SEQ ID NO: 2 or SEQ ID NO: 9. In some embodiments, the Fc fragment has the sequence of SEQ ID NO: 2 or SEQ ID NO: 9.

In some embodiments according to any of the uses described above, the IL-22 dimer is formed by two monomeric subunits wherein each monomeric subunit comprises an IL-22 domain, a dimerization domain and optionally a linker connecting the IL-22 domain and the dimerization domain. In some embodiments, the IL-22 domain is an IL-22 monomer, the dimerization domain comprises an Fc fragment of human immunoglobulin (such as IgG1, IgG2, IgG3, IgG4), the optional linker is a peptide connecting the IL-22 monomer and the Fc fragment, and the dimer is formed by connection of two dimerization domains (such as the Fe fragments) via one or more disulfide bond(s). In some embodiments, the number of said disulfide bond is 2-4.

In some embodiments according to any of the uses described above, the monomeric subunit of each IL-22 dimer comprises an amino acid sequence selected from SEQ ID NO: 4 and SEQ ID NOs: 6-8.

In some embodiments according to any of the uses described above, the first monomer and the second monomer of the IL-22 dimer are identical. In some embodiments, the first monomer and the second monomer are different.

In some embodiments according to any of the uses described above, the biological activity of the IL-22 dimer is selected from one or more biological activities in a group consisting of:
(a) inhibiting TLR4 in the individual;
(b) inhibiting one or more pro-inflammatory cytokines (such as IL-6) and/or inflammation-induced enzymes (such as iNOS) in the individual;
(c) promoting differentiation and/or growth of secretory cells (such as goblet cells, Paneth cells, etc.) in the intestine of the individual; and
(d) regulating one or more host defense genes in the individual selected from the group consisting of Defa-ps1, Defa22, Defa29, Reg3g, Reg3b, Reg3d, Reg3a, Reg4 and Reg1.

In another aspect of the present invention, there is provided a pharmaceutical composition for prevention and/or treatment of necrotizing enterocolitis, which comprises a pharmaceutically acceptable carrier and an IL-22 dimer of Formula I:

$$M1\text{-}L\text{-}M2 \quad (I)$$

wherein,
M1 is a first monomer of IL-22;
M2 is a second monomer of IL-22; and
L is a fusion moiety connecting said first monomer and said second monomer and disposed therebetween. In some, embodiments, the IL-22 dimer retains the biological activity of IL-22 and has a serum half-life of longer than twice of that of either the first or the second monomer.

In another aspect of the present application, there is provided use of an IL-22, a dimer, or a multimer thereof in the manufacture of a medicament for prevention and/or treatment of necrotizing enterocolitis. In some embodiments, the IL-22 dimer comprises two monomeric subunits, wherein each monomeric subunit comprises an IL-22 domain and a dimerization domain. In some embodiments, the monomeric subunit comprises an IL-22 domain linked to a dimerization domain. In some embodiments, the monomeric subunit comprises an IL-22 domain linked to a dimerization domain via a linker. In some embodiments, the linker is about 5 to about 50 amino acids. In some embodiments, the linker comprises the sequence of SEQ ID NO: 1 or SEQ ID NO: 10. In some embodiments, the linker has the sequence of SEQ ID NO:1 or SEQ ID NO: 10. In some embodiments, the dimerization domain comprises at least two cysteines capable of forming intermolecular disulfide bonds. In some embodiments, the dimerization domain comprises at least a portion of an Fc fragment. In some embodiments, the Fc fragment comprises CH2 and CH3 domains. In some embodiments, the Fc fragment comprises the sequence of SEQ ID NO:2 or SEQ ID NO:9. In some embodiments, the Fc fragment has the sequence of SEQ ID NO:2 or SEQ ID NO:9. In some embodiments, the IL-22 domain of each of the monomeric subunits has the sequence of SEQ ID NO:3. In some embodiments, each of the monomeric subunits comprises an amino acid sequence selected from SEQ ID NO:4 and SEQ ID NOs:6-8. In some embodiments, the IL-22 dimer is administered intravenously.

It is understood that aspect and embodiments of the invention described herein include "consisting" and/or "consisting essentially of" aspects and embodiments.

Reference to "about" a value or parameter herein includes (and describes) variations that are directed to that value or parameter per se. For example, description referring to "about X" includes description of "X".

As used herein and in the appended claims, the singular forms "a," "or," and "the" include plural referents unless the context clearly dictates otherwise. It is understood that aspects and variations of the invention described herein include "consisting" and/or "consisting essentially of" aspects and variations.

It is clear for a skilled person in the art that one, some, or all of the properties of the various embodiments described herein may be combined to form other embodiments of the present invention. Hence this invention should not be construed as limited to the embodiments set forth herein.

BRIEF DESCRIPTION OF THE DRAWINGS

As illustrated in FIG. 2A, the oval-shaped object labeled with "C" represents a carrier protein wherein the IL-22 is disposed at the N-terminus of the carrier protein. As illustrated in FIG. 2B, the half oval-shaped object labeled with "Fc" represents an Fc fragment which is a dimerization domain, showing that a dimer is formed by the coupling of two Fc fragments via disulfide bond(s).

As illustrated in FIG. 3A, the oval-shaped object labeled with "C" represents a carrier protein wherein the IL-22 is disposed at the C-terminus of the carrier protein. As illustrated in FIG. 3B, the half oval-shaped object labeled with "Fc" represents an Fc fragment which is a dimerization domain, showing a dimer is formed by the coupling of two Fc fragments via disulfide bond(s).

In FIGS. 6A-11B, rIL-22 is an exemplary IL-22 dimer having two monomeric subunit each comprising SEQ ID NO: 4.

FIG. 7 shows confocal microscopy images of mouse (top panels) and human enteroids (bottom panels) that were treated with control (left panels) or an IL-22 dimer (right panels). The enteroids were stained for enterocytes (E-cadherin, green), goblet cells (Muc2, red), and nuclei (DAPI, blue).

FIG. 8 shows a heat map of expression levels of selected host defense genes in small intestine enteroids treated with an exemplary IL-22 dimer compared to control.

FIG. 9 shows confocal microscopy images and quantifications of goblet cells and Paneth cells in wildtype mice treated with an IL-22 dimer or IgG (control). Goblet cells were stained against Muc2 (green), Paneth cells were stained against lysozyme (red), and nucleic were stained with DAPI (blue).

FIG. 10 shows expression of TLR4 in the terminal ileum of wildtype mice treated with an IL-22 dimer or IgG (control) as determined by qRT-PCR.

FIG. 11B shows expression levels of iNOS (inducible nitric oxide synthase) in the intestine of mice as determined by qRT-PCR.

DETAILED DESCRIPTION OF THE INVENTION

Figure 1:
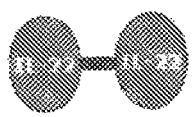
FIG. 1 is an illustration of an exemplary IL-22 dimer according to the present invention. In the figure, "-" represents a linker and the oval-shaped object labeled with "IL-22" represents an IL-22 monomer.
Figure 2A:
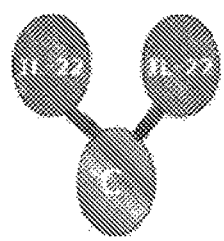
FIGS. 2A and 2B are illustrations of exemplary IL-22 dimers according to the present invention. In the figures, "-" represents an amino acid linker and the oval-shaped object labeled with "IL-22" represents an IL-22 monomer.
Figure 2B:
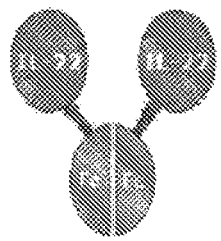
Figure 3A:
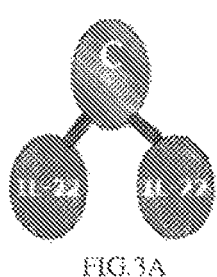
FIGS. 3A and 3B are illustrations of exemplary IL-22 dimers according to the present invention. In the figures, "-" represents an amino acid linker, the oval-shaped object labeled with "IL-22" represents an IL-22 monomer.
Figure 3B:
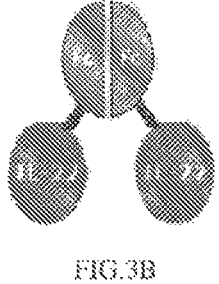

The present application provides methods of preventing and/or treating necrotizing enterocolitis in an individual by administering (such as intravenously administering) to the individual an effective amount of an IL-22, a dimer, or a multimer thereof. Inventors of the present application discovered for the first time the role of IL-22 signaling in counteracting the pathogenesis of necrotizing enterocolitis. Using a murine model for necrotizing enterocolitis, inventors have demonstrated that IL-22 is highly effective in treating necrotizing enterocolitis, and can significantly attenuate the severity of NEC in vivo. The inventors have further found that IL-22 can protect intestinal epithelial cells from inflammation in vitro and in vivo, inhibit TLR4 signaling and expression of downstream pro-inflammatory cytokines and inflammation-induced enzymes, promote differentiation and growth of goblet cells and Paneth cells, and regulate the expression of host defense genes in mice and human enteroids.

Thus, in some embodiments, there is provided a method of preventing necrotizing enterocolitis in an individual (such as a neonate), comprising administering (such as intravenously administering) to the individual an effective amount of an IL-22, a dimer, or a multimer thereof. In some embodiments, there is provided a method of treating necrotizing enterocolitis in an individual (such as a neonate), comprising administering (such as intravenously administering) to the individual an effective amount of an IL-22, a dimer, or a multimer thereof.

In some embodiments, there is provided a method of preventing necrotizing enterocolitis in an individual (such as a neonate), comprising administering (such as intravenously administering) to the individual an effective amount of an IL-22 dimer. In some embodiments, there is provided a method of treating necrotizing enterocolitis in an individual (such as a neonate), comprising administering (such as intravenously administering) to the individual an effective amount of an IL-22 dimer.

In some embodiments, there is provided a method of preventing necrotizing enterocolitis in an individual (such as a neonate), comprising administering (such as intravenously administering) to the individual an effective amount of an IL-22 dimer comprising two monomeric subunits, wherein each monomeric subunit comprises an IL-22 domain linked to a dimerization domain comprising at least a portion of an Fc fragment via an optional linker. In some embodiments, there is provided a method of treating necrotizing enterocolitis in an individual (such as a neonate), comprising administering (such as intravenously administering) to the individual an effective amount of an IL-22 dimer comprising two monomeric subunits, wherein each monomeric subunit comprises an IL-22 domain linked to a dimerization domain comprising at least a portion of an Fc fragment via an optional linker. In some embodiments, the IL-22 domain comprises the amino acid sequence of SEQ ID NO: 3. In some embodiments, the Fc fragment comprises the sequence of SEQ ID NO:2 or SEQ ID No:9. In some embodiments, the linker comprises the sequence of SEQ ID NO:1 or SEQ ID NO:10. In some embodiments, the dimerization domain is at the N-terminus of the IL-22 domain. In some embodiments, the dimerization domain is at the C-terminus of the IL-22 domain.

In some embodiments, there is provided a method of preventing necrotizing enterocolitis in an individual (such as a neonate), comprising administering (such as intravenously administering) to the individual an effective amount of an IL-22 dimer comprising two monomeric subunits each comprising an amino acid sequence selected from SEQ ID NO: 4 and SEQ ID NOs: 6-8. In some embodiments, there is provided a method of treating necrotizing enterocolitis in an individual (such as a neonate), comprising administering (such as intravenously administering) to the individual an effective amount of an IL-22 dimer comprising two monomeric subunits each comprising an amino acid sequence selected from SEQ ID NO: 4 and SEQ ID NOs: 6-8.

In some embodiments, there is provided a method of inhibiting inflammation in an individual (such as a neonate) having necrotizing enterocolitis, comprising administering (such as intravenously administering) to the individual an effective amount of an IL-22, a dimer, or a multimer thereof. In some embodiments, there is provided a method of inhibiting inflammation in an individual (such as a neonate) at risk of having necrotizing enterocolitis, comprising administering (such as intravenously administering) to the individual an effective amount of an IL-22, a dimer, or a multimer thereof. In some embodiments, there is provided a method of inhibiting inflammation in an individual (such as a neonate) having or at the risk of having necrotizing enterocolitis, comprising administering (such as intravenously administering) to the individual an effective amount of an IL-22 dimer comprising two monomeric subunits, wherein each monomeric subunit comprises an IL-22 domain linked to a dimerization domain comprising at least a portion of an Fc fragment via an optional linker. In some embodiments, the dimerization domain comprises at least a portion of an Fc fragment (such as Fc fragment of human IgG). In some embodiments, the IL-22 domain comprises the amino acid sequence of SEQ ID NO: 3. In some embodiments, the Fc fragment comprises the sequence of SEQ ID NO:2 or SEQ ID No:9. In some embodiments, the linker comprises the sequence of SEQ ID NO:1 or SEQ ID NO:10. In some embodiments, the dimerization domain is at the N-terminus of the IL-22 domain. In some embodiments, the dimerization domain is at the C-terminus of the IL-22 domain. In some embodiments, each of the monomeric subunits comprises an amino acid sequence selected from SEQ ID NO: 4 and SEQ ID NOs: 6-8.

In some embodiments, there is provided a method of protecting intestinal epithelial cells against inflammation in an individual (such as a neonate) having necrotizing enterocolitis, comprising administering (such as intravenously administering) to the individual an effective amount of an IL-22, a dimer, or a multimer thereof. In some embodiments, there is provided a method of protecting intestinal epithelial cells against inflammation in an individual (such as a neonate) at risk of having necrotizing enterocolitis, comprising administering (such as intravenously administering) to the individual an effective amount of an IL-22, a dimer, or a multimer thereof. In some embodiments, there is provided a method of protecting intestinal epithelial cells against inflammation in an individual (such as a neonate) having or at the risk of having necrotizing enterocolitis, comprising administering (such as intravenously administering) to the individual an effective amount of an IL-22 dimer comprising two monomeric subunits, wherein each monomeric subunit comprises an IL-22 domain linked to a dimerization domain comprising at least a portion of an Fc fragment via an optional linker. In some embodiments, the dimerization domain comprises at least a portion of an Fc fragment (such as Fc fragment of human IgG). In some embodiments, the IL-22 domain comprises the amino acid sequence of SEQ ID NO: 3. In some embodiments, the Fc fragment comprises the sequence of SEQ ID NO:2 or SEQ ID No:9. In some embodiments, the linker comprises the sequence of SEQ ID NO: 1 or SEQ ID NO:10. In some embodiments, the dimerization domain is at the N-terminus of the IL-22 domain. In some embodiments, the dimerization domain in at the C-terminus of the IL-22 domain. In some embodiments, each of the monomeric subunits comprises an amino acid sequence selected from SEQ ID NO: 4 and SEQ ID NOs: 6-8.

In some embodiments, there is provided a method of reducing one or more symptoms of necrotizing enterocolitis in an individual (such as a neonate), comprising administering (such as intravenously administering) to the individual an effective amount of an IL-22, a dimer, or a multimer thereof. In some embodiments, there is provided a method of reducing one or more symptoms of necrotizing enterocolitis in an individual (such as a neonate), comprising administering (such as intravenously administering) to the individual an effective amount of an IL-22 dimer comprising two monomeric subunits, wherein each monomeric subunit comprises an IL-22 domain linked to a dimerization domain comprising in least a portion of an Fc fragment via an optional linker. In some embodiments, the dimerization domain comprises at least a portion of an Fc fragment (such as Fc fragment of human IgG). In some embodiments, the IL-22 domain comprises the amino acid sequence of SEQ ID NO: 3. In some embodiments, the Fc fragment comprises the sequence of SEQ ID NO:2 or SEQ ID No:9. In some embodiments, the linker comprises the sequence of SEQ ID NO:1 or SEQ ID NO:10. In some embodiments, the dimerization domain is at the N-terminus of the IL-22 domain. In some embodiments, the dimerization domain is at the C-terminus of the IL-22 domain. In some embodiments, each of the monomeric subunits comprises an amino acid sequence selected from SEQ ID NO: 4 and SEQ ID NOs: 6-8.

In some embodiments, there is provided a method of reducing morbidity and/or mortality of an individual (such as neonate) having necrotizing enterocolitis, comprising administering (such as intravenously administering) to the individual an effective amount of an IL-22, a dimer, or a multimer thereof. In some embodiments, there is provided a method of reducing morbidity and/or mortality of an individual (such as neonate) at risk of having necrotizing enterocolitis, comprising administering (such as intravenously administering) to the individual an effective amount of an IL-2, a dimer, or a multimer thereof. In some embodiments, there is provided a method of reducing morbidity and/or mortality of an individual (such as neonate) having or at the risk of having necrotizing enterocolitis, comprising administering (such as intravenously administering) to the individual an effective amount of an IL-22 dimer comprising two monomeric subunits, wherein each monomeric subunit comprises an IL-22 domain linked to a dimerization domain comprising at least a portion of an Fc fragment via an optional linker. In some embodiments, the dimerization domain comprises at least a portion of an Fc fragment (such as Fc fragment of human IgG). In some embodiments, the IL-22 domain comprises the amino acid sequence of SEQ ID NO: 3. In some embodiments, the Fc fragment comprises the sequence of SEQ ID NO:2 or SEQ ID No:9. In some embodiments, the linker comprises the sequence of SEQ ID NO:1 or SEQ ID NO:10. In some embodiments, the dimerization domain is at the N-terminus of the IL-22 domain. In some embodiments, the dimerization domain is at the C-terminus of the IL-22 domain. In some embodiments, each of the monomeric subunits comprises an amino acid sequence selected from SEQ ID NO: 4 and SEQ ID NOs: 6-8.

In some embodiments, there is provided a method of improving quality of life in an individual (such as a neonate) having necrotizing enterocolitis, comprising administering (such as intravenously administering) to the individual an effective amount of an IL-22, a dimer, or a multimer thereof. In some embodiments, there is provided a method of improving quality of life in an individual (such as a neonate) at risk of having necrotizing enterocolitis, comprising administering (such as intravenously administering) to the individual an effective amount of an IL-22, a dimer, or a multimer thereof. In some embodiments, there is provided a method of improving quality of life in an individual (such as a neonate) having or at the risk of having necrotizing enterocolitis, comprising administering (such as intravenously administering) to the individual an effective amount of an IL-22 dimer comprising two monomeric subunits, wherein each monomeric subunit comprises an IL-22 domain linked to a dimerization domain comprising at least a portion of an Fc fragment via an optional linker. In some embodiments, the dimerization domain comprises at least a portion of an Fc fragment (such as Fc fragment of human IgG). In some embodiments, the IL-22 domain comprises the amino acid sequence of SEQ ID NO: 3. In some embodiments, the Fc fragment comprises the sequence of SEQ ID NO:2 or SEQ ID No:9. In some embodiments, the linker comprises the sequence of SEQ ID NO:1 or SEQ ID NO:10. In some embodiments, the dimerization domain is at the N-terminus of the IL-22 domain. In some embodiments, the dimerization domain is at the C-terminus of the IL-22 domain. In some embodiments, each of the monomeric subunits comprises an amino acid sequence selected from SEQ ID NO: 4 and SEQ ID NOs: 6-8.

In some embodiments, the effective amount of the IL-22, dimer, or multimer thereof results in one or more (such as any of 1, 2, 3, 4, or more) of treatment endpoints including, but not limited to: (a) inhibiting TLR4 (such as expression or signaling) in the individual; (b) inhibiting one or more pro-inflammatory cytokines (such as IL-6) and/or inflammation-induced enzymes (such as iNOS) in the individual; (c) promoting differentiation and/or growth of secretory cells (such as goblet cells, Paneth cells, etc.) in the intestine of the individual; and (d) regulating one or more host defense genes in the individual selected from the group consisting of Defa-ps1, Defa22, Defa29, Reg3g, Reg3b, Reg3d, Reg3a, Reg4 and Reg1. In some embodiments, there is provided a method of treating and/or preventing necrotizing enterocolitis in an individual, comprising administering (such as intravenously administering) to the individual an effective amount of an IL-22, a dimer, or a multimer thereof, wherein the effective amount of the IL-22, a dimer, or multimer thereof results in one or more (such as any of 1, 2, 3, 4, or more) of the treatment endpoints described above. In some embodiments, there is provided a method of inhibiting TLR4 (such as expression or signaling) in an individual (such as a neonate) having necrotizing enterocolitis, comprising administering (such as intravenously administering) to the individual an effective amount of an IL-22, a dimer, or a multimer thereof. In some embodiments, there is provided a method of inhibiting TLR4 (such as expression or signaling) in an individual (such as a neonate) at risk of having necrotizing enterocolitis, comprising administering (such as intravenously administering) to the individual an effective amount of an IL-22, a dimer, or a multimer thereof. In some embodiments, there is provided a method of preventing and/or treating necrotizing enterocolitis in an individual (such as a neonate), comprising administering (such as intravenously administering) to the individual an effective amount of an IL-22, a dimer, or a multimer thereof, wherein the effective amount of the IL-22, dimer, or multimer thereof inhibits TLR4 (such as expression or signaling) in the individual. In some embodiments, the expression level of TLR4 is decreased at least about any one of 1.5×, 2×, 3×, 4×, 5×, 6×, 7×, 8×, 9×, 10× or more compared to the level of TLR4 prior to the treatment. In some embodiments, the IL-22 dimer comprises two monomeric subunits, wherein each monomeric subunit comprises an IL-22 domain linked to a dimerization domain via an optional linker. In some embodiments, the dimerization domain comprises at least a portion of an Fc fragment (such as Fc fragment of human IgG). In some embodiments, the IL-22 domain comprises the amino acid sequence of SEQ ID NO: 3. In some embodiments, the Fc fragment comprises the sequence of SEQ ID NO:2 or SEQ ID No:9. In some embodiments, the linker comprises the sequence of SEQ ID NO:1 or SEQ ID NO:10. In some embodiments, the dimerization domain is at the N-terminus of the IL-22 domain. In some embodiments, the dimerization domain is at the C-terminus of the IL-22 domain. In some embodiments, each of the monomeric subunits comprises an amino acid sequence selected from SEQ ID NO: 4 and SEQ ID NOs: 6-8.

In some embodiments, there is provided a method of inhibiting expression of one or more pro-inflammatory cytokines (such as IL-6) and/or inflammation-induced enzymes (such as iNOS) in an individual (such as a neonate) having necrotizing enterocolitis, comprising administering (such as intravenously administering) to the individual an effective amount of an IL-22, a dimer, or a multimer thereof. In some embodiments, there is provided a method of inhibiting expression of one or more pro-inflammatory cytokines (such as IL-6) and/or Inflammation-induced enzymes (such as iNOS) in an individual (such as a neonate) at risk of having necrotizing enterocolitis, composing administering (such as intravenously administering) to the individual an effective amount of an IL-22, a dimer, or a multimer thereof. In some embodiments, there is provided a method of treating necrotizing enterocolitis in an individual (such as a neonate), comprising administering (such as intravenously administering) to the individual an effective amount of an IL-22, dimer, or a multimer thereof, wherein the effective amount of the IL-22, dimer, or multimer thereof inhibits expression of one or more pro-inflammatory cytokines (such as IL-6) and/or inflammation-induced enzymes (such as iNOS) in the individual. In some embodiments, the level of the pro-inflammatory cytokine or inflammation-induced enzyme is decreased at least about any one of 1.5×, 2×, 3×, 4×, 5×, 6×, 7×, 8×, 9×, 10× or more compared to the level prior to the treatment. In some embodiments, the IL-22 dimer comprises two monomeric subunits, wherein each monomeric subunit comprises an IL-22 domain linked to a dimerization domain via an optional linker. In some embodiments, the dimerization domain comprises at least a portion of an Fc fragment (such as Fc fragment of human IgG). In some embodiments, the IL-22 domain comprises the amino acid sequence of SEQ ID NO: 3. In some embodiments, the Fc fragment comprises the sequence of SEQ ID NO:2 or SEQ ID No:9. In some embodiments, the linker comprises the sequence of SEQ ID NO:1 or SEQ ID NO:10. In some embodiments, the dimerization domain is at the N-terminus of the IL-22 domain. In some embodiments, the dimerization domain is at the C-terminus of the IL-22 domain. In some embodiments, each of the monomeric subunits comprises an amino acid sequence selected from SEQ ID NO:4 and SEQ ID NQs:6-8.

In some embodiments, there is provided a method of promoting differentiation and/or growth of secretory cells (such as goblet cells and/or Paneth cells) in the intestine of an individual (such as a neonate) having necrotizing enterocolitis, comprising administering (such as intravenously administering) to the individual an effective amount of an IL-22, a dimer, or a multimer thereof. In some embodiments, there is provided a method of promoting differentiation and/or growth of secretory cells (such as goblet cells and/or Paneth cells) in the intestine of an individual (such as a neonate) at risk of having necrotizing enterocolitis, comprising administering (such as intravenously administering) to the individual an effective amount of an IL-22, a dimer, or a multimer thereof. In some embodiments, there is provided a method of preventing and/or treating necrotizing enterocolitis in an individual (such as a neonate), comprising administering (such as intravenously administering) to the individual an effective amount of an IL-22, a dimer, or a multimer thereof, wherein the effective amount of IL-22, dimer, or multimer thereof promotes differentiation and/or growth of secretory cells (such as goblet cells and/or Paneth cells) in the intestine of the individual. In some embodiments, the number of the secretory cells (such as goblet cells, or Paneth cells) increase by at least about any one of 1.5×, 2×, 3×, 4×, 5×, 6×, 7×, 8×, 9×, 10× or more compared to the number prior to the treatment. In some embodiments, the IL-22 dimer comprises two monomeric subunits, wherein each monomeric subunit comprises an IL-22 domain linked to a dimerization domain via an optional linker. In some embodiments, the dimerization domain comprises at least a portion of an Fc fragment (such as Fc fragment of human IgG). In some embodiments, the IL-22 domain comprises the amino acid sequence of SEQ ID NO: 3. In some embodiments, the Fc fragment comprises the sequence of SEQ ID NO:2 or SEQ ID No:9. In some embodiments, the linker comprises the sequence of SEQ ID NO:1 or SEQ ID NO:10. In some embodiments, the dimerization domain is at the N-terminus of the IL-22 domain. In some embodiments, the dimerization domain is at the C-terminus of the IL-22 domain. In some embodiments, each of the monomeric subunits comprises an amino acid sequence selected from SEQ ID NO:4 and SEQ ID NOs:6-8.

In some embodiments, there is provided a method of regulating one or more host defense genes (such as up-regulates Defa-ps1, Defa22, Defa29, Reg3g, Reg3b, and/or Reg3d, and/or down-regulates Reg3a, Reg4 and/or Reg1) an individual (such as a neonate) having necrotizing eterocolitis, comprising administering (such as intravenously administering) to the individual an effective amount of an IL-22, a dimer, or a multimer thereof. In some embodiments, there is provided a method of regulating one or more host defense genes (such as up-regulates Defa-ps1, Defa22, Defa29, Reg3g, Reg3b, and/or Reg3d, and/or down-regulates Reg3a, Reg4 and/or Reg1) an individual (such us a neonate) at risk of having necrotizing enterocolitis, comprising administering (such us intravenously administering) to the individual an effective amount of an IL-22, a dimer, or a multimer thereof. In some embodiments, there is provided a method of preventing and/or treating necrotizing enterocolitis in an individual (such as a neonate), comprising administering (such as intravenously administering) to the individual an effective amount of an IL-22, a dimer, or a multimer thereof, wherein the effective amount of the IL-22, dimer, or multimer thereof regulates one or more host defense genes (such as up-regulates Defa-ps1, Defa22, Defa29, Reg3g, Reg3b, and/or Reg3d, and/or down-regulates Reg3a, Reg4 and/or Reg1). In some embodiments, the one or more host defense genes (such as Defa-ps1, Defa22, Defa29, Reg3g, Reg3b, and/or Reg3d) are up-regulated by at least about any of 1.5×, 2×, 3×, 4×, 5×, 6×, 7×, 8×, 9×, 10× compared to the level prior to the treatment. In some embodiments, the one or more host defense genes (such as Reg3a, Reg4 and/or Reg1) are down-regulated by at least about any of 1.5×, 2×, 3×, 4×, 5×, 6×, 7×, 8×, 9×, 10× compared to the level prior to the treatment. In some embodiments, the IL-22 dimer comprises two monomeric subunits, wherein each monomeric subunit comprises an IL-22 domain linked to a dimerization domain via an optional linker. In some embodiments, the dimerization domain comprises at least a portion of an Fc fragment. In some embodiments, the IL-22 domain comprises the amino acid sequence of SEQ ID NO: 3. In some embodiments, the Fc fragment comprises the sequence of SEQ ID NO:2 or SEQ ID No:9. In some embodiments, the linker comprises the sequence of SEQ ID NO:1 or SEQ ID NO:10. In some embodiments, the dimerization domain is at the N-terminus of the IL-22 domain. In some embodiments, the dimerization domain is at the C-terminus of the IL-22 domain. In some embodiments, each of the monomeric subunits comprises an amino acid sequence selected from SEQ ID NO:4 and SEQ ID NOs:6-8.

As used herein, the term "therapy" refers to administration of an IL-22, dimer, or multimer thereof to an individual in need thereof in order to cure, ameliorate, improve, reduce, delay, and/or affect the disease, symptom, or predisposition of the individual.

As used herein, the term "treatment" (and grammatical variations thereof such as "treating" or "treat") is an approach for obtaining beneficial or desired results including clinical results. For purposes of this invention, beneficial or desired clinical results include, but are not limited to, one or more of the following: decreasing one more symptoms resulting from the disease, diminishing the extent of the disease, stabilizing the disease (e.g., preventing or delaying the worsetting of the disease), delay or slowing the progression of the disease, ameliorating the disease state, decreasing the dose of one or more other medications required to treat the disease, increasing the quality of life, and/or prolonging survival. In some variations, the IL-22, dimer or multimer thereof reduces the severity of one or more symptoms associated with necrotizing enterocolitis by at least about any one of 10%, 20%, 30%, 40%, 50%, 60%, 70%, 80%, 90%, 95%, or 100% compared to the corresponding symptom in the same individual prior to treatment or compared to the corresponding symptom in other individuals not receiving the treatment. Also encompassed by "treatment" is a reduction of pathological consequence of necrotizing enterocolitis or other intestinal inflammations.

As used herein, the term "preventing" or "prevent" refers to an approach for avoiding, delaying, or reducing the probability of occurrence, onset, or re-occurrence of a disease.

The term "effective amount" refers to a dose of an IL-22, dimer, or multimer thereof, which can achieve the goal of treatment within the individual in need thereof. It is to be understood by one of ordinary skills in the art that, "therapeutically effective amount" may vary depending on the routes of administration, the types of excipients used and the combination with other medicaments.

The term "individual," "individual to be treated," or "subject" refers to a mammal, such as humans. An individual includes, but is not limited to, human, bovine, horse, feline, canine, rodent, or primate. In some embodiments, the individual is human. In some embodiments, the individual has necrotizing enterocolitis. In some embodiments, the individual is at risk of having necrotizing enterocolitis.

As used herein, an "at risk" individual is an individual who is at risk of developing a disease or condition, such as necrotizing enterocolitis. An individual "at risk" may or may not have detectable disease, and may or may not have displayed detectable disease prior to the treatment methods described herein. "At risk" denotes that an individual has one or more so-called risk factors, which are measurable parameters that correlate with development of the disease (e.g., necrotizing enterocolitis), which are described herein. An individual having one or more of these risk factors has a higher probability of developing the disease (e.g., necrotizing enterocolitis) than an individual without these risk factor(s). For example, a premature infant individual is considered "at risk of having necrotizing enterocolitis" if the premature infant has any one or more (such as any one of 1, 2, 3, 4, 5, 6, 7, 8, 9, 10, or more) of the risk factors of necrotizing enterocolitis, including, but not limited to, low birth weight (e.g., less than about 1000 g), low gestation age (such as birth prior to about 28 weeks), feeding intolerance, formula feeding, use of breast milk fortifier, use of H2 blockers, Chorioamnionitis, sepsis, infections, prolonged (such as more than about 5 days) first course of antibiotics, patent ductus arteriosus, indomethacin treatment, glucocorticoids and indomethacin in first week of life, absence of umbilical arterial catheter, mechanical ventilation, transfusions, HIV-positive mother, antenatal cocaine use, perinatal asphyxia, Apgar score of less than 7 at 5 minutes, Black race, antenatal glucocorticoids, morphine infusion, and vaginal delivery. In some embodiments, a late preterm (such as close to about 37 weeks gestation age) or full-term infant individual is considered "at risk of having necrotizing enterocolitis" if the late preterm or full-term infant has any one or more (such as any of 1, 2, 3, 4, 5, 6, 7, 8, 9, 10, or more) of the risk factors of necrotizing enterocolitis, including, but not limited to, cyanotic congenital heart disease, polycythemia, intrauterine growth restriction, formula feeding, maternal hypertensive disease, HIV-positive mother, umbilical catheters, exchange transfusion, perinatal asphyxia, mechanical ventilation, sepsis, maternal illicit drug use, respiratory distress syndrome, and Apgar score less than 7 at 5 minutes. Exemplary risk factors of necrotizing enterocolitis have been described, for example, in Gephart S M et al., "Necrotizing Enterocolitis Risk," *Adv. Neonatal Care,* 2012; 12(2): 77-89.

The methods described herein are particularly suitable for certain patient populations, such as neonates, preterm infants, and infants having a low birth weight. In some embodiments, the individual is an infant. In some embodiments, the individual is a neonate of no more than about any one of 1 week, 2 weeks, 3 weeks, 4 weeks, 1 month, 2 months, 3 months, 4 months, 5 months, 6 months, or 1 year old. In some embodiments, the individual is a preterm infant. In some embodiments, the individual in a preterm infant, i.e., an infant with a gestation age of no more than about 37 weeks at birth. In some embodiments, the individual is a preterm infant having a gestation age of no more than about any one of 37 weeks, 36 weeks, 35 weeks, 34 weeks, 33 weeks, 32 weeks, 31 weeks, 30 weeks, 29 weeks, 28 weeks, 27 weeks, 26 weeks, or fewer weeks at birth. In some embodiments, the infant is an extremely preterm infant, i.e., an infant having a gestation age of less than about 25 weeks at birth. In some embodiments, the infant is a very preterm infant, i.e., an infant having a gestation age of less than about 32 weeks a birth. In some embodiments, the infant is a moderately preterm infant, i.e., an infant having a gestation age of about 32 weeks to about 34 weeks at birth. In some embodiments, the infant is a late preterm infant, i.e., an infant having a gestation age of about 34 weeks to about 36 weeks at birth. In some embodiments, the infant is a full term infant.

In some embodiments, the individual is an infant with low birth weight. In some embodiments, the individual has a birth weigh of no more than about any one of 2 kg, 1.5 kg, 1.25 kg, 1 kg, 900 g, 800 g, 700 g, 600 g, 590 g, or less. In some embodiments, the individual has a birth weight of about 500 g to about 1000 g. In some embodiments, the individual is a very low birth weight (VLBW) infant, i.e., an infant having a birth weigh of less than about 1500 g. In some embodiments, the individual is an extremely low birth weight infant, i.e., an infant having a birth weight of less than about 1000 g. In some embodiments, the individual is an infant with a birth weight of about 500 g to about 1000 g.

In some embodiments, the individual to be treated has a Bell NEC severity score of 1 or more, of 2 or more, or of 3 or more. See, for example, Bell M J: Neonatal necrotizing enterocolitis. N Engl J Med 298:281-282, 1978. In some embodiments, the individual to be treated is at risk of having NEC. In some embodiments, the individual to be treated is characterized by typical clinical and radiographic features of NEC. In some embodiments, the individual to be treated exhibits one or more of symptoms of necrotizing enterocolitis, including, but not limited to, apnea, bradycardia, temperature instability, abdominal distention, intestinal ileus, bloody stools, abdominal distention, bilious emesis, poor systemic perfusion, pneumatosis intestinalis, peritonitis, abdominal wall edema, crepitus, hypotension, renal failure, thrombocytopenia, pneumoperitoneum, and multiple organ failure.

As described herein, various types of necrotizing enterocolitis can be prevented or treated. In some embodiments, the necrotizing enterocolitis is stage I NEC. In some embodiments, the necrotizing enterocolitis is stage II NEC, the necrotizing enterocolitis is stage III NEC.

In some embodiments, there is provided a method of treating and/or preventing a neonate (e.g., preterm infant or infant having a low birth weight) having necrotizing enterocolitis, comprising administering (such as intravenously administering) to the neonate an effective amount of an IL-22, a dimer, or a multimer thereof. In some embodiments, there is provided a method of treating and/or preventing a neonate (e.g., preterm infant or infant having a low birth weight) having necrotizing enterocolitis, comprising administering (such as intravenously administering) to the neonate an effective amount of an IL-22 dimer comprising two monomeric subunits, wherein each monomeric subunit comprises an IL-22 domain linked to a dimerization domain via an optional linker. In some embodiments, the dimerization domain comprises at least a portion of an Fc fragment (such as Fc fragment of human IgG). In some embodiments, the IL-22 domain comprises the amino acid sequence of SEQ ID NO: 3. In some embodiments, the Dc fragment comprises the sequence of SEQ ID NO:2 or SEQ ID No:9. In some embodiments, the linker comprises the sequence of SEQ ID NO:1 or SEQ ID NO:10. In some embodiments, the dimerization domain is at the N-terminus of the IL-22 domain. In some embodiments, the dimerization domain is at the C-terminus of the IL-22 domain. In some embodiments, each of the monomeric subunits comprises an amino acid sequence selected from SEQ ID NO: 4 and SEQ ID NOs: 6-8. In some embodiments, the neonate is a premature infant. In some embodiments, the neonate is a very low birth weight infant, or an extremely low birth weight infant, such as an infant with a birth weight of about 500 g to about 1000 g.

Necrotizing enterocolitis can be diagnosed and treatment can be assessed with various methods, which include, but are not limited to, abdominal radiography, chest x-ray, computed tomography (CT), magnetic resonance imaging (MRI), or other internal visualization technologies. Additionally, experimental and clinical methods, including, but not limited to, serum hexosaminidase, plasma amylin, serum cytosolic β-glucosidase activity, plasma pro- and anti-inflammatory cytokines, serum creatinine kinase isoenzymes, cerebro-splanchnic oxygenation ratio, GI tonometry, rectosignioid pH monitoring, urinary EGF, D-lactate, or thromboxane, and breath hydrogen, can be used to diagnose or assess the treatment endpoint for necrotizing enterocolitis. See. For example, Schnabl K L et al. "Necrotizing enterocolitis: A multifactorial disease with no cure." *World J. Gastroenterol.* 2008; 14(14): 2142-2161; and Neu J. and Walker W A, "Necrotizing Enterocolitis" *New Eng. J. Med.* 2011: 364 (3): 255-264. Efficacy of treatment can be assessed using any of the NEC diagnosis methods described above to assess one or more endpoints before and after the treatment with IL-22, dimer, or multimer thereof. In some embodiments, inflammation biomarkers, such as TLR4, proinflammatory cytokines (such us IL-6), inflammation-induced enzymes (such as iNOS), and host defense genes (such as anti-microbial peptides) can be assessed, for example, by qRT-PCR, or by immunohistochemistry, in a sample of the individual (e.g., intestine biopsy sample) before or after the treatment to assess the efficacy of the treatment.

IL-22

As used herein, the terms "interleukin 22" and "IL-22" are used interchangeably to broadly refer to any native IL-22 or functional variants thereof, such as IL-22 from any mammalian source, including primates (e.g. humans) and rodents (e.g., mice and rats). The term encompasses "full-length," unprocessed IL-22 as well as any forms of IL-22 that result from processing in the cell. For example, both full-length IL-22 containing the N-terminal leader sequence and the mature form IL-22 are encompassed by the current invention. The leader sequence (or signal peptide) can be the endogenous IL-22 leader sequence or an exogenous leader sequence of another mammalian secretary protein. In certain embodiments, the leader sequence can be from a eukaryotic or prokaryotic secretary protein. The term also encompasses naturally occurring variants of IL-22, e.g., splice variants or allelic variants, and engineered variants of IL-22 having at least about any of 80%, 85%, 86%, 87%, 88%, 89%, 90%, 91%, 92%, 93%, 94%, 95%, 96%, 97%, 98%, 99% or 100% sequence identity with native IL-22. Minor sequence variations especially conservative amino acid substitutions of IL-22 that do not affect the IL-22's function and/or activity (e.g., binding to IL-22 receptor) are also contemplated by the invention. In some embodiments, IL-22 has the same amino acid sequence as the human or murine IL-22 as described by Dumoutier et al. in U.S. Pat. No. 6,359,117. In some embodiments, IL-22 has the same biological activity as naturally occurring IL-22. In some embodiments, IL-22 is human IL-22, recombinant human IL-22, murine IL-22, or recombinant murine IL-22.

Native human IL-22 precursor peptide consists of 179 amino acid residues, while the mature peptide consists of 146 amino acid residues. Dumoutier first reported the IL-22 cloned DNA sequences of mouse and human (Dumoutier, et al., 2000; U.S. Pat. No. 6,359,117 and U.S. Pat. No. 6,274,710). IL-22 is mainly expressed in activated T cells (especially Th17 cells), the lectin-stimulated spleen cells (Duroutier J I 2002), IL-2/IL-12-stimulated NK cells (Wolk. K et al. J. Immunology, 168:5379-5402, 2002), and in a number of organs and tissues, including gut, liver, stomach, kidney, lung, heart, thymus, spleen, upon LPS stimulation, in which an increased expression of IL-22 in those organs and tissues are found. IL-22 carries out its biological function through the combination of IL-22R1 receptor soul IL-10R2 receptor. IL-22R1 is a receptor specific to IL-22 and is expressed in skin, kidney, the digestive system (pancreas, small intestine, liver, large intestine, and colon), and the respiratory system (lung and bronchi). Published researches demonstrated that IL-22 is an immuno-modulator.

"IL-22" also includes pegylated IL-22 and covalently modified IL-22 proteins. For example, the IL-22 in the present invention can be polymerized by the modification with any activated polyethylene glycol (PEG) with molecular weight of 5,000-100,000 for the purpose of prolonging its half-life time. Detailed protocols can be referred to in Greenwald et al., Bioorg. Med. Chem. Lett. 1994, 4, 2465: Caliceti et al., I L Farmaco, 1993, 48,919: Zalipsky and Lee, Poly(Ethylene Glycol) Chemistry: Biotechnical and Biomedical Applications, J. M. Harris, Plenus Press, New York (1992). Multi-arm branched active PEG is preferred (CN ZL02101672.0, WO9932139, PCT/US95/0755, PCT/US94/13013, U.S. Pat. Nos. 4,640,835, 4,496,689, 4,301,144, 4,670,417, 4,791,192, 4,179,337.

As used herein, "IL-22," "IL-22 domain" or "IL-22 monomer" refers to monomeric forms of IL-22, unless indicated otherwise.

IL-22 Dimers and Multimers

In some embodiments, the method comprises administering an IL-22 dimer. In some embodiments, the IL-22 dimer comprises two monomeric subunits, wherein each monomeric subunit comprises an IL-22 domain and a dimerization domain. As used herein, "dimerization domain" refers to a protein domain that links a first IL-22 domain with a second IL-22 domain. allowing the formation of an IL-22 dimer. In some embodiments, the dimerization domain is a monomeric subunit of a dimeric protein or protein fragment, wherein dimerization of two dimerization domains in the IL-22 dimer allows formation of the IL-22 dimer. In some embodiments, the dimerization domain is an Fc fragment. In some embodiments, the dimerization domain is a leucine zipper. In some embodiments, the dimerization domain is albumin, such as human albumin.

In some embodiments, the IL-22 dimer comprises a first IL-22 domain, a dimerization domain, and a second IL-22 domain. In some embodiments, the C terminus of the first IL-22 domain is linked to the N-terminus of the dimerization domain via a first linker. In some embodiments, the N-terminus of the second IL-22 domain is linked to the C-terminus of the dimerization domain via a second linker. In some embodiments, the dimerization domain is a monomeric protein or protein fragment. In some embodiments, the dimerization domain is a peptide linker.

In some embodiments, the method comprises administering an IL-22 multimer (such as trimers, tetramers, etc.) comprising more than two monomeric subunits, wherein each monomeric subunit comprises an IL-22 domain, and a multimerization domain.

In some embodiments, the IL-22 dimer of the present invention has the structure of Formula I:

M1-L-M2            I wherein
M1 is a first monomer of IL-22,
M2 is a second monomer of IL-22, and
L is a fusion moiety connecting said first monomer and said second monomer and disposed therebetween.

In some embodiments according to any of the uses described above, the fusion moiety L is selected from the group consisting of:
(i). a short peptide comprising 3 to 50 amino acids; and
(ii). a polypeptide of Formula II:

-Z-Y-Z-            II wherein,
Y is a carrier protein,
Z is nothing, or a short peptide(s) comprising 1 to 30 amino acids, and
"-" is a chemical bond or a covalent bond.

FIGS. 1-3B illustrate the representative structures of IL-22 dimers of the present invention, in which the carrier protein includes but is not limited to Fc fragments of human IgG (such as IgG1, IgG2, IgG3 or IgG4), and human albumin.

In some embodiments, the IL-22 dimer of the present invention comprises two monomeric subunits, in which each monomeric subunit comprises an IL-22 domain and a dimerization domain. Each monomeric subunit comprises an IL-22 domain linked to a dimerization domain via an optional linker. In some embodiments, the IL-22 domain is directly linked to the dimerization domain. In some embodiments, the IL-22 domain is linked to the dimerization domain via a linker, such as a peptide linker. The IL-22 domain can be at the C terminus or N terminus of the dimerization domain. The carrier protein of the IL-22 dimer is formed by two dimerization domains via dimerization. In some embodiments, the two dimerization domains are dimerized to each other via one or more disulfide bonds. In some embodiments, the number of disulfide bonds between the two dimerization domains is 2 or 4.

In some embodiments, the IL-22 dimer comprises a first IL-22 domain, a second IL-22 domain, and a linker (such as peptide linker) disposed therebetween. An amino acid sequence of an exemplars IL-22 dimer is shown in SEQ ID NO: 5 in which amino acid residues 1-146 represent IL-22, amino acid residues 147-162 represent the linker, and residues 163-308 represent another IL-22.

```
                                              SEQ ID NO: 5
APISSHCRLDKSNFQQPYITNRTFMLAKEASLADNNTDVRLIGEKLF

HGVSMSERCYLMKQVLNFTLEEVLFPQSDRFQPYMQEVVPFLARLSNR

LSTCHIEGDDLHIQRNVQKLKDTVKKLGESGEIKAIGELDLLFMSLR

NACIGSGGGSGGGGSGGGGSAPISSHCRLDKSNFQQPYITNRTFMLA

KEASLADNNTDVRLIGEKLFHGVSMSERCYLMKQVLNFTLEEVLFPQ

SDRFQPYMQEVVPFLARSNRLSTCHIEGDDLHIQRNVQKLKDTVKKL

GESGEIKAIGELDLLFMSLRNACI
```

In some embodiments, the IL-22 dinner comprises at least a portion of an Fc fragment as the dimerization domain. In some embodiments, the dimerization domain is an Fc fragment. In some embodiments, the dimerization domain is an Fc fragment of human IgG, such as IgG1, IgG2, IgG3, or IgG4. The term "Fc region," "Fc domain" or "Fc" refers to a C-terminal non-antigen binding region of an immunoglobulin heavy chain that contains at least a portion of the constant region. The term includes native Fc regions and variant Fc regions. In some embodiments, a human IgG heavy chain Fc region extends from Cys226 to the carboxyl-terminus of the heavy chain. However, the C-terminal lysine (lys447) of the Fc region may or may not be present, without affecting the structure or stability of the Fc region. Unless otherwise Specified herein, numbering of amino acid residues in the IgG or Fc region is according to the EU numbering system for antibodies, also called the EU index, as described in Kabat et al., Sequences of Proteins of Immunological Interest, 5th Ed. Public Health Service, National Institutes of Health, Bethesda, Md. 1991.

In some embodiments, the Fc fragment is an immunoglobulin IgG heavy chain constant region comprising a hinge region (starting at Cys226), an IgG CH2 domain and an IgG CH3 domain. The term "hinge region" or "hinge sequence" as used herein refers to the amino acid sequence located between the globular domains in an antibody, such as the polypeptide between the CH1 domain and the CH2 domain in the heavy chain of an IgG. In some embodiments, the hinge region comprises the amino acid sequence CPPCP (SEQ ID NO: 11), a sequence found in the native IgG1 hinge region. In some embodiments, the IL-22 dimer comprises an IgG4 Fc region (e.g., CH2 and CH3 domains) and a hinge region comprising the CPPCP (SEQ ID NO: 11) sequence to facilitate dimerization. In some embodiments, the hinge region comprises the amino acid sequence ERKCC (SEQ ID NO: 14), a sequence found in the native IgG2 hinge region.

In some embodiments, the Fc fragment starts at the hinge region and extends to the C-terminus of the IgG heavy chain. In certain particular embodiments, the Fc fragment comprises the Fc region of human IgG1, IgG2, IgG3 or IgG4. In some embodiments, the Fc fragment comprises the CH2 and CH3 domain of IgG4. In some embodiments, the Fc fragment comprises the CH2 and CH3 domain of IgG1. In some embodiments, the Fc fragment comprises the CH2 and CH3 domain of IgG2. In some embodiments, the Fc fragment comprises the hinge region comprising SEQ ID NO: 14. In some embodiments, the Fc fragment does not comprise part of the hinge region, such as the first to the fifth amino acid residues of the IgG hinge region. In some embodiments, the Fc fragment comprises a truncated hinge region that has a reduced number of cysteines capable of forming disulfide bonds compared to the wildtype hinge region of an IgG. In some embodiments, the Fc fragment does not comprise SEQ ID NO: 14 in the hinge region. In some embodiments, an Fc fragment comprising a truncated hinge region has a reduced possibility of mismatch in the hinge region. It is understood that conservative amino acid substitutions of the Fc region without affecting the desired structure and/or stability of Fc is contemplated within the scope of the invention.

An amino acid sequence of an exemplary IL-22 monomer with an Fc fragment, which is used to form an exemplary IL-22 dimer, is shown in SEQ ID NO: 4 in which amino acid residues 1-146 represent an IL-22, amino acid residues 147-162 represent the linker, and residues 163-385 represent Fc fragment of human IgG2. A dimer is formed by the two IL-22 monomers with Fc fragment via the coupling of the Fc fragments.

SEQ ID NO: 4
APISSHCRLDKSNFQQPYITNRTFMLAKEASLADNNTDVRLIGEKLFH

GVSMSERCYLMKQVLNFTLEEVLFPQSDRFQPYMQEVVPFLARLSNRL

STCHIEGDDLHIQRNVQKLKDTVKKLGESGEIKAIGELDLLFMSLRNA

CIGSGGGSGGGGSGGGGSVECPPCPAPPVAGPSVFLFPPKPKDTLMIS

RTPEVTCVVVDVSHEDPEVQFNWYVDGVEVHNAKTKPREEQFNSTFRV

VSVLTVVHQDWLNGKEYKCKVSNKGLPASIEKTISKTKGQPREPQVYT

LPPSREEEMTKNQVSLTCLVKGFYPSDIAVEWESNGQPENNYKTTPPM

LDSDGSFFLYSKLTVDKSRWQQGNVFSCSVMHEALHNHYTQKSLSLSP

GK

An amino acid sequence of an exemplary IL-22 monomer with an Fc fragment, which is used to form an exemplary IL-22 dimer, is shown in SEQ ID NO: 6 in which amino acid residues 1-146 represent an IL-22, amino acid residues 147-152 represent the linker, and residues 153-375 represent Fc fragment of human IgG2. A dimer is formed by the two IL-22 monomers with Fc fragment via the coupling of the Fc fragments.

SEQ ID NO: 6
APISSHCRLDKSNFQQPYITNRTFMLAKEASLADNNTDVRLIGEKLFH

GVSMSERCYLMKQVLNFTLEEVLFPQSDRFQPYMQEVVPFLARLSNRL

STCHIEGDDLHIQRNVQKLKDTVKKLGESGEIKAIGELDLLFMSLRNA

CIASTKGPVECPPCPAPPVAGPSVFLFPPKPKDTLMISRTPEVTCVVV

DVSHEDPEVQFNWYVDGVEVHNAKTKPREEQFNSTFRVVSVLTVVHQD

WLNGKEYKCKVSNKGLPASIEKTISKTKGQPREPQVYTLPPSREEEMT

KNQVSLTCLVKGFYPSDIAVEWESNGQPENNYKTTPPMLDSDGSFFLY

SKLTVDKSRWQQGNVFSCSVMHEALHNHYTQKSLSLSPGK

An ammo acid sequence of an IL-22 monomer with an Fc fragment, which is used to form an exemplary IL-22 dimer, is shown in SEQ ID NO: 7 in which amino residues 1-223 represent Fc fragment of human IgG2, amino residues 224-239 represent the linker, and residues 240-385 represent an IL-22. A dimer is formed by the two IL-22 monomers with Fc fragment via the coupling of the Fc fragments.

SEQ ID NO: 7
VECPPCPAPPVAGPSVFLFPPKPKDTLMISRTPEVTCVVVDVSHEDPE

VQFNWYVDGVEVHNAKTKPREEQFNSTFRVVSVLTVVHQDWLNGKEYK

CKVSNKGLPASIEKTISKTKGQPREPQVYTLPPSREEMTKNQVSLTCL

VKGFYPSDIAVEWESNGQPENNYKTTPPMLDSDGSFFLYSKLTVDKSR

WQQGNVFSCSVMHEALHNHYTQKSLSLSPGKGSGGGSGGGGSGGGGSA

PISSHCRLDKSNPQQPYITNRTFMLAKEASLADNNTDVRLIGEKLFHG

VSMSERCYLMKQVLNFTLEEVLFPQSDRFQPYMQEVVPFLARLSNRLS

TCHIEGDDLHIQRNVQKLKDTVKKLGESGEIKAIGELDLLFMSLRNAC

I

An amino acid sequence of an IL-22 monomer with an Fc fragment, which is used to form an exemplary IL-22 dimer, is shown in SEQ ID NO: 8 in which amino acid residues 1-223 represent Fc fragment of human IgG2, amino acid residues 224-229 represent the linker, and residues 230-375 represent an IL-22. A dimer is formed by the two IL-22 monomers with Fc fragment via the coupling of the Fc fragments.

SEQ ID NO: 8
VECPPCPAPPVAGPSVFLFPPKPKDTLMISRTPEVTCVVVDVSHEDP

EVQFNWYVDGVEVHNAKTKPREEQFNSTFRVVSVLTVVHQDWLNGKE

YKCKVSNKGLPASIEKTISKTKGQPREPQVYTLPPSREEMTKNQVSL

TCLVKGFYPSDIAVEWESNGQPENNYKTTPPMLDSDGSFFLYSKLTV

DKSRWQQGNVFSCSVMHEALHNHYTQKSLSLSPGKASTKGPAPISSH

CRLDKSNFQQPYITNRTFMLAKEASLADNNTDVRLIGEKLFHGVSMS

ERCYLMKQVLNFTLEEVLFPQSDRFQPYMQEVVPFLARLSNRLSTCH

IEGDDLHIQRNVQKLKDTVKKLGESGEIKAIGELDLLFMSLRNACI

As used herein, the term "linker peptide," "peptide linker," or "linker" refers to an oligo peptide disposed between one IL-22 monomer and the carrier protein, or one IL-22 monomer (or IL-22 domain) and a dimerization domain, and connecting the two domains/fragments together. There is no special restriction on the length of the linker. A linker is usually 5-50 amino acid residues in length. In general, a linker does not affect or significantly affect the proper fold and conformation formed by the configuration of the two IL-22 monomers.

In some embodiments, the linker comprises an amino acid sequence selected from:
(a). an amino acid sequence with 3-16 hydrophobic amino acid residues Gly or Pro, such as Gly-Pro-Gly-Pro-Gly-Pro (SEQ ID NO: 12);
(b). an amino acid sequence encoded by multiple cloning sites. Such sequences usually contain 5-20 amino acid residues, preferably, 10-20 ammo acid residues;
(c). an amino acid sequence of a protein other than IL-22 monomer, such as an amino acid sequence of IgG or albumin; and
(d). an amino acid sequence comprising any combination of (a), (b), and (c) above.

In some embodiments, the linker has the sequence of GSGGGSGGGGSGGGGS (SEQ ID NO: 1) or ASTKGP (SEQ ID NO: 10).

In addition, an amino acid sequence not affecting the biological activity of IL-22 monomer can be added to the N-terminus or C-terminus of the IL-22 monomer, or monomeric subunit. In some embodiments, such appended amino acid sequence is beneficial to expression (e.g. signal peptide), purification (e.g. 6× His tag, the cleavage site of Saccharomyces cerevisiae α-factor signal peptide (Glu-Lys-Arg, SEQ ID NO: 13), and/or enhancement of biological activity of the IL-22, dimer or multimer thereof.

In some embodiments, the IL-22 dimer comprises two monomeric subunits, wherein each monomeric subunit comprises an IL-22 domain and a dimerization domain. In some embodiments, the IL-22 domain is fused to the N-terminus of the dimerization domain. In some embodiments, the IL-22 domain is fused to the C-terminus of the dimerization domain. In some embodiments, the IL-22 domain is directly linked to the dimerization domain. In some embodiments, the IL-22 domain and the dimerization domain are linked via a linker (for example a peptide linker of about 5 to about 50 amino acids in length, for example a linker having the sequence of SEQ ID NO: 10). In some embodiments, the dimerization domain of IL-22 dimer comprises a leucine zipper.

In some embodiments, the IL-22 dimer comprises two monomeric subunits, wherein each monomeric subunit comprises an IL-22 monomer and at least a portion of an immunoglobulin Fc fragment ("the Fc fragment", also referred herein as "Fc region"). In some embodiments, the IL-22 domain is fused to the N-terminus of the Fc fragment. In some embodiments, the IL-22 domain is fused to the C-terminus of the Fc fragment. In some embodiments, the IL-22 domain is directly linked to the Fc fragment. In some embodiments, the IL-22 domain and the Fc fragment are linked via a linker (for example a peptide linker of about 5 to about 50 amino acids in length, for example a linker having the sequence of SEQ ID NO: 1 or SEQ ID NO: 10). In some embodiments, the IL-22 domain has the sequence of SEQ ID NO:3. In some embodiments, the Fc fragment comprises at least two cysteines capable of forming intermolecular disulfide bonds. In some embodiments, the number of disulfide bonds between the Fc fragments is 2 or 4. In some embodiments, the Fc fragment is truncated at the N-terminus, e.g., lacks the first 1, 2, 3, 4, 5, 6, 7, 8, 9, or 10 amino acids of a complete immunoglobulin Fc domain. In some embodiments, the Fc fragment is derived from IgG2. In some embodiments, the Fc fragment is derived from IgG4. In some embodiments, the Fc fragment has the sequence of SEQ ID NO:2 or SEQ ID NO: 9.

(Fc Fragment)
SEQ ID NO: 2
VECPPCPAPPVAGPSVFLFPPKPKDTLMISRTPEVTCVVVDVSHEDP

EVQFNWYVDGVEVHNAKTKPREEQFNSTFRVVSVLTVVHQDWLNGKE

YKCKVSNKGLPASIEKTISKTKGQPREPQVYTLPPSREEMTKNQVSL

TCLVKGFYPSDIAVEWESNGQPENNYKTTPPMLDSDGSFFLYSKLTV

DKSRWQQGNVFSCSVMHEALHNHYTQKSLSLSPGK (IL-22 domain)
SEQ ID NO: 3
APISSHCRLDKSNFQQPYITNRTFMLAKEASLADNNTDVRLIGEKLF

HGVSMSERCYLMKQVLNFTLEEVLFPQSDRFQPYMQEVVPFLARLSN

RLSTCHIEGDDLHIQRNVQKLKDTVKKLGESGEIKAIGELDLLFMSL

RNACI (Fc Fragment)
SEQ ID NO: 9
ERKCCVECPPCPAPPVAGPSVFLFPPKPKDTLMISRTPEVTCVVVDV

SHEDPEVQFNWYVDGVEVHNAKTKPREEQFNSTFRVVSVLTVVHQDW

LNGKEYKCKVSNKGLPASIEKTISKTKGQPREPQVYTLPPSREEMTK

NQVSLTCLVKGFYPSDISVEWESNGQPENNYKTTPPMLDSDGSFFLY

SKLTVDKSRWQQGNVFSCSVMHEALHNHYTQKSLSLSPGK

In some embodiments, the IL-22 dimer comprises two monomeric subunits, wherein each monomeric subunit comprises (e.g., consists of) the sequence of SEQ ID NO:4. In some embodiments, the IL-22 dimer comprises two monomeric subunits, wherein each monomeric subunit comprises (e.g., consists of) the sequence of SEQ ID NO:6. In some embodiments, the IL-22, dimer comprises two monomeric subunits, wherein each monomeric subunit comprises (e.g., consists of) the sequence of SEQ ID NO:7. In some embodiments, the IL-22 dimer comprises two monomeric subunits, wherein each monomeric subunit comprises (e.g., consists of) the sequence of SEQ ID NO:8.

The invention encompasses modifications to the polypeptides described herein, including functionally equivalent proteins which do not significantly affect their properties and variants which have enhanced or decreased activity. Modification of polypeptides is routine practice in the art and need not be described in detail herein. Examples of modified polypeptides include polypeptides with conservative substitutions of amino acid residues, one or more deletions or additions of amino acids which do not significantly and deleteriously change the functional activity, non-conservative mutations which do not significantly and deleteriously change the functional activity, or use of chemical analogs.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an N-terminal methionyl residue or an epitope tag. Other insertional variants of the monomeric subunits include the fusion to the N- or C-terminus of the polypeptide, or a polypeptide which increases the serum half-life of the IL-22 dimer.

Twenty amino acids are commonly found in proteins. Those amino acids can be grouped into nine classes or groups based on the chemical properties of their side chains. Substitution of one amino acid residue for another within the same class or group is referred to herein as a "conservative" substitution. Conservative amino acid substitutions can frequently be made in a protein without significantly altering the conformation or function of the protein. In contrast, non-conservative amino acid substitutions tend to disrupt conformation and function of a protein. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). (See Table 1 below.)

TABLE 1

Examples of amino acid classification

| | |
|---|---|
| Small/Aliphatic residues: | Gly, Ala, Val, Leu, Ile |
| Cyclic Imino Acid: | Pro |
| Hydroxyl-containing Residues: | Ser, Thr |
| Acidic Residues: | Asp, Glu |
| Amide Residues: | Asn, Gln |
| Basic Residues: | Lys, Arg |
| Imidazole Residues: | His |
| Aromatic Residues: | Phe, Tyr, Trp |
| Sulfur-containing Residues: | Met, Cys |

In some embodiments, the conservative amino acid substitution comprises substituting any of glycine (G), alanine (A), isoleucine (I), valine (V), and leucine (L) for any other of these aliphatic amino acids; serine (S) for threonine (T) and vice versa; aspartic acid (D) for glutamic acid (E) and vice versa; glutamine (Q) for asparagine (N) and vice versa; lysine (K) for arginine (R) and vice versa; phenylalanine (F), tyrosine (Y) and tryptophan (W) for any other of these aromatic amino acids; and methionine (M) for cysteine (C) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pKs of these two amino acid residues am not significant. Still other changes can be considered "conservative" in particular environments (see. e.g., Biochemistry at pp. 13-15, 2nd ed. Lubert Stryer ed. (Stanford University): Henikoff et al., Proc. Nat'l Acad. Sci. USA (1992) 89:10915-10919; Lei et al., J. Biol. Chem. (1995) 270(20):11882-11886).

In some embodiments, the IL-22 dimer has a serum half-life that is significantly longer than that of an IL-22 monomer (such as native IL-22). In some embodiments, the IL-22 dimer as a serum half-life of at least about any one of 15, 30, 50, 100, 150, 200, 250, 300, 350 or more hours. In some embodiments, while the dose of IL-22 dimer is about 2 µg/kg, the serum half-life is at least about any one of 15, 30, 50, 100, 150, or 200 hours. In some embodiments, while the dose of IL-22 dimer is about 10 µg/kg, the serum half-life is at least about any of 50, 100, 150, or 200 hours. In some embodiments, while the dose of IL-22 dimer is about 30 µg/kg, the serum half-life is at least about any one of 100, 150, 200, or 250 hours. In some embodiments, while the dose of IL-22 dimer is about 45 µg/kg, the serum half-life is at least about any of 100, 150, 200, 250, 300, or 350 hours.

Preparation of IL-22, Dimers, or Multimers Thereof

The IL-22, dimers, or multimers thereof may be expressed using recombinant DNA technology. The nucleotide sequence encoding an IL-22, or an IL-22 monomeric subunit can be inserted into a replicable cloning or protein expression vector at restriction sites using known techniques. In some embodiments, a single nucleotide sequence encoding an IL-22, or an IL-22 monomeric subunit is inserted into a cloning or expression vector. In some embodiments, a nucleotide sequence encoding the IL-22 domain and a nucleotide sequence encoding the extension peptide region may be separately inserted into a cloning or expression vector in such a manner that when the nucleotide sequence is expressed as a protein, a continuous polypeptide is formed. In some embodiments, a nucleotide sequence encoding a linker, a nucleotide sequence encoding a dimerization domain, and a nucleotide sequence encoding an IL-22 domain may be separately inserted into a cloning or expression vector in such a manner that when the nucleotide sequence is expressed as a protein, a continuous polypeptide is formed. In some embodiments, the nucleotide sequence encoding an IL-22, or an IL-22 monomeric subunit may be fused to a nucleotide sequence encoding an affinity or identification tag, such as, but not limited to, a His-tag, FLAG-tag, SUMO-tag, GST-tag, antibody-tag, or MBP-tag. In some embodiments, the clotting or expression vector may be then transfected or transformed into eukaryotic or prokaryotic cells using known techniques. In some embodiments, IL-22, or monomeric subunits may be expressed in vitro.

The expression host cell may be any cell able to express IL-22, monomeric subunits, IL-22 dimers or IL-22 multimers. Suitable prokaryotic expression host cells may include, but are not limited to, *Escherichia coli, Erwinia, Klesbsiella,*

*Proteus, Salmonella, Serratia, Shigella, Bacillus subtilis, Bacillus licheniformis, Pseudomonas*, and *Streptomyces*. Eukaryotic cell, such as fungi or yeast, may also be suitable for expression of the monomeric subunits, for example, but not limited to, *Saccharomyces, Schizosaccharomyces pombe, Kluyveromyces lactis, Kluyveromyces fragilis, Kluyveromyces waltii, Kluyveromyces drosophilarum, Kluyveromyces thermotolerans, Kluyveromyces murxianus, Pichia pastoris, Neurospora crassa, Schwanniomyces, Penicillium, Tolypocladium, Synechococcus* and *Aspergillus*. Plant or algal cells may also be suitable for expression of IL-22 or monomeric subunits, such as *Chlanydomonas*. Eukaryotic cell derived from multicellular organisms may also be suitable for expression of IL-22, or monomeric subunits, for example, but not limited to, invertebrate cells such as *Drosophila* S2 and *Spodoptera* Sf9, or mammalian cells such as Chinese Hamster Ovary (CHO) cells, COS cells, human embryonic kidney cells (such as HEK293 cells), murine testis trophoblastic cells, human lung cells, and murine breast cancer cells. After the IL-22, or IL-22 monomeric subunit cloning plasmid is transformed or transfected into a host cell, the host cells can be grown on conventional nutrient media and protein expression induced, if necessary. In some embodiments, the expression of IL-22 or monomeric subunits does not require inducement.

In some embodiments, expressed monomeric subunits form IL-22 dimers or multimers. In some embodiments, monomeric subunits require further inducement, such as by supplying an oxidation compound (such as hydrogen peroxide or a catalytic metal), UV light, or a chemical cross-linker (such as formaldehyde, 1,6-bismaleimidohexane, 1,3-dibromo-2-propanol, bis(2-chloroethyl)sulfide, or glutaraldehyde), to form IL-22 dimers or multimers.

In some embodiments, the formation of IL-22 dimers or multimers does not require inducement. In some embodiments, host cell used to express IL-22, monomeric subunits, IL-22 dimers, or IL-22 multimers is Chinese Hamster Ovary (CHO) cell. The IL-22, monomeric subunits, IL-22 dimers, or IL-22 multimers may be purified using any number of protein purification technique. For example, the IL-22, monomeric subunits, IL-22 dimers, or IL-22 multimers may be purified using affinity chromatography, ion exchange chromatography, reverse-phase HPLC, size-exclusion chromatography, precipitation, or ultracentrifugation. In some embodiments, an affinity tag fused to the IL-22 or IL-22 monomeric subunit polypeptide is removed.

Exemplary preparation methods of IL-22 dimers have been described, for example, in international patent application publication WO2012028089A1 (Application No. PCT/CN2011/079124 filed by Generon (Shanghai) Corporation. LTD on Aug. 30, 2011), incorporated herein by reference.

Administration of IL-22, Dimers, or Multimers Thereof

The IL-22, dimers, or multimers thereof described herein can be administered to an individual via various routes. In some embodiments, the IL-22, dimer, or multimer thereof is administered parenterally, intravenously, orally, intramuscularly, or subcutaneously.

In some embodiments, the IL-22, dimer or multimer is administered intravenously. In some embodiments, the IL-22, dimer or multimer is administered by intravenous push (IVP). In some embodiments, the IL-22, dimer or multimer is administered by intravenous infusion. In some embodiments, the IL-22, dimer or multimer is administered by continuous intravenous infusion.

In some embodiments, the individual is a mammal, such as human, rodents, or primates. In some embodiments, the individual is human.

The effective amount, suitable dose, and dosing schedule of the IL-22, dimers, or multimers thereof administered to an individual (such as human) can vary depending on the particular composition, the method of administration, and the particular type of necrotizing enterocolitis being treated. The dose should be sufficient to effect a desirable response, such as a therapeutic or prophylactic response against a particular disease (e.g., NEC). In some embodiments, an effective amount is an amount sufficient to delay the development of NEC. In some embodiments, an effective amount in an amount sufficient to prevent occurrence and/or recurrence of NEC. An effective amount can be administered in one or more administrations. Suitable dosage of the IL-22, IL-22 dimer, or IL-22 multimer includes, for example, about 0.5 µg/kg to about 500 µg/kg, about 1 µg/kg to about 200 µg/kg, about 2 µg/kg to about 200 µg/kg, about 1 µg/kg to about 100 µg/kg, about 5 µg/kg to about 80 µg/kg, about 10 µg/kg to about 45 µg/kg, and about 30 µg/kg to about 40 µg/kg.

In some embodiments, the IL-22, dimer, or multimer thereof is administered once every week. In some embodiments, the IL-22, dimer, or multimer thereof is administered once every 2, 3, 4, 5, 6, 7, 8, 9, 10, 11, 12, or 24 weeks. In some embodiments, the IL-22, dimer, or multimer thereof is administered once every 1, 2, 3, 4, 5, 6, 7, 8, 9, 10, or 12 months. In some embodiments, the IL-22 dimer is administered only once.

In some embodiments, the IL-22 dimer is administered intravenously at the dose of at least about any one of 1 µg/kg, 2 µg/kg, 5 µg/kg, 10 µg/kg, 20 µg/kg, 30 µg/kg, 40 µg/kg, or 50 µg/kg. In some embodiments, the IL-22 dimer is administered intravenously at the dose of no more than about any one of 100 µg/kg, 50 µg/kg, 40 µg/kg, 30 µg/kg, 20 µg/kg, 10 µg/kg, 5 µg/kg, or 1 µg/kg. In some embodiments, the IL-22 dimer is administered to the individual at about 1 µg/kg to about 100 µg/kg. In some embodiments, the IL-22 dimer is administered no more frequently than once every wee, once every month, once every two months, or once every six months.

Kits and Medicines

Also provided are kits, medicines, unit dosage, or products suitable for any one of the methods described herein. For example, in some embodiments, there is provided a kit comprising an IL-22, a dimer, or a multimer thereof and an instruction for using the IL-22, dimer, or multimer thereof for preventing and/or treating necrotizing enterocolitis.

The IL-22, dimer, or multimer thereof described herein can be formulated with pharmaceutically acceptable excipients or carriers for use in treating and/or preventing necrotizing enterocolitis.

The pharmaceutical composition of the present invention comprises a safe and effective amount of said IL-22, dimer, or multimer thereof, or a pharmaceutically acceptable salt, and a pharmaceutically acceptable excipient or carrier. "Safe and effective amount" refers to an amount of a compound or agent sufficient to substantially improve the condition of the patient in need thereof without causing serious side-effects. The safe and effective amount is determined based on the specific circumstances such as age, condition, and regimen associated with an individual receiving the treatment.

"Pharmaceutically acceptable excipient or carrier" refers to one or more compatible solid or liquid filling or gelatin materials which are suitable to be used in human with sufficient purity and sufficiently low toxicity. "Compatibility" refers to the ability of each ingredient of the composition to mutually blend with the compound of the present invention and the mutual blending ability between the ingredients, without substantially decreasing the clinical efficacy of the compound. Some of the examples of pharmaceutically acceptable excipient or carrier include cellulose and its derivatives (e.g. sodium carboxymethylcellulose, sodium ethylcellulose, cellulose acetate, etc.), gelatin, speckstone, solid lubricating agent (e.g. stearic acid, magnesium stearate), calcium sulphate, plant oil (e.g. pea oil, sesame oil, peanut oil, olive oil, etc.), polyols (e.g. propylene glycol, glycerol, mannitol, sorbitol, etc.), emulsifier (e.g. Tween®), wetting agent (e.g. sodium lauryl sulfate), colorant, flavoring agent, stabilizer, anti-oxidant, antiseptic, pyrogen-free water, etc.

Suitable routes of administration of the IL-22, dimer, or multimer thereof of the present application include, but are not limited to, oral administration, rectal administration, parenteral administration (intravenous, intramuscular, or subcutaneous), and local administration.

Exemplary solid forms of the pharmaceutical composition for oral administration include capsules, tablets, pills, powder, and granules. In these solid forms, active agent is mixed with at least one of the conventionally inert excipients (or carriers), such as sodium citrate, dicalcium phosphate, or any of the following ingredients: (a) filing or bulking agent, e.g. starch, lactose, sucrose, glucose, mannitol, and silicic acid; (b) adhesion agent, e.g. carboxymethylcellulose, alginate, gelatin, polyvinyl pyrrolidone, sucrose, and acacia; (c) humectants, e.g. glycerol; (d) disintegrating agent, e.g. agar, calcium carbonate, potato starch or cassava starch, alginic acid, compounded silicate, and sodium carbonate; (e) buffering agent, e.g. paraffin wax; (f) absorption accelerating agent, e.g. quaternary amine compound; (g) wetting agent, e.g. cetanol and glycerin monostearate; (h) absorbent, e.g. bolus alba; and (i). lubricating agent, e.g. speckstone, calcium stearate, magnesium stearate, solid polyethylene glycol, sodium lauryl sulfate, or any mixture thereof. Capsules, tablets, and pills can also comprise a buttering agent.

Solid forms such as tablets, sugar pill, capsules, pills, and granules can be prepared with coating and core-shell materials, such as casing and other materials known in the art. These materials can comprise opacifying agent and the active compound or compound in such composition can be released in a delayed fashion that the release is done in certain part of the alimentary canal. Embedding component such as polymer materials and wax materials can be used. If desired, active compounds can be mixed with one or more of the above-described excipients to formulate a micro capsule form.

Exemplary liquid forms of the pharmaceutical composition described herein for oral administration comprise pharmaceutically acceptable emulsion, solution, suspension, syrup, or tincture. Apart from active compounds, liquid forms can also comprise inert diluents conventionally used in the art such as water or other solvent, solubilizing agent and emulsifier such as ethanol, isopropanol, carbonate acetate, ethyl acetate, propan-2-ol,1,3-butan-2-ol, dimethyl-fomamide, and oil, in particular cotton oil, peanut oil, maize embryo oil, olive oil, caster oil, and sesame oil or any mixture thereof.

Apart from these inert diluents, the composition can also comprise additives, such as wetting agent, emulsifying agent, suspending agent, sweetening agent, correctives, and spices.

Apart from active compounds, suspension can also comprise suspending agent, such as ethoxyl isostearic alcohol, polyoxyethylene sorbitol, sorbitan, microcrystalline cellulose, aluminum methoxide, agar, or any mixture thereof.

Compositions used for parenteral administration can also comprise physiologically acceptable liquid combinations such as sterile water or anhydrous solution, dispersion solution, suspension, or emulsion, etc. Appropriate hydrated or anhydrous carriers, diluting agent, solvent, or excipient comprise water, ethanol, polyols (such as propylene glycol, polyethylene glycol, glycerinum, etc.), and appropriate mixtures thereof, are described in Chinese Pharmacopeia or the other countries' Pharmacopeias. Preferably, the liquid compositions can also comprise pharmaceutically acceptable additives commonly used, provided that the additives should not inhibit the functions of IL-22, dimers, or multimers thereof. The representative additives include (but are not limited to): buffer, PH adjuster, and the like.

Compositions used for parenteral administration can also comprise sterilized powder (for example, lyophilized powder) that can be reconstituted to an injectable solution or dispersal solution. Preferably, the lyophilized powder can also comprise pharmaceutically acceptable additives commonly used, provided that the additives should not inhibit the functions of IL-22, dimers, or multimers thereof. The representative additives include (but are not limited to): buffer, PH adjuster. Preferably, the solvents used to dissolve the lyophilized powder include (but are not limited to) glucose solution, sodium chloride solution.

In some embodiments, the IL-22 dimer described herein can be administered intravenously, for example, by intravenous push or intravenous infusion.

Forms of the IL-22, dimer, or multimer thereof of the present invention used for topical administration compose ointment, powder, patch, sprayer, and inhalant. Under sterile conditions, active components can be mixed with physiologically acceptable carrier and any antiseptic, buffering agent, or propellant if desired.

The IL-22, dimer, or multimer thereof of the present invention can be solely administered or be administered in conjunction with any other pharmaceutically acceptable compounds or agents.

Micro-capsules containing the IL-22, dimer, or multimer thereof of the present invention can be used as a sustained release system. Sustained release micro-capsule system of recombinant protein has been successfully applied to recombinant human growth hormone (rhGH), recombinant human interferon (rhIFN), IL-2 and MNrgp120 (Johnson et al., Nat. Med., 2:795-799 (1996): Yasuda, Biomed. Ther 27:1221-1223 (1993); WO 97/03692, WO 96/40072, WO 96/07399; U.S. Pat. No. 5,654,010).

The sustained release system of the IL-22, dimer, or multimer thereof of the present application can be prepared with poly(lactic-co-glycolic acid) (PLGA) which has good biologically compatibility and broad biological degradability. Lactic acid and glycolic acid, the degrading products of PLGA, can be cleared quickly in human body. Furthermore, the degradability of that polymer can vary from several months to several years depending on its molecular weight and composition (Lewis, "Controlled release of bioactive agents form lactide/glycolide polymer," in: M. Chasin and R. Langer (Eds.), Biodegradable Polymers as Drug Delivery Systems (Marcel Dekker: New York, 1990), pp. 1-41)).

The dosage and concentration of the pharmaceutical composition of the present invention can be adjusted according to actual use situations. One skilled in the art should know how to choose the suitable dosage and route of administration according to practical needs. The principle for adjusting between different species such as mice and human can be seen in Mordenti, J. and Chappell, W. "The use of interspecies sealing in toxicokinetics" In Toxicokinetics and New Drug Development, Yacobi et al.: Pergamon Press, New York 1989, pp. 42-96.

Also provided are articles of manufacture comprising the compositions described herein in suitable packaging. Suitable packaging for compositions described herein are known in the art, and include, for example, vials (such as sealed vials), vessels (such as sealed vessels), ampules, bottles, jars, flexible packaging (e.g., scaled Mylar or plastic bags), and the like. These articles of manufacture may further be sterilized and/or sealed. Also provided are unit dosage forms comprising the compositions described herein. These unit dosage forms can be stored in a suitable packaging in single or multiple unit dosages and may also be further sterilized and sealed.

The present invention also provides kits comprising compositions (or unit dosages forms and/or articles of manufacture) described herein and may further comprise instruction(s) on methods of using the composition, such as uses further described herein. In some embodiments, the kit of the invention comprises the packaging described above. The kits described herein may further include other materials desirable from a commercial and user standpoint, including other buffers, diluents, filters, needles, syringes, and package inserts with instructions for performing any methods described herein.

The following exemplary embodiments further describe the present invention. Although the description referred to particular embodiments, it will be clear to one skilled in the art that the present invention may be practiced with variation of these specific details. Hence this invention should not be construed as limited to the embodiments set forth herein. Further, for the embodiments in which details of the experimental methods are not described, such methods are carried out according to conventional conditions such as those described in Sambrook et al. Molecular Cloning: A Laboratory Manual (New York: Cold Spring Harbor Laboratory Press, 1989), or as suggested by the manufacturers.

EXAMPLES

The examples below are intended to be purely exemplary of the invention and should therefore not be considered to limit the invention in any way. The following examples and detailed description are offered by way of illustration and not by way of limitation.

Example 1. Role of IL-22RA1 Signaling in Gut Barrier Maintenance

IL-22RA1 (IL-22 receptor alpha 1) is a component of the IL-22 receptor, which is expressed on epithelial tissues. Intestinal-specific LL22RA1 knockout mice (referred herein as IL-22RA1$^{\Delta IEC}$ mice) were generated by crossing IL-22RA1$^{fl/fl}$ ×villin-cre mice in order to investigate the effects of IL-22RA1 signaling on intestinal immune response.

Figure 4:
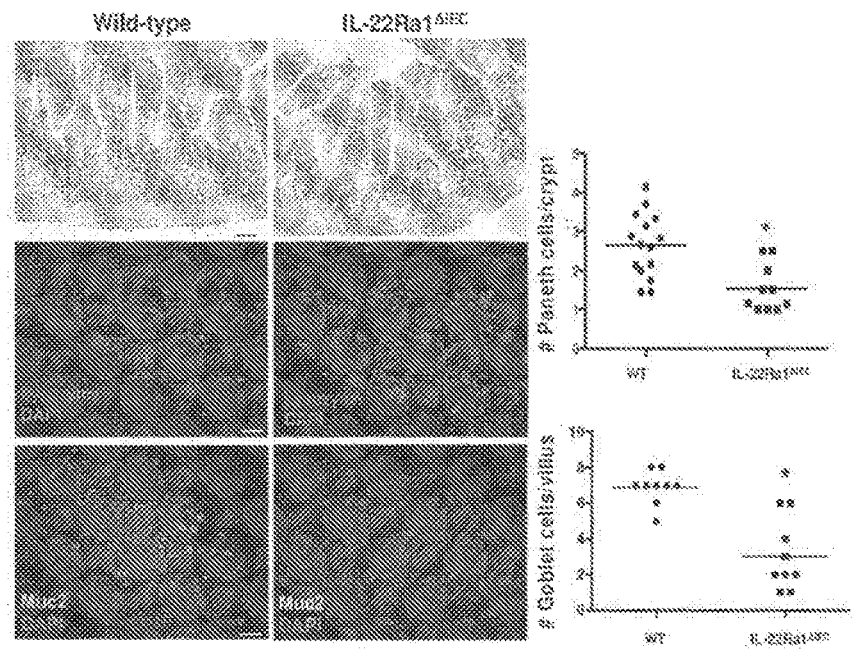
FIG. 4 shows confocal microscopy images and quantifications of Paneth cells and goblet cells in the small intestine of wildtype and intestinal IL-22Ra1 deficient mice. Top panel of the images show H&E staining results. Middle panel of the images show immunostaining results against lysozyme (red) that is secreted by Paneth cells, and nuclei (DAPI, blue). Bottom panel of the images show immunostaining results against Muc2 (red) that is secreted by goblet cells, and nuclei (DAPI, blue).

As shown in FIG. 4, compared to wildtype mice, mice deficient in intestinal IL-22RA1 signaling had significantly decreased numbers of goblet cells and Paneth cells in the small intestine. Therefore, IL-22RA1 signaling regulates the number of secretory cells in the small intestine.

Figure 5:
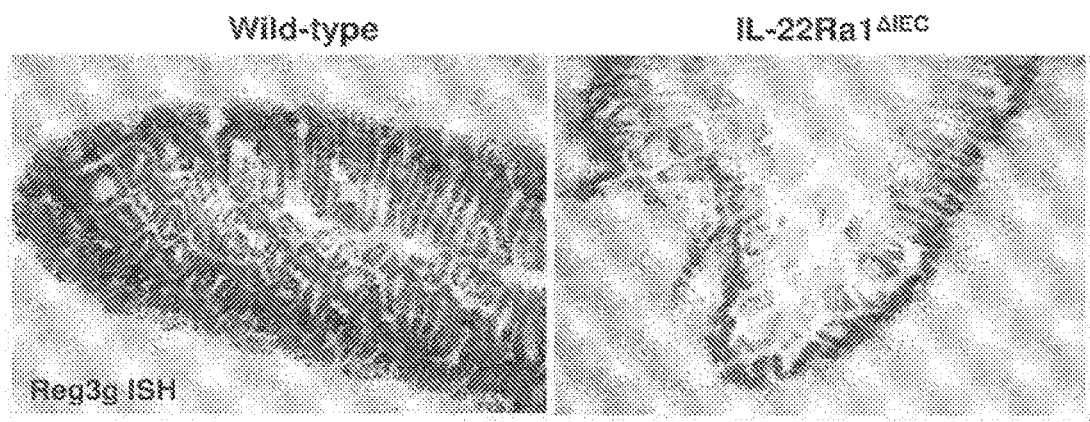
FIG. 5 shows in situ hybridization against Reg3g, an antimicrobial peptide secreted by Paneth cells, in intestine samples of wildtype (left panel) and intestinal IL-22Ra1 deficient mice (right panel).

Paneth cells are located at the bottom of the intestinal crypts, and they produce large amounts of antimicrobial peptides, such as lysozyme and Reg3g. FIG. 5 shows results of an in situ hybridization experiment with probes against Reg3g mRNA in intestine samples from wildtype and IL-22RA1$^{\Delta IEC}$ mice. Compared to wildtype mice, IL-22RA1$^{\Delta IEC}$ mice had significantly reduced Reg3g expression levels in the intestine.

Without being bound by any theory or hypothesis, IL-22RA1 signaling regulates the number of goblet cells and Paneth cells by promoting intestinal stem cell development. The secretory cells in the intestine are key effectors of innate mucosal defense that maintain the integrity of the gut barrier. Therefore, IL-22RA1 and IL-22 signaling serve important roles in gut barrier maintenance.

Example 2. IL-22 Dimer Protects Intestinal Epithelial Cells against Inflammation In Vitro This example investigates in vitro protective effects of an exemplary IL-22 dimer against inflammation of intestinal epithelial cells (IEC-6 cells). The IL-22 dimer comprises two monomeric subunits each comprising an IL-22 domain and an Fc domain (also referred herein as "rIL-22"). The exemplary IL-22 dimer consisted of two monomeric subunits each comprising the amino acid sequence of SEQ ID NO: 4.

IEC-6 cells were subjected to the following four groups of conditions: (1) Control group: IEC-6 cells were cultured in medium, and not treated with the IL-22 dimer or lipopolysaccharide (LPS); (2) LPS group: IEC-6 cells were cultured in medium, and then stimulated with LPS; (3) rIL-22 group: IEC-6 cells were pre-treated with the IL-22 dimer, and then cultured in medium; and (4) LPS+rIL-22 group: IEC-6 cells were pre-treated with the IL-22 dimer, and then stimulated with LPS. Inflammatory response of the IEC-6 cells in each group was assessed by monitoring nuclear translocation of NF-kB using immunostaining and confocal microscopy, and by measuring the expression levels of IL-6 (a pro-inflammatory cytokine) using qRT-PCR. RPLO was used as a control gene in the qRT-PCR experiments.

Figure 6A:
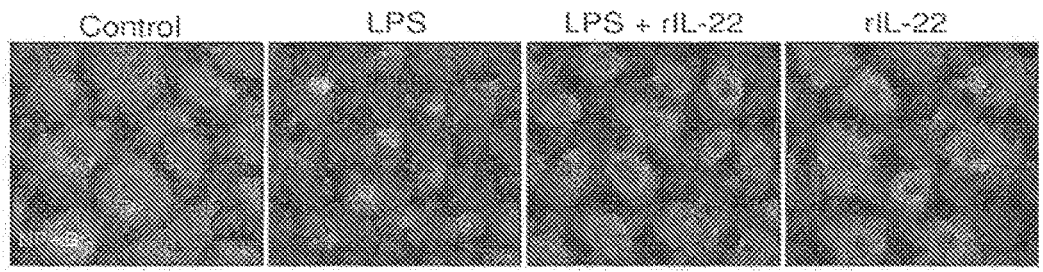
FIG. 6A shows cellular distribution of NP-κB (green) in IEC-6 cells under various conditions.

As shows in FIG. 6A, LPS stimulation of IEC-6 cells led to a significant level of nuclear translocation of NF-kB (second panel from the left). Pre-treatment of the IEC-6 cells with the IL-22 dimer effectively prevented nuclear translocation of NF-kB n response to LPS stimulation (third panel from the left).

Figure 6B:
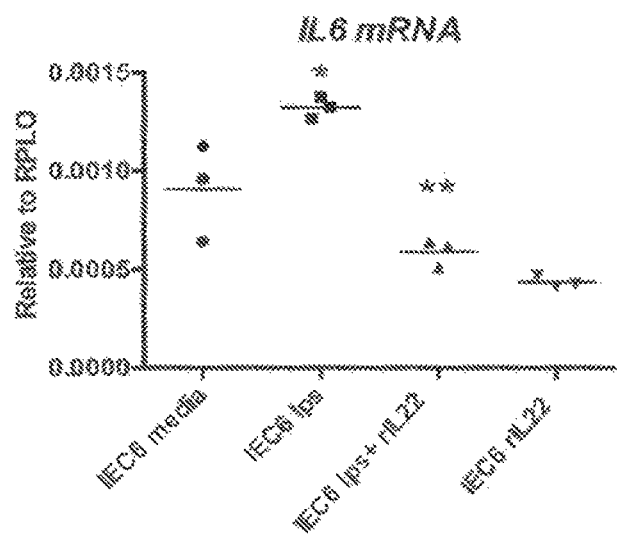
FIG. 6B shows qRT-PCR results of IL-6 expression in IEC-6 cells under various conditions.

As shown in FIG. 6B, LPS stimulation of IEC-6 cells led to an increased expression level of the pro-inflammatory cytokine IL-6 as compared to the control group (P<0.05). Pre-treatment with the IL-22 dimer significantly reduced the IL-6 expression level as compared to the LPS group (P<0.05).

The results demonstrate that the IL-22 dimer inhibits NF-kB nuclear translocation and IL-6 expression in intestinal epithelial cells in vitro. As NF-κB and IL-6 are downstream effectors of the TLR-4 signaling pathway in inflammatory response, the IL-22 dimer can protect intestinal epithelial cells from inflammation by inhibiting TLR-4 signaling.

Example 3. IL-22 Dimer Promotes Growth of Goblet Cells and Expression of Host Defense Genes in enteroids Ex Vivo This example investigates immunoprotective effects of an exemplary IL-22 dimer (i.e., rIL-22) on mice and human enteroids. Intestinal stem cells were isolated from the crypts of small intestinal tissues of untreated B6 wildtype mice and 20-week human fetal tissues respectively. The Intestinal stem cells were cultured for 5 days to provide enteroids, which were treated with either the IL-22 dimer or media alone (control) for 24 hours.

Figure 7:
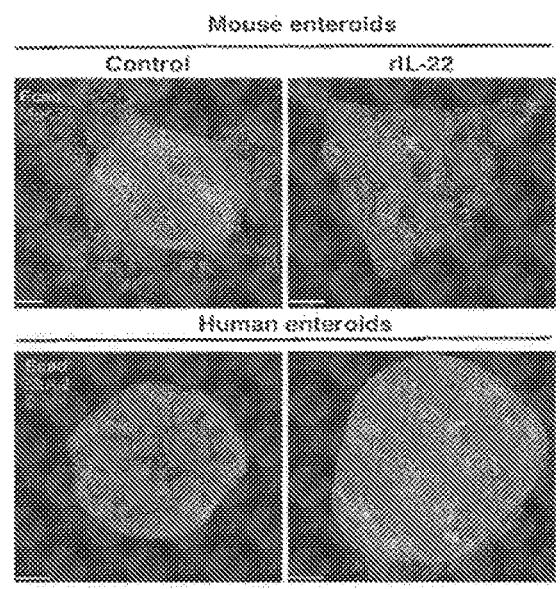

The numbers of goblet cells and enterocytes in the enteroids were assessed by immunohistochemistry and confocal microscopy. As shown in FIG. 7, goblet cells were stained against Muc-2 (red), enterocytes were stained against E-cadherin (green), and nuclei were stained using DAPI (blue). The results demonstrate that the IL-22 dimer promoted growth of the enterocytes and differentiation of the intestinal stem cells into goblet cells in both human and mice enteroids.

Figure 8:
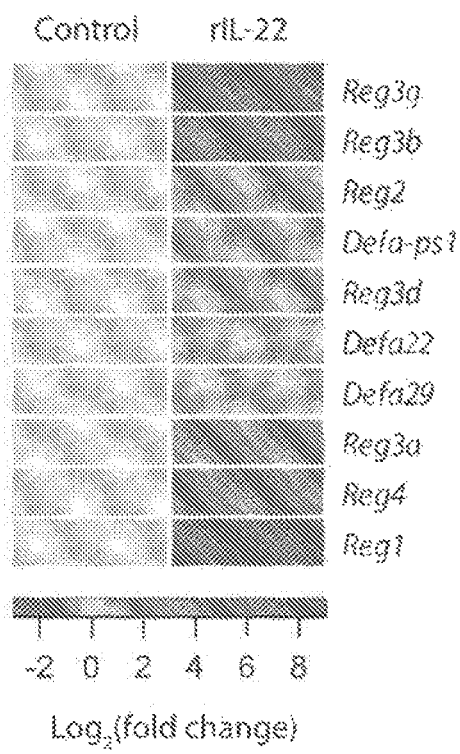

Additionally, RNA sequencing was performed on murine enteroid samples of the IL-22 dimer treatment group and control group. Expression levels of host defense genes in the two groups were compared. As shown in FIG. 8, many host defense genes were differentially regulated in enteroids treated with the IL-22 dimer as compared to the control enteroids. For example, α-defensins (such as Defa-ps1, Defa22, and Defa29) and other antimicrobial peptides (such as Reg3g, Reg3b, and Reg3d) were upregulated in the IL-22 dimer treated enteroids. Reg3a, Reg4 and Reg1 were down-regulated in the IL-22 dimer treated enteroids.

The results demonstrate that the IL-22 dimer can promote differentiation and growth of goblet cells, and regulate the expression of how defense genes in mice and human enteroids. Secretory cells in the intestine, such as goblet cells, and the antimicrobial peptides secreted thereof, play important roles in gut barrier maintenance and preventing or treating NEC.

Example 4. IL-22 Dimer Protects Intestinal Epithelial Cells against Inflammation In Vivo In this example, neonatal wildtype mice (7-10 day old) were administered lipopolysaccharide (LPS) by formula gavage, and treated with either IgG (control) or an exemplary IL-22 dimer (i.e., rIL-22) via intraperitoneal injection twice per week on postnatal days 10-28. Inflammatory response in the terminal ileum of mice in the IL-22 dimer treatment group and the control group was assessed by quantification of secretory cells (i.e., goblet cells and Paneth cells using immunohistochemistry, and by measuring the expression levels of TLR4 using qRT-PCR. RPLO was used as a control gene in the qRT-PCR experiments.

Figure 9:
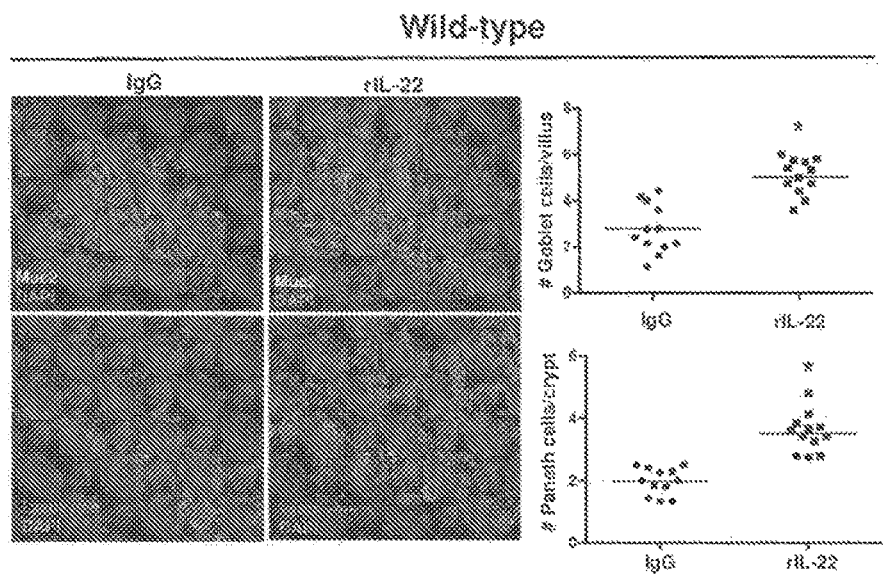
Figure 10:
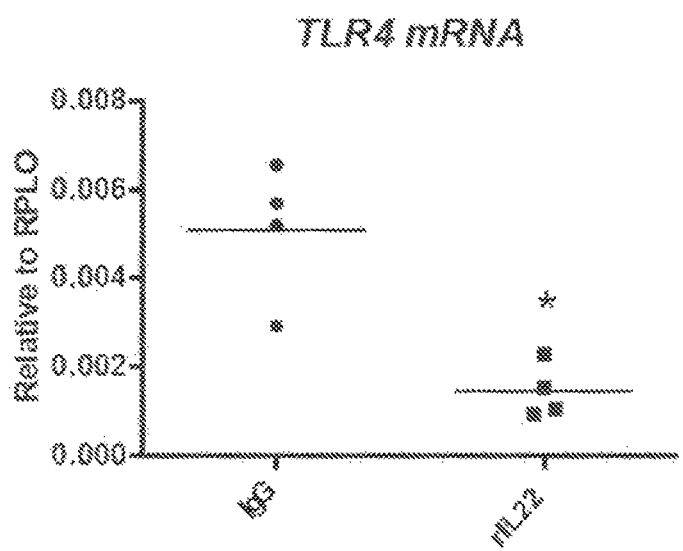

As shown in FIG. 9, compared to IgG-treated mice, mice treated with the IL-22 dimer had significantly larger numbers of goblet cells (stained against Muc2) and Paneth cells (stained against lysozyme) in the terminal ileum (P<0.05). Thus, treatment with the IL-22 dimer can increase the number of secretory cells in the intestines of mice, which is beneficial in maintaining the gut barrier, and preventing or treating NEC.

Additionally, compared to the IgG treatment group, wildtype mice treated with the IL-22 dimer had significantly lower expression levels of TLR4 (P=0.005). Thus, treatment with the IL-22 dimer inhibits TLR4 signaling in vivo, suggesting that the IL-22 dimer may protect intestine epithelial cells against TLR4-mediated diseases, such as NEC.

The results suggest that the IL-22 dimer may be effective in preventing NEC in neonatal mice.

Example 5. In Vivo Efficacy of IL-22 Dimer in Treating a Murine Model of Necrotizing Enterocolitis In this example, a murine model of necrotizing enterocolitis (NEC) was established and treated with as exemplary IL-22 dimer (i.e., rIL-22). The efficacy of the IL-22 dimer was assessed by comparing the severity of NEC in the IL-22 dimer treatment group, the induced NEC group, and the control group.

Methods

Induction of Necrotizing Enterocolitis in Neonatal Mice

All animal experiments were approved by the University of Pittsburgh Animal Care and Use Committee. Experimental NEC was induced in 7-10 day old mice as previously described (see, for example, Sodhi C P, Neal M D, Siggers R, et al. "Intestinal epithelial Toll-like receptor 4 regulates goblet cell development and is required for necrotizing enterocolitis in mice." *Gastroenterology* 2012;143:708-18 el-5: and Afraza A. Sodhi C P Good M. et al. "Intracellular heat shock protein-70 negatively regulates TLR4 signaling in the newborn intestinal epithelium." *J Immunol* 2012;188: 4543-57). Briefly, formula gavage [Similac Advance infant formula (Abbott Nutrition. Columbus, Ohio):Esbilac (PetAg, Hampshire, Ill.) canine milk replacer 2:1, 50 µL/gram body weight] was administered to mice in the induced NEC group five times per day, wherein the formula gavage was supplemented with enteric bacteria obtained from infants with severe NEC (see, for example, Good M, Sodhi C P, Ozolek J A. et al. "Lactobacillus rhamnosus HN001 decreases the severity of necrotizing enterocolitis in neonatal mice and preterm piglets: evidence in mice for a role of TLR9." *Am J Physiol Gastrointest Liver Physiol* 2014;306:G1021-32). In addition, the mice in the induced NEC group received 10 minutes of hypoxia (5% $O_2$, 95% $N_2$) via a chamber (Billups-Rothenberg, Del Mar, Calif.) twice a day for 4 days. Mice in the control group were breast fed, and not exposed to the enteric bacteria from infants with severe NEC. In the IL-22 dimer treatment group, mice with induced NEC were administered the IL-22 dimer by intraperitoneal injection at a dose of 1 µg/gram body weight once daily for the duration of the model.

NEC Severity Assessment

Mouse terminal ileal sections were assessed by histology for the degree of mucosal injury according to out previously published scoring system (see, for example, Anand R J, Leaphart C L, Mollen K P, et al. "The role of the intestinal barrier in the pathogenesis of necrotizing enterocolitis." *Shock* 2007;27:124-33) from 0 (normal) to 3 (severe injury), gross morphology, weight loss, and by expression of pro-inflammatory cytokines and inflammation-induced enzymes (such as inducible nitric oxide synthase, i.e., iNOS) by qRT-PCR.

Results

Figure 11A:
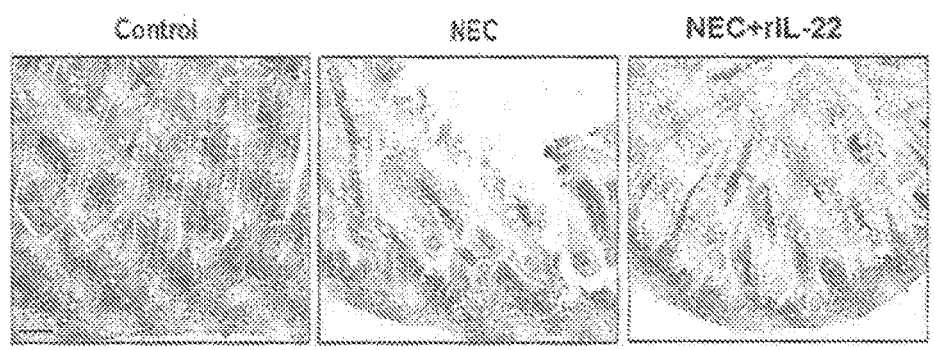
FIG. 11A shows H&E staining of terminal ileum of mice in the control group, induced NEC group, or IL-22 dimer treated NEC group.
Figure 11B:
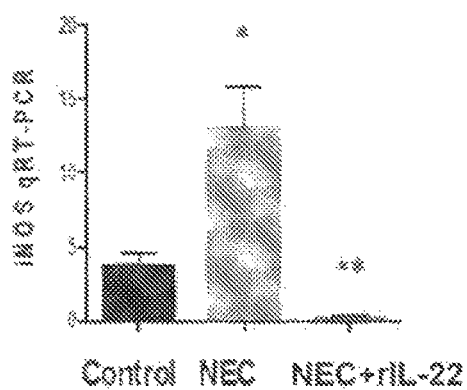

As shown in FIG. 11A, the intestine of mice with induced NEC showed severe mucosal injury, including patchy ulceration of the mucosa and submucosa in association with massive necrosis, as compared to the control group. Treatment with the IL-22 dimer significantly improved the intestinal morphology of the NEC mice.

Additionally, the expression levels of inflammation-induced enzyme iNOS were significantly higher in mice with induced NEC as compared to the control group (P<0.05), indicating elevated inflammatory response to the induced NEC group. Treatment with the IL-22 dimer greatly reduced the iNOS expression level in mice with induced NEC (P<0.05, as compared to the induced NEC group), suggesting a repressed inflammation level in the IL-22 dimer treated NEC mice.

The results demonstrate that the IL-22 dimer can attenuate the severity of NEC in the murine model. Thus, the IL-22 dimer has therapeutic efficacy in the murine model of NEC.

All references mentioned in the present invention are incorporated herein by reference as if each of those references has been incorporated by reference individually.

What is claimed is:

1. A method of treating necrotizing enterocolitis (NEC) in an individual, comprising administering to the individual an effective amount of an IL-22, a dimer, or a multimer thereof, wherein the individual is an infant.

2. The method of claim 1, wherein the NEC is stage I NEC, stage II NEC, or stage III NEC.

3. The method of claim 1, wherein the individual is a preterm infant.

4. The method of claim 1, wherein the effective amount of the IL-22, dimer, or multimer thereof results in inhibition of TLR4 in the individual.

5. The method of claim 1, wherein the effective amount of the IL-22, dimer, or multimer thereof results in inhibition of one or more pro-inflammatory cytokines and/or inflammation-induced enzymes in the individual.

6. The method of claim 1, wherein the effective amount of the IL-22, dimer, or multimer thereof promotes differentiation and/or growth of secretory cells in the intestine of the individual.

7. The method of claim 1, wherein the effective amount of the IL-22, dimer, or multimer thereof regulates one or more host defense genes in the individual selected from the group consisting of Defa-ps1, Defa22, Defa29, Reg3g, Reg3b, Reg3d, Reg3a, Reg4, and Reg1.

8. The method of claim 1, comprising administering to the individual an effective amount of an IL-22 dimer.

9. The method of claim 8, wherein the IL-22 dimer is administered at the effective amount of about 1 µg/kg to about 200 µg/kg.

10. The method of claim 9, wherein the IL-22 dimer is administered at the effective amount of about 5 µg/kg to about 80 µg/kg.

11. The method of claim 8, wherein the IL-22 dimer comprises two monomeric subunits, wherein each monomeric subunit comprises an IL-22 domain and a dimerization domain linked via a linker.

12. The method of claim 11, wherein the linker comprises the sequence of SEQ ID NO: 1 or 10.

13. The method of claim 11, wherein the dimerization domain comprises at least two cysteines capable of forming intermolecular disulfide bonds.

14. The method of claim 11, wherein the dimerization domain comprises at least a portion of an Fc fragment.

15. The method of claim 14, wherein the Fc fragment comprises CH2 and CH3 domains.

16. The method of claim 14, wherein the Fc fragment comprises the sequence of SEQ ID NO: 2 or 9.

17. The method of claim 11, wherein the IL-22 domain of each of the monomeric subunits comprises the sequence of SEQ ID NO: 3.

18. The method of claim 11, wherein the dimerization domain is at the N-terminus of the IL-22 domain within each monomeric subunit.

19. The method of claim 11, wherein the dimerization domain is at the C-terminus of the IL-22 domain within each monomeric subunit.

20. The method of claim 11, wherein each of the monomeric subunits comprises an amino acid sequence selected from the group consisting of SEQ ID NOs: 4 and 6-8.

21. The method of claim 1, wherein the IL-22, dimer, or multimer thereof is administered intravenously.

* * * * *

```
                          SEQUENCE LISTING

<160> NUMBER OF SEQ ID NOS: 14

<210> SEQ ID NO 1
<211> LENGTH: 16
<212> TYPE: PRT
<213> ORGANISM: Artificial Sequence
<220> FEATURE:
<223> OTHER INFORMATION: short peptide

<400> SEQUENCE: 1

Gly Ser Gly Gly Gly Ser Gly Gly Gly Ser Gly Gly Gly Gly Gly Ser
1               5                   10                  15

<210> SEQ ID NO 2
<211> LENGTH: 223
<212> TYPE: PRT
<213> ORGANISM: Artificial Sequence
<220> FEATURE:
<223> OTHER INFORMATION: IgG2 Fc

<400> SEQUENCE: 2

Val Glu Cys Pro Pro Cys Pro Ala Pro Pro Val Ala Gly Pro Ser Val
1               5                   10                  15

Phe Leu Phe Pro Pro Lys Pro Lys Asp Thr Leu Met Ile Ser Arg Thr
                20                  25                  30

Pro Glu Val Thr Cys Val Val Val Asp Val Ser His Glu Asp Pro Glu
            35                  40                  45

Val Gln Phe Asn Trp Tyr Val Asp Gly Val Glu Val His Asn Ala Lys
        50                  55                  60

Thr Lys Pro Arg Glu Glu Gln Phe Asn Ser Thr Phe Arg Val Val Ser
65                  70                  75                  80

Val Leu Thr Val Val His Gln Asp Trp Leu Asn Gly Lys Glu Tyr Lys
                85                  90                  95

Cys Lys Val Ser Asn Lys Gly Leu Pro Ala Ser Ile Glu Lys Thr Ile
            100                 105                 110

Ser Lys Thr Lys Gly Gln Pro Arg Glu Pro Gln Val Tyr Thr Leu Pro
        115                 120                 125

Pro Ser Arg Glu Glu Met Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205
```

His Asn His Tyr Thr Gln Lys Ser Leu Ser Leu Ser Pro Gly Lys
    210                 215                 220

<210> SEQ ID NO 3
<211> LENGTH: 146
<212> TYPE: PRT
<213> ORGANISM: Artificial Sequence
<220> FEATURE:
<223> OTHER INFORMATION: IL_22

<400> SEQUENCE: 3

Ala Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
            20                  25                  30

Ala Asp Asn Asn Thr Asp Val Arg Leu Ile Gly Glu Lys Leu Phe His
        35                  40                  45

Gly Val Ser Met Ser Glu Arg Cys Tyr Leu Met Lys Gln Val Leu Asn
    50                  55                  60

Phe Thr Leu Glu Glu Val Leu Phe Pro Gln Ser Asp Arg Phe Gln Pro
65                  70                  75                  80

Tyr Met Gln Glu Val Val Pro Phe Leu Ala Arg Leu Ser Asn Arg Leu
                85                  90                  95

Ser Thr Cys His Ile Glu Gly Asp Asp Leu His Ile Gln Arg Asn Val
            100                 105                 110

Gln Lys Leu Lys Asp Thr Val Lys Lys Leu Gly Glu Ser Gly Glu Ile
        115                 120                 125

Lys Ala Ile Gly Glu Leu Asp Leu Leu Phe Met Ser Leu Arg Asn Ala
    130                 135                 140

Cys Ile
145

<210> SEQ ID NO 4
<211> LENGTH: 385
<212> TYPE: PRT
<213> ORGANISM: Artificial Sequence
<220> FEATURE:
<223> OTHER INFORMATION: IL_22_linker_IgG2 Fc

<400> SEQUENCE: 4

Ala Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
            20                  25                  30

Ala Asp Asn Asn Thr Asp Val Arg Leu Ile Gly Glu Lys Leu Phe His
        35                  40                  45

Gly Val Ser Met Ser Glu Arg Cys Tyr Leu Met Lys Gln Val Leu Asn
    50                  55                  60

Phe Thr Leu Glu Glu Val Leu Phe Pro Gln Ser Asp Arg Phe Gln Pro
65                  70                  75                  80

Tyr Met Gln Glu Val Val Pro Phe Leu Ala Arg Leu Ser Asn Arg Leu
                85                  90                  95

Ser Thr Cys His Ile Glu Gly Asp Asp Leu His Ile Gln Arg Asn Val
            100                 105                 110

Gln Lys Leu Lys Asp Thr Val Lys Lys Leu Gly Glu Ser Gly Glu Ile
        115                 120                 125

Lys Ala Ile Gly Glu Leu Asp Leu Leu Phe Met Ser Leu Arg Asn Ala
    130                 135                 140

```
Cys Ile Gly Ser Gly Gly Ser Gly Gly Gly Ser Gly Gly Gly
145                 150                 155                 160

Gly Ser Val Glu Cys Pro Cys Pro Ala Pro Pro Val Ala Gly Pro
            165                 170                 175

Ser Val Phe Leu Phe Pro Pro Lys Pro Lys Asp Thr Leu Met Ile Ser
            180                 185                 190

Arg Thr Pro Glu Val Thr Cys Val Val Val Asp Val Ser His Glu Asp
            195                 200                 205

Pro Glu Val Gln Phe Asn Trp Tyr Val Asp Gly Val Glu Val His Asn
            210                 215                 220

Ala Lys Thr Lys Pro Arg Glu Glu Gln Phe Asn Ser Thr Phe Arg Val
225                 230                 235                 240

Val Ser Val Leu Thr Val Val His Gln Asp Trp Leu Asn Gly Lys Glu
            245                 250                 255

Tyr Lys Cys Lys Val Ser Asn Lys Gly Leu Pro Ala Ser Ile Glu Lys
            260                 265                 270

Thr Ile Ser Lys Thr Lys Gly Gln Pro Arg Glu Pro Gln Val Tyr Thr
            275                 280                 285

Leu Pro Pro Ser Arg Glu Glu Met Thr Lys Asn Gln Val Ser Leu Thr
290                 295                 300

Cys Leu Val Lys Gly Phe Tyr Pro Ser Asp Ile Ala Val Glu Trp Glu
305                 310                 315                 320

Ser Asn Gly Gln Pro Glu Asn Asn Tyr Lys Thr Thr Pro Pro Met Leu
            325                 330                 335

Asp Ser Asp Gly Ser Phe Phe Leu Tyr Ser Lys Leu Thr Val Asp Lys
            340                 345                 350

Ser Arg Trp Gln Gln Gly Asn Val Phe Ser Cys Ser Val Met His Glu
            355                 360                 365

Ala Leu His Asn His Tyr Thr Gln Lys Ser Leu Ser Leu Ser Pro Gly
            370                 375                 380

Lys
385

<210> SEQ ID NO 5
<211> LENGTH: 308
<212> TYPE: PRT
<213> ORGANISM: Artificial Sequence
<220> FEATURE:
<223> OTHER INFORMATION: IL_22_linker_IL_22

<400> SEQUENCE: 5

Ala Pro Ile Ser Ser His Cys Arg Leu Asp Lys Ser Asn Phe Gln Gln
1               5                   10                  15

Pro Tyr Ile Thr Asn Arg Thr Phe Met Leu Ala Lys Glu Ala Ser Leu
            20                  25                  30

Ala Asp Asn Asn Thr Asp Val Arg Leu Ile Gly Glu Lys Leu Phe His
            35                  40                  45

Gly Val Ser Met Ser Glu Arg Cys Tyr Leu Met Lys Gln Val Leu Asn
        50                  55                  60

Phe Thr Leu Glu Glu Val Leu Phe Pro Gln Ser Asp Arg Phe Gln Pro
65                  70                  75                  80

Tyr Met Gln Glu Val Val Pro Phe Leu Ala Arg Leu Ser Asn Arg Leu
                85                  90                  95

Ser Thr Cys His Ile Glu Gly Asp Asp Leu His Ile Gln Arg Asn Val
            100                 105                 110
```

-continued

```
Gln Lys Leu Lys Asp Thr Val Lys Lys Leu Gly Glu Ser Gly Glu Ile
            115                 120                 125
Lys Ala Ile Gly Glu Leu Asp Leu Leu Phe Met Ser Leu Arg Asn Ala
        130                 135                 140
Cys Ile Gly Ser Gly Gly Ser Gly Gly Gly Ser Gly Gly Gly
145                 150                 155                 160
Gly Ser Ala Pro Ile Ser Ser His Cys Arg Leu Asp Lys Ser Asn Phe
                165                 170                 175
Gln Gln Pro Tyr Ile Thr Asn Arg Thr Phe Met Leu Ala Lys Glu Ala
            180                 185                 190
Ser Leu Ala Asp Asn Asn Thr Asp Val Arg Leu Ile Gly Glu Lys Leu
        195                 200                 205
Phe His Gly Val Ser Met Ser Glu Arg Cys Tyr Leu Met Lys Gln Val
    210                 215                 220
Leu Asn Phe Thr Leu Glu Glu Val Leu Phe Pro Gln Ser Asp Arg Phe
225                 230                 235                 240
Gln Pro Tyr Met Gln Glu Val Val Pro Phe Leu Ala Arg Leu Ser Asn
                245                 250                 255
Arg Leu Ser Thr Cys His Ile Glu Gly Asp Asp Leu His Ile Gln Arg
            260                 265                 270
Asn Val Gln Lys Leu Lys Asp Thr Val Lys Lys Leu Gly Glu Ser Gly
        275                 280                 285
Glu Ile Lys Ala Ile Gly Glu Leu Asp Leu Leu Phe Met Ser Leu Arg
    290                 295                 300
Asn Ala Cys Ile
305
```

<210> SEQ ID NO 6
<211> LENGTH: 375
<212> TYPE: PRT
<213> ORGANISM: Artificial Sequence
<220> FEATURE:
<223> OTHER INFORMATION: IL_22_linker_IgG2 Fc

<400> SEQUENCE: 6

```
Ala Pro Ile Ser Ser His Cys Arg Leu Asp Lys Ser Asn Phe Gln Gln
1               5                   10                  15
Pro Tyr Ile Thr Asn Arg Thr Phe Met Leu Ala Lys Glu Ala Ser Leu
            20                  25                  30
Ala Asp Asn Asn Thr Asp Val Arg Leu Ile Gly Glu Lys Leu Phe His
        35                  40                  45
Gly Val Ser Met Ser Glu Arg Cys Tyr Leu Met Lys Gln Val Leu Asn
    50                  55                  60
Phe Thr Leu Glu Glu Val Leu Phe Pro Gln Ser Asp Arg Phe Gln Pro
65                  70                  75                  80
Tyr Met Gln Glu Val Val Pro Phe Leu Ala Arg Leu Ser Asn Arg Leu
                85                  90                  95
Ser Thr Cys His Ile Glu Gly Asp Asp Leu His Ile Gln Arg Asn Val
            100                 105                 110
Gln Lys Leu Lys Asp Thr Val Lys Lys Leu Gly Glu Ser Gly Glu Ile
        115                 120                 125
Lys Ala Ile Gly Glu Leu Asp Leu Leu Phe Met Ser Leu Arg Asn Ala
    130                 135                 140
Cys Ile Ala Ser Thr Lys Gly Pro Val Glu Cys Pro Pro Cys Pro Ala
145                 150                 155                 160
```

Pro Pro Val Ala Gly Pro Ser Val Phe Leu Phe Pro Lys Pro Lys
                165                 170                 175

Asp Thr Leu Met Ile Ser Arg Thr Pro Glu Val Thr Cys Val Val Val
            180                 185                 190

Asp Val Ser His Glu Asp Pro Glu Val Gln Phe Asn Trp Tyr Val Asp
        195                 200                 205

Gly Val Glu Val His Asn Ala Lys Thr Lys Pro Arg Glu Glu Gln Phe
    210                 215                 220

Asn Ser Thr Phe Arg Val Val Ser Val Leu Thr Val Val His Gln Asp
225                 230                 235                 240

Trp Leu Asn Gly Lys Glu Tyr Lys Cys Lys Val Ser Asn Lys Gly Leu
                245                 250                 255

Pro Ala Ser Ile Glu Lys Thr Ile Ser Lys Thr Lys Gly Gln Pro Arg
            260                 265                 270

Glu Pro Gln Val Tyr Thr Leu Pro Pro Ser Arg Glu Glu Met Thr Lys
        275                 280                 285

Asn Gln Val Ser Leu Thr Cys Leu Val Lys Gly Phe Tyr Pro Ser Asp
    290                 295                 300

Ile Ala Val Glu Trp Glu Ser Asn Gly Gln Pro Glu Asn Asn Tyr Lys
305                 310                 315                 320

Thr Thr Pro Pro Met Leu Asp Ser Asp Gly Ser Phe Phe Leu Tyr Ser
                325                 330                 335

Lys Leu Thr Val Asp Lys Ser Arg Trp Gln Gln Gly Asn Val Phe Ser
            340                 345                 350

Cys Ser Val Met His Glu Ala Leu His Asn His Tyr Thr Gln Lys Ser
        355                 360                 365

Leu Ser Leu Ser Pro Gly Lys
    370                 375

<210> SEQ ID NO 7
<211> LENGTH: 385
<212> TYPE: PRT
<213> ORGANISM: Artificial Sequence
<220> FEATURE:
<223> OTHER INFORMATION: IgG2 Fc_linker_IL_2

<400> SEQUENCE: 7

Val Glu Cys Pro Pro Cys Pro Ala Pro Pro Val Ala Gly Pro Ser Val
1               5                   10                  15

Phe Leu Phe Pro Pro Lys Pro Lys Asp Thr Leu Met Ile Ser Arg Thr
                20                  25                  30

Pro Glu Val Thr Cys Val Val Val Asp Val Ser His Glu Asp Pro Glu
            35                  40                  45

Val Gln Phe Asn Trp Tyr Val Asp Gly Val Glu Val His Asn Ala Lys
        50                  55                  60

Thr Lys Pro Arg Glu Glu Gln Phe Asn Ser Thr Phe Arg Val Val Ser
65                  70                  75                  80

Val Leu Thr Val Val His Gln Asp Trp Leu Asn Gly Lys Glu Tyr Lys
                85                  90                  95

Cys Lys Val Ser Asn Lys Gly Leu Pro Ala Ser Ile Glu Lys Thr Ile
            100                 105                 110

Ser Lys Thr Lys Gly Gln Pro Arg Glu Pro Gln Val Tyr Thr Leu Pro
        115                 120                 125

Pro Ser Arg Glu Glu Met Thr Lys Asn Gln Val Ser Leu Thr Cys Leu
    130                 135                 140

```
Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys Gly
    210                 215                 220

Ser Gly Gly Gly Ser Gly Gly Gly Ser Gly Gly Gly Gly Ser Ala
225                 230                 235                 240

Pro Ile Ser Ser His Cys Arg Leu Asp Lys Ser Asn Phe Gln Gln Pro
                245                 250                 255

Tyr Ile Thr Asn Arg Thr Phe Met Leu Ala Lys Glu Ala Ser Leu Ala
                260                 265                 270

Asp Asn Asn Thr Asp Val Arg Leu Ile Gly Glu Lys Leu Phe His Gly
            275                 280                 285

Val Ser Met Ser Glu Arg Cys Tyr Leu Met Lys Gln Val Leu Asn Phe
        290                 295                 300

Thr Leu Glu Glu Val Leu Phe Pro Gln Ser Asp Arg Phe Gln Pro Tyr
305                 310                 315                 320

Met Gln Glu Val Val Pro Phe Leu Ala Arg Leu Ser Asn Arg Leu Ser
                325                 330                 335

Thr Cys His Ile Glu Gly Asp Asp Leu His Ile Gln Arg Asn Val Gln
                340                 345                 350

Lys Leu Lys Asp Thr Val Lys Lys Leu Gly Glu Ser Gly Glu Ile Lys
            355                 360                 365

Ala Ile Gly Glu Leu Asp Leu Leu Phe Met Ser Leu Arg Asn Ala Cys
370                 375                 380

Ile
385

<210> SEQ ID NO 8
<211> LENGTH: 375
<212> TYPE: PRT
<213> ORGANISM: Artificial Sequence
<220> FEATURE:
<223> OTHER INFORMATION: IgG2 Fc_linker_IL_22

<400> SEQUENCE: 8

Val Glu Cys Pro Pro Cys Pro Ala Pro Pro Val Ala Gly Pro Ser Val
1               5                   10                  15

Phe Leu Phe Pro Pro Lys Pro Lys Asp Thr Leu Met Ile Ser Arg Thr
                20                  25                  30

Pro Glu Val Thr Cys Val Val Val Asp Val Ser His Glu Asp Pro Glu
            35                  40                  45

Val Gln Phe Asn Trp Tyr Val Asp Gly Val Glu Val His Asn Ala Lys
        50                  55                  60

Thr Lys Pro Arg Glu Glu Gln Phe Asn Ser Thr Phe Arg Val Val Ser
65                  70                  75                  80

Val Leu Thr Val Val His Gln Asp Trp Leu Asn Gly Lys Glu Tyr Lys
                85                  90                  95

Cys Lys Val Ser Asn Lys Gly Leu Pro Ala Ser Ile Glu Lys Thr Ile
                100                 105                 110
```

```
Ser Lys Thr Lys Gly Gln Pro Arg Glu Pro Gln Val Tyr Thr Leu Pro
        115                 120                 125

Pro Ser Arg Glu Glu Met Thr Lys Asn Gln Val Ser Leu Thr Cys Leu
130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys Ala
    210                 215                 220

Ser Thr Lys Gly Pro Ala Pro Ile Ser Ser His Cys Arg Leu Asp Lys
225                 230                 235                 240

Ser Asn Phe Gln Gln Pro Tyr Ile Thr Asn Arg Thr Phe Met Leu Ala
                245                 250                 255

Lys Glu Ala Ser Leu Ala Asp Asn Asn Thr Asp Val Arg Leu Ile Gly
            260                 265                 270

Glu Lys Leu Phe His Gly Val Ser Met Ser Glu Arg Cys Tyr Leu Met
        275                 280                 285

Lys Gln Val Leu Asn Phe Thr Leu Glu Glu Val Leu Phe Pro Gln Ser
    290                 295                 300

Asp Arg Phe Gln Pro Tyr Met Gln Glu Val Val Pro Phe Leu Ala Arg
305                 310                 315                 320

Leu Ser Asn Arg Leu Ser Thr Cys His Ile Glu Gly Asp Asp Leu His
                325                 330                 335

Ile Gln Arg Asn Val Gln Lys Leu Lys Asp Thr Val Lys Lys Leu Gly
            340                 345                 350

Glu Ser Gly Glu Ile Lys Ala Ile Gly Glu Leu Asp Leu Leu Phe Met
        355                 360                 365

Ser Leu Arg Asn Ala Cys Ile
    370                 375

<210> SEQ ID NO 9
<211> LENGTH: 228
<212> TYPE: PRT
<213> ORGANISM: homo sapiens

<400> SEQUENCE: 9

Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
                20                  25                  30

Met Ile Ser Arg Thr Pro Glu Val Thr Cys Val Val Val Asp Val Ser
            35                  40                  45

His Glu Asp Pro Glu Val Gln Phe Asn Trp Tyr Val Asp Gly Val Glu
        50                  55                  60

Val His Asn Ala Lys Thr Lys Pro Arg Glu Glu Gln Phe Asn Ser Thr
65                  70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ala Pro
```

```
                100              105              110
Ile Glu Lys Thr Ile Ser Lys Thr Lys Gly Gln Pro Arg Glu Pro Gln
            115                  120                  125

Val Tyr Thr Leu Pro Pro Ser Arg Glu Glu Met Thr Lys Asn Gln Val
        130                  135                  140

Ser Leu Thr Cys Leu Val Lys Gly Phe Tyr Pro Ser Asp Ile Ser Val
145                  150                  155                  160

Glu Trp Glu Ser Asn Gly Gln Pro Glu Asn Asn Tyr Lys Thr Thr Pro
                    165                  170                  175

Pro Met Leu Asp Ser Asp Gly Ser Phe Phe Leu Tyr Ser Lys Leu Thr
                180                  185                  190

Val Asp Lys Ser Arg Trp Gln Gln Gly Asn Val Phe Ser Cys Ser Val
            195                  200                  205

Met His Glu Ala Leu His Asn His Tyr Thr Gln Lys Ser Leu Ser Leu
        210                  215                  220

Ser Pro Gly Lys
225

<210> SEQ ID NO 10
<211> LENGTH: 6
<212> TYPE: PRT
<213> ORGANISM: Artificial Sequence
<220> FEATURE:
<223> OTHER INFORMATION: short peptide

<400> SEQUENCE: 10

Ala Ser Thr Lys Gly Pro
1               5

<210> SEQ ID NO 11
<211> LENGTH: 5
<212> TYPE: PRT
<213> ORGANISM: Artificial Sequence
<220> FEATURE:
<223> OTHER INFORMATION: Hinge

<400> SEQUENCE: 11

Cys Pro Pro Cys Pro
1               5

<210> SEQ ID NO 12
<211> LENGTH: 6
<212> TYPE: PRT
<213> ORGANISM: Artificial Sequence
<220> FEATURE:
<223> OTHER INFORMATION: Synthetic Construct

<400> SEQUENCE: 12

Gly Pro Gly Pro Gly Pro
1               5

<210> SEQ ID NO 13
<211> LENGTH: 3
<212> TYPE: PRT
<213> ORGANISM: Artificial Sequence
<220> FEATURE:
<223> OTHER INFORMATION: Synthetic Construct

<400> SEQUENCE: 13

Glu Lys Arg
1
```

```
<210> SEQ ID NO 14
<211> LENGTH: 5
<212> TYPE: PRT
<213> ORGANISM: Artificial Sequence
<220> FEATURE:
<223> OTHER INFORMATION: Hinge

<400> SEQUENCE: 14

Glu Arg Lys Cys Cys
1               5
```